(12) United States Patent
Xiao et al.

(10) Patent No.: US 11,579,110 B2
(45) Date of Patent: *Feb. 14, 2023

(54) APTAMER-BASED SENSORS FOR DETECTION OF FENTANYL OPIOIDS

(71) Applicants: Yi Xiao, Miami, FL (US); Juan Canoura, Hialeah Gardens, FL (US)

(72) Inventors: Yi Xiao, Miami, FL (US); Juan Canoura, Hialeah Gardens, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,891

(22) Filed: May 27, 2022

(65) Prior Publication Data

US 2022/0291163 A1    Sep. 15, 2022

Related U.S. Application Data

(63) Continuation of application No. 17/354,342, filed on Jun. 22, 2021, now Pat. No. 11,408,850.

(60) Provisional application No. 63/042,242, filed on Jun. 22, 2020.

(51) Int. Cl.
    *C12N 15/115*     (2010.01)
    *G01N 27/327*     (2006.01)
    *G01N 21/64*     (2006.01)

(52) U.S. Cl.
    CPC ....... *G01N 27/3276* (2013.01); *C12N 15/115* (2013.01); *G01N 21/6428* (2013.01); *G01N 27/3277* (2013.01); *C12N 2310/16* (2013.01)

(58) Field of Classification Search
None
See application file for complete search history.

(56) References Cited

U.S. PATENT DOCUMENTS 7,803,542 B2    9/2010    Xiao et al.
10,550,395 B2    2/2020    Xiao et al.
10,655,132 B1    5/2020    Yang et al.
(Continued)

FOREIGN PATENT DOCUMENTS

WO      2018156806 A1    8/2018

OTHER PUBLICATIONS

Kammer, M. N., et al. "Quantification of opioids in urine using an aptamer-based free-solution assay." Analytical chemistry 91.16 (2019): 10582-10588.

*Primary Examiner* — Robert T. Crow
(74) *Attorney, Agent, or Firm* — Saliwanchik, Lloyd & Eisenschenk

(57) ABSTRACT

The subject invention provides materials and methods for single-step fluorescence and electrochemical detection of small molecules, e.g., fentanyl and its analogs, in a sample. The subjection invention provides nucleic acids materials, e.g., aptamers (nucleic acid oligonucleotides) that can bind to fentanyl and its analogs with nanomolar affinity and high specificity against illicit drugs, adulterants, and cutting agents commonly existing in seized samples. The method for detecting fentanyl and/or its analogs in a sample comprises contacting the sample with an aptamer-based sensor selective for fentanyl and its analogs, and sensitively, specifically, and rapidly detecting fentanyl and/or its analogs in the sample.

18 Claims, 33 Drawing Sheets

Specification includes a Sequence Listing.

(56) References Cited

U.S. PATENT DOCUMENTS

| | | |
|---|---|---|
| 10,683,507 B2 | 6/2020 | Xiao et al. |
| 10,725,058 B2 | 7/2020 | Xiao et al. |
| 10,907,162 B2 | 2/2021 | Xiao et al. |
| 10,907,163 B1 | 2/2021 | Xiao et al. |
| 10,948,504 B2 | 3/2021 | Xiao et al. |
| 11,060,095 B2 | 7/2021 | Yang et al. |
| 11,162,960 B2 | 11/2021 | Xiao et al. |
| 11,408,850 B2 * | 8/2022 | Xiao .................. G01N 27/3276 |
| 2007/0059732 A1 * | 3/2007 | Bamdad ................ G01N 27/48 977/924 |
| 2007/0154909 A1 | 7/2007 | Xiao et al. |
| 2018/0179540 A1 | 6/2018 | Jackson |
| 2021/0041470 A1 | 2/2021 | Kaur et al. |

* cited by examiner

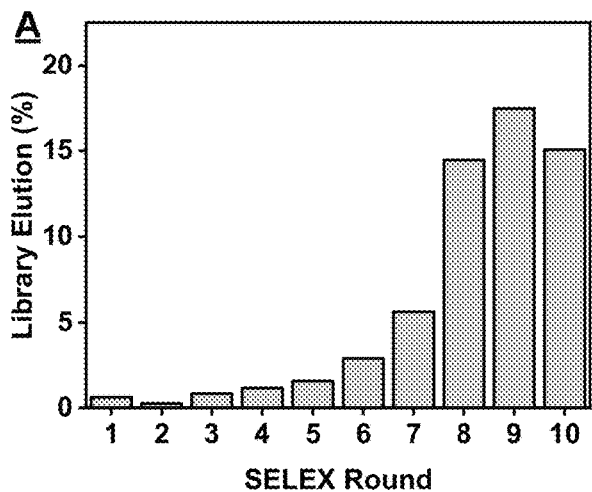
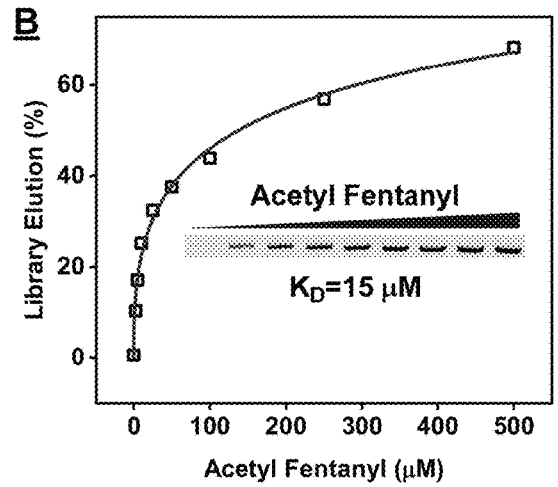
FIG. 4A  FIG. 4B
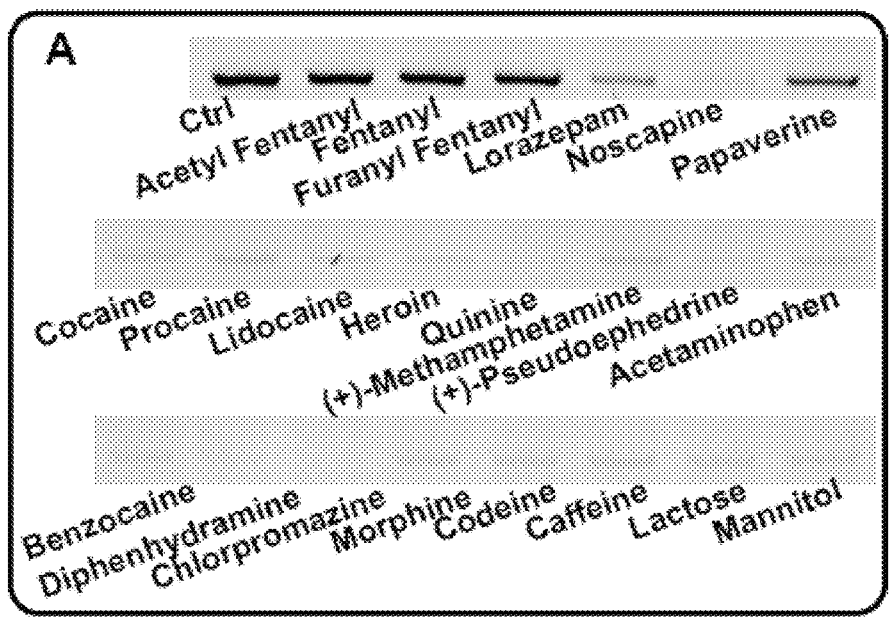
FIG. 5A

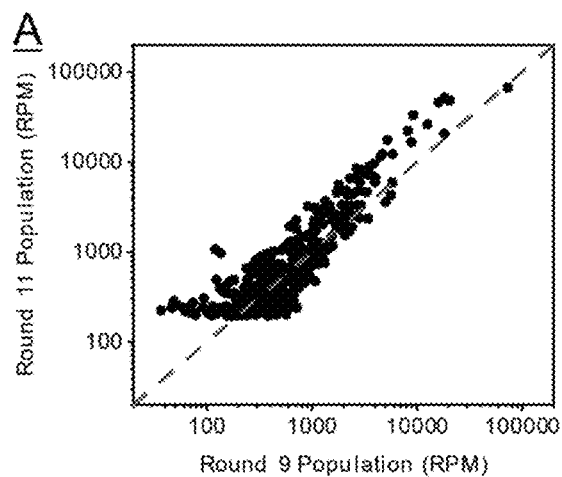 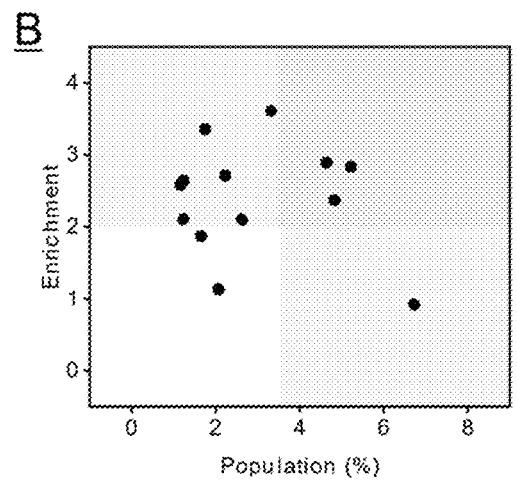
FIG. 8A  FIG. 8B
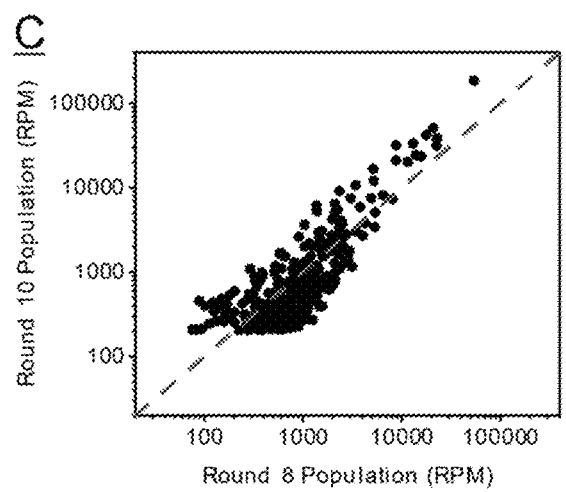 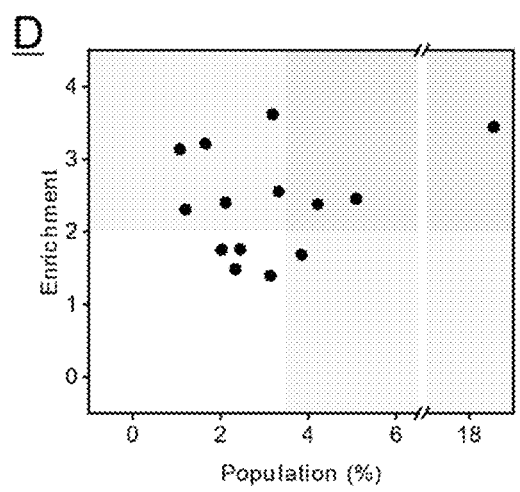
FIG. 8C  FIG. 8D

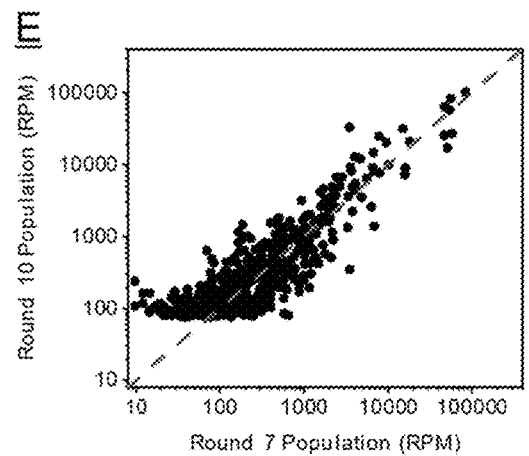 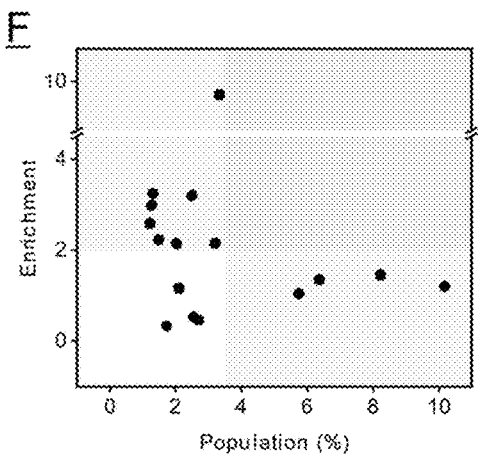
FIG. 8E  FIG. 8F
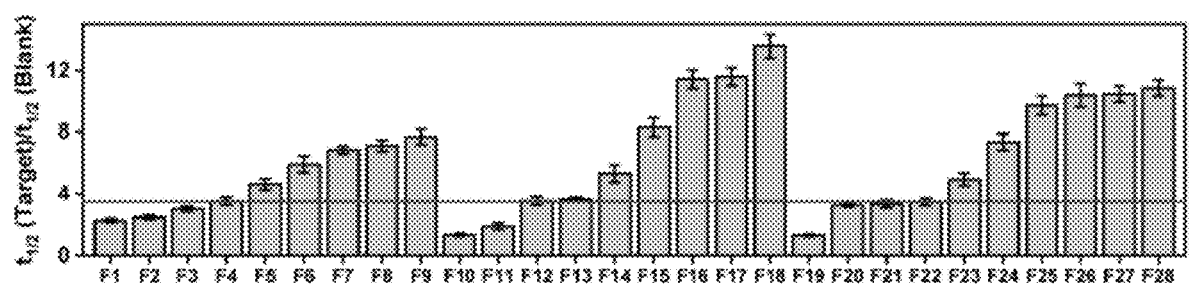
FIG. 9

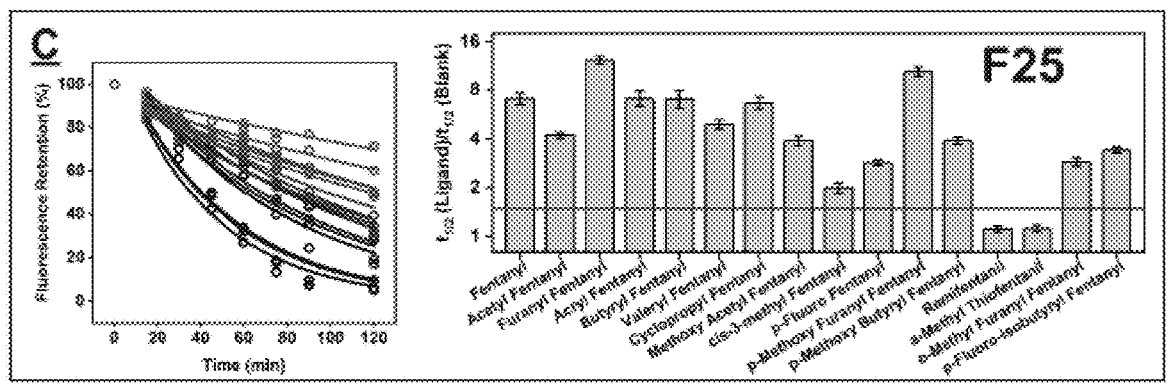
FIG. 21C
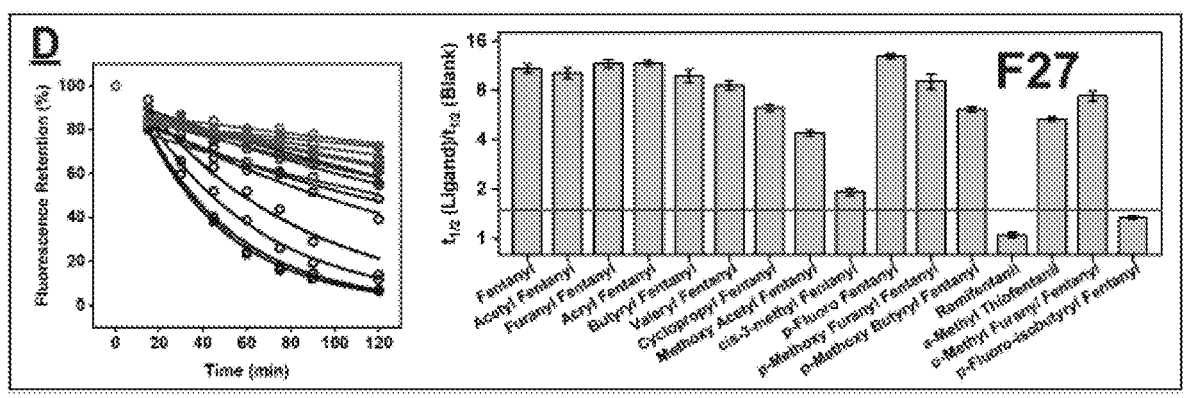
FIG. 21D
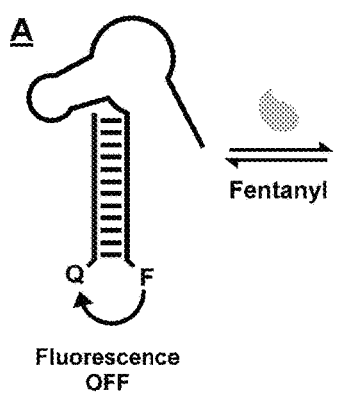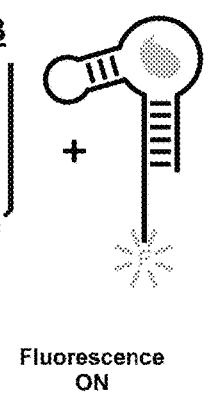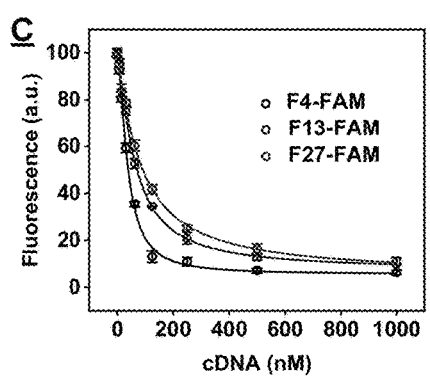
FIG. 22A  FIG. 22B  FIG. 22C

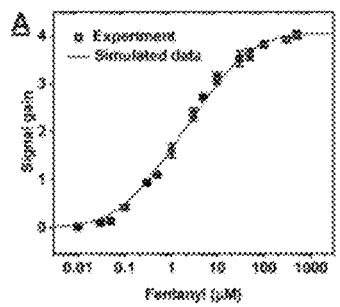
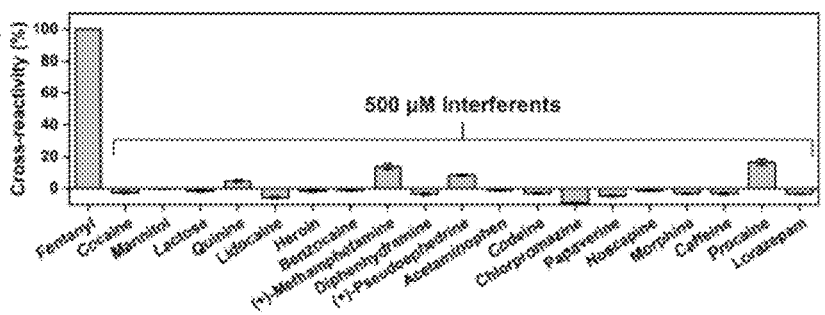
FIG. 24A                FIG. 24B
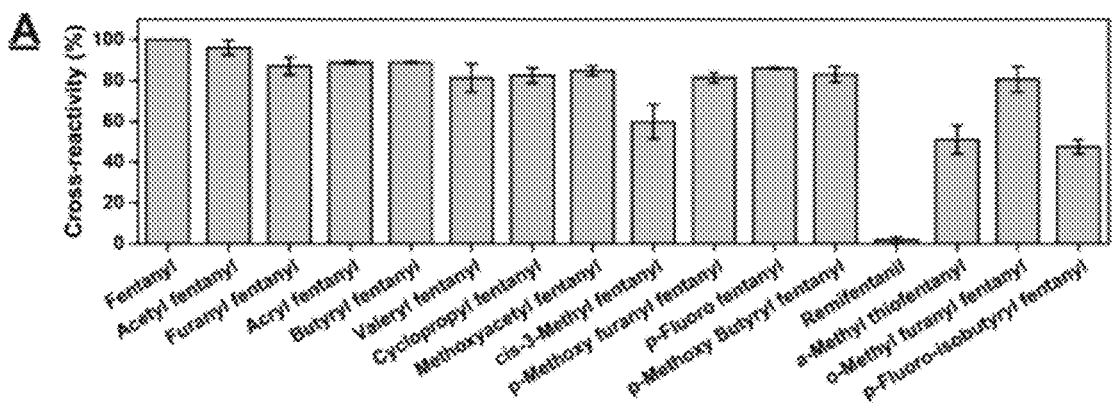
FIG. 25A
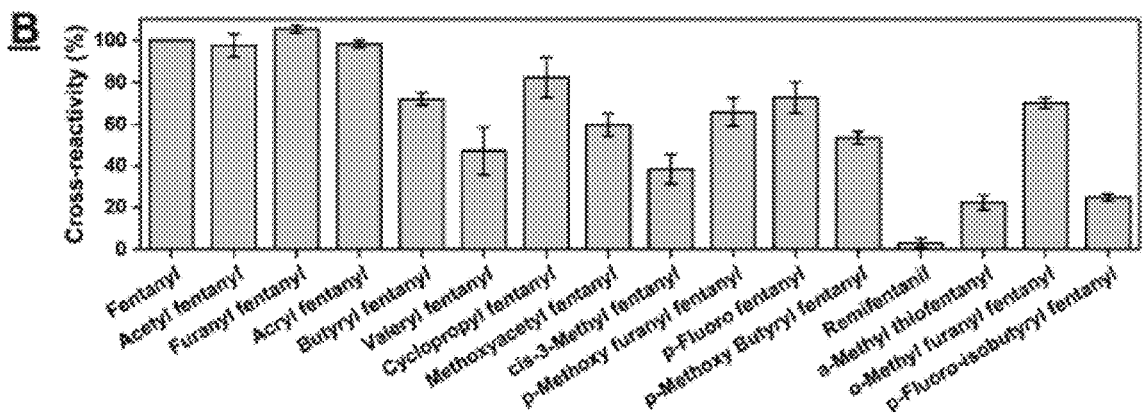
FIG. 25B

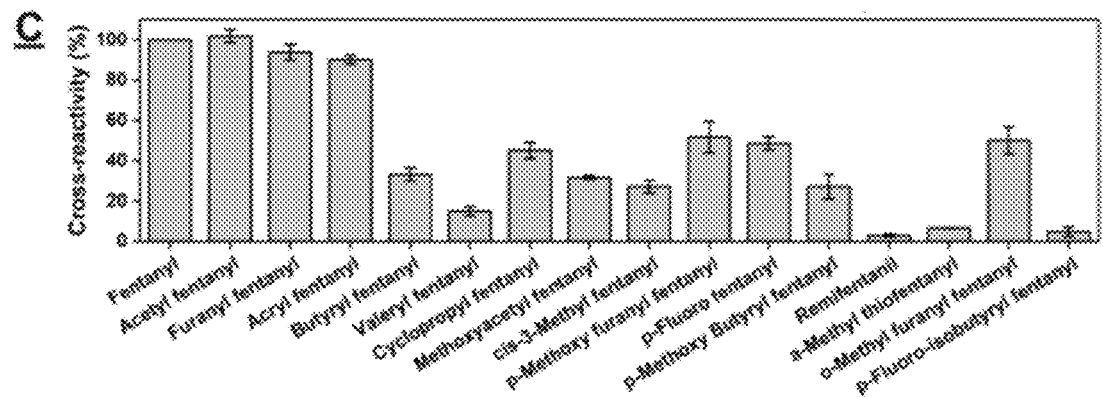
FIG. 25C
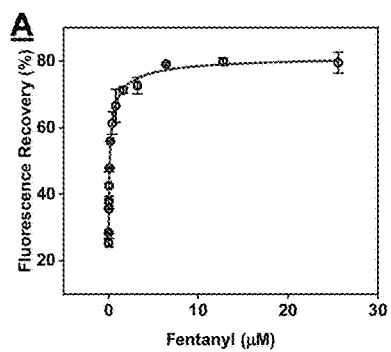 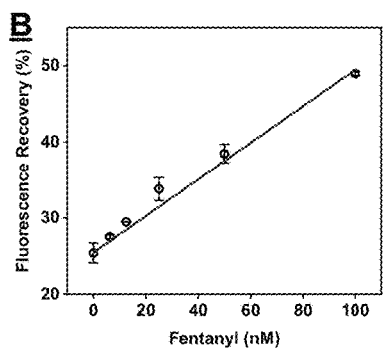 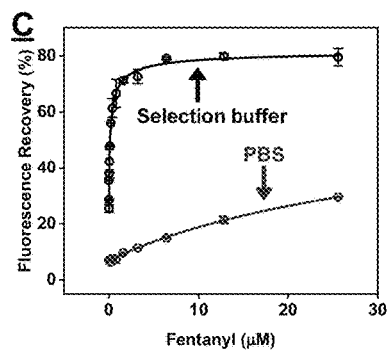
FIG. 26A  FIG. 26B  FIG. 26C

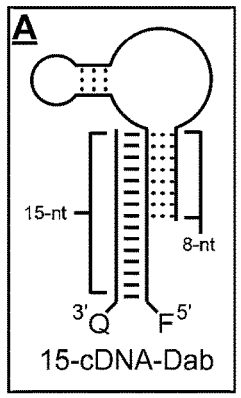
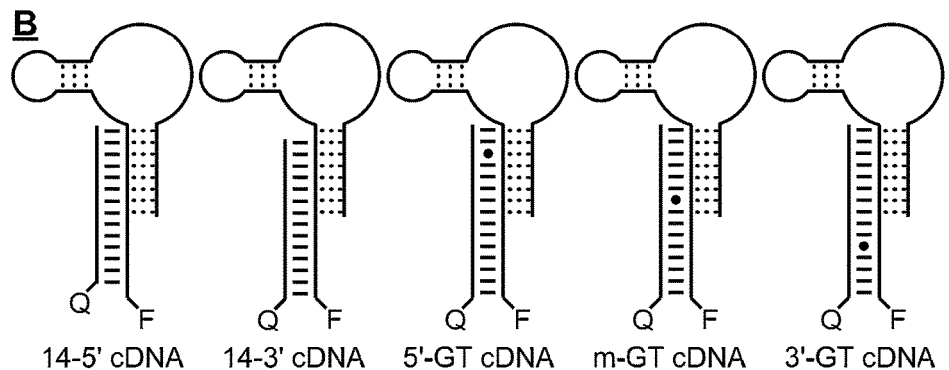
FIG. 27A  FIG. 27B
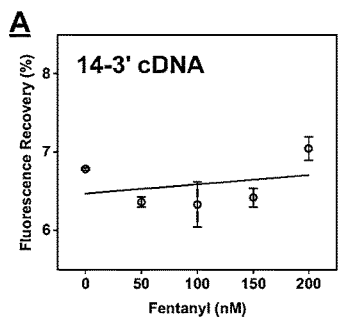
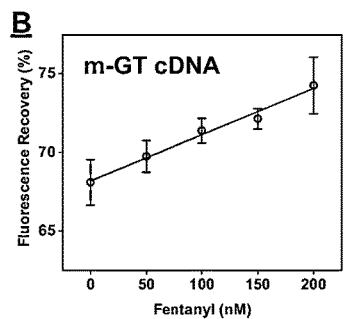
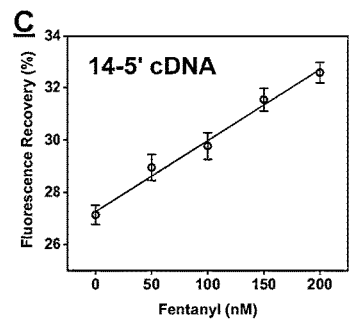
FIG. 28A  FIG. 28B  FIG. 28C
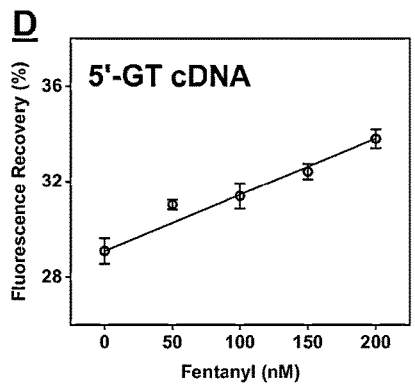
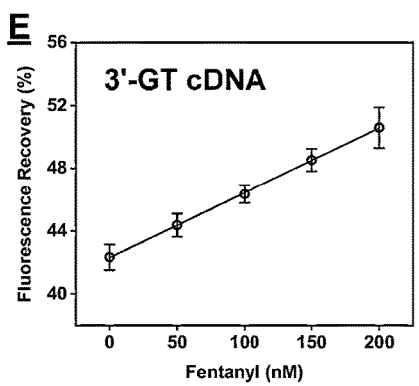
FIG. 28D  FIG. 28E

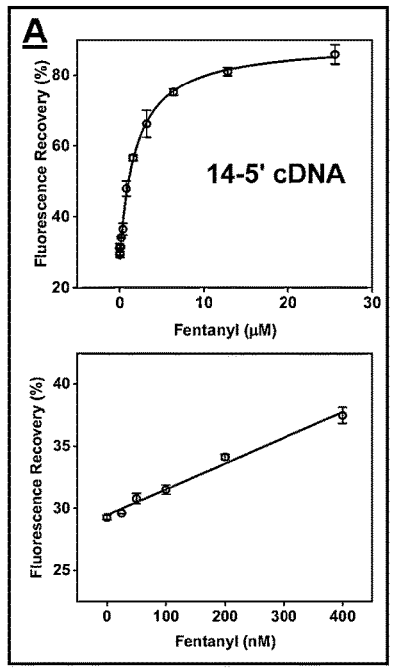
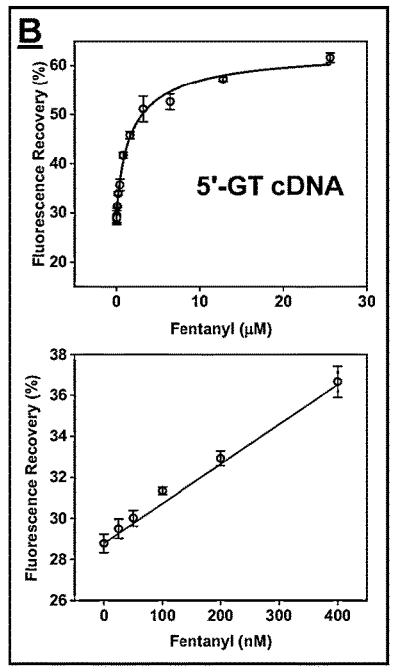
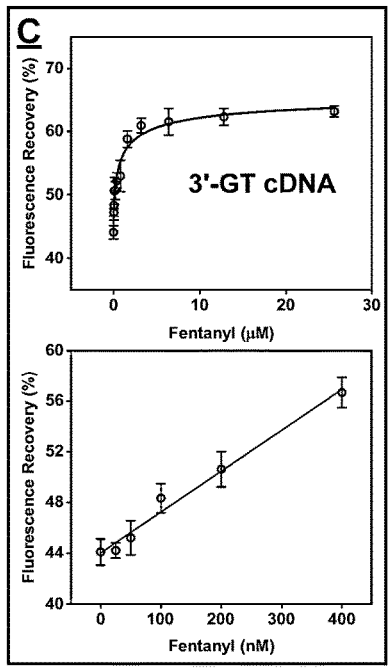
FIG. 29A FIG. 29B FIG. 29C
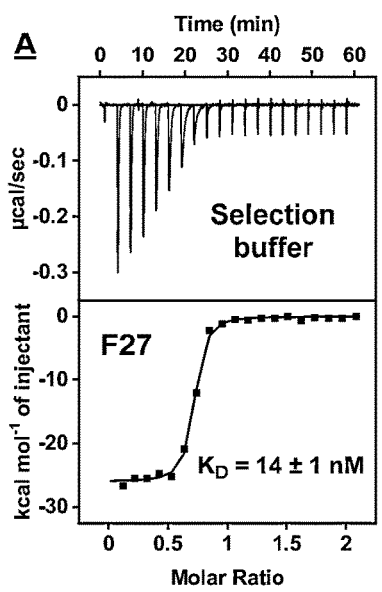
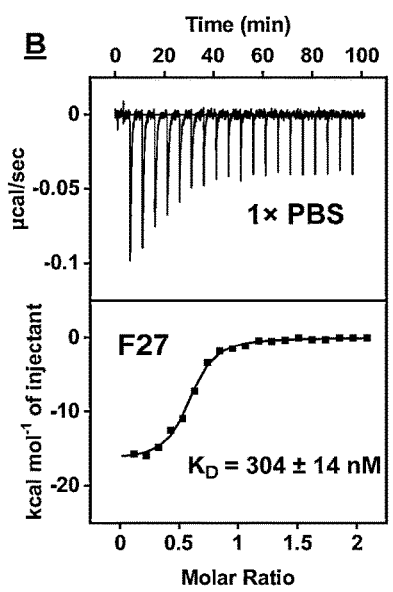
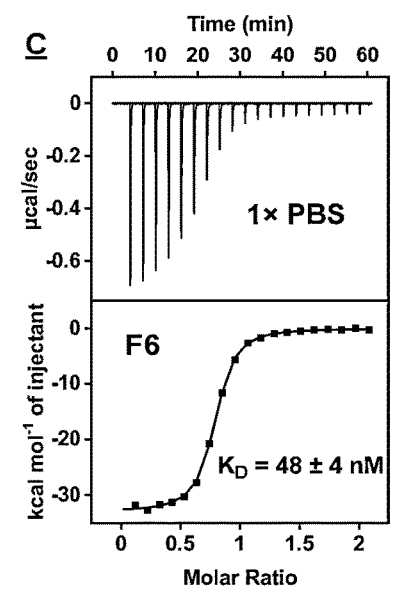
FIG. 30A FIG. 30B FIG. 30C FIG. 31A
FIG. 31B
FIG. 31C
FIG. 31D
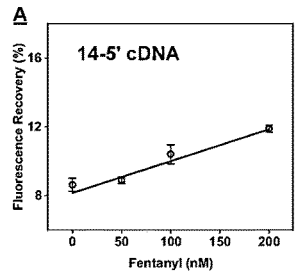
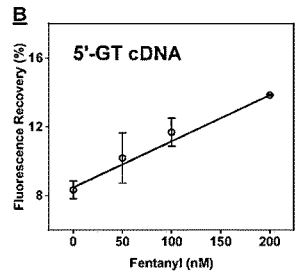
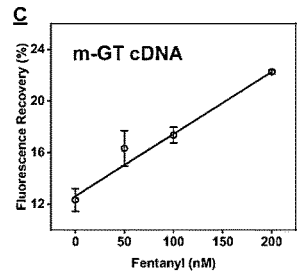
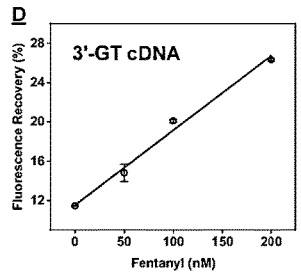
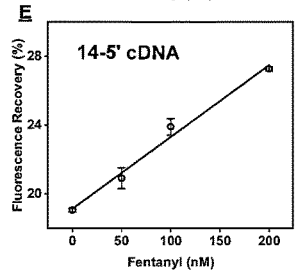
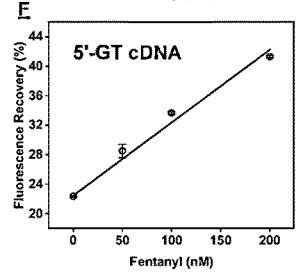
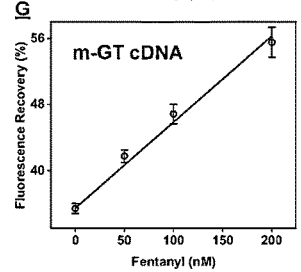
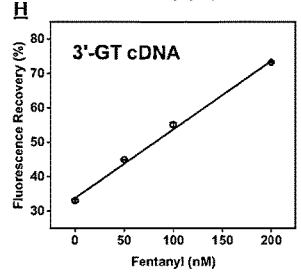
FIG. 31E
FIG. 31F
FIG. 31G
FIG. 31H
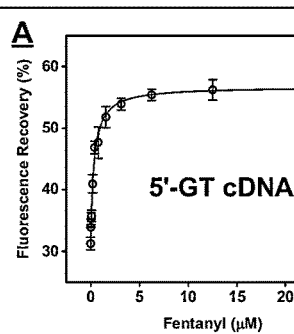
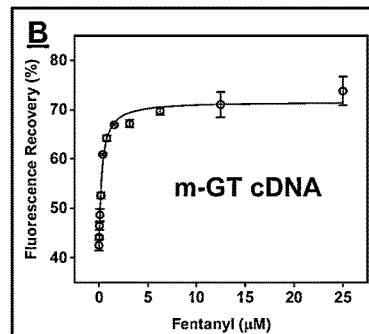
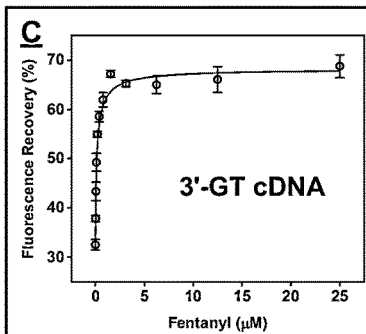
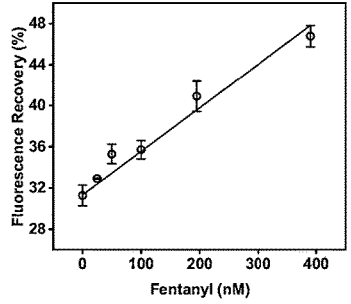
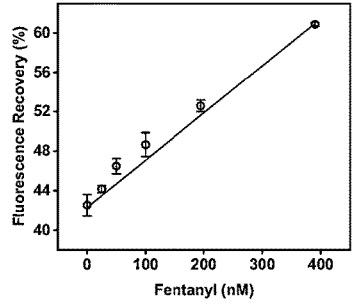
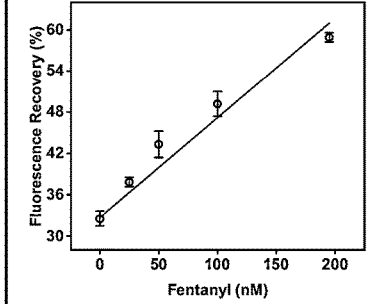
FIG. 32A
FIG. 32B
FIG. 32C

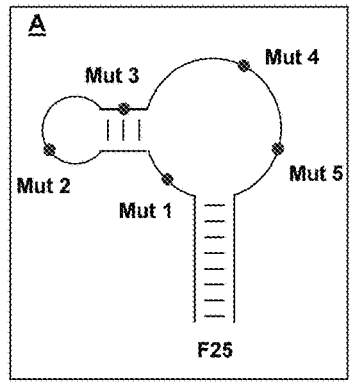
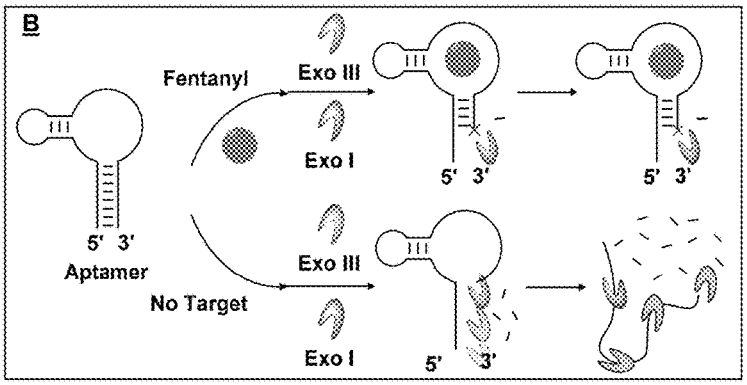
FIG. 33A              FIG. 33B
FIG. 34A        FIG. 34B        FIG. 34C        FIG. 34D
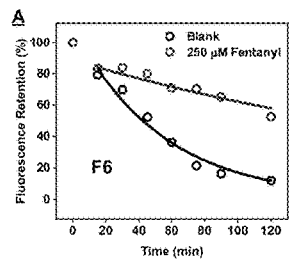 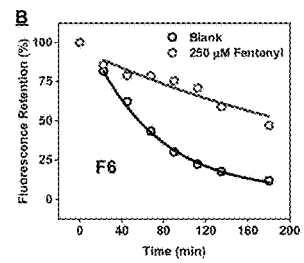 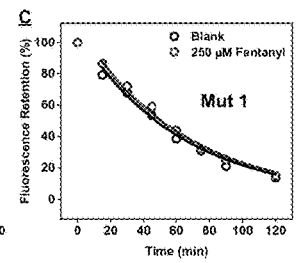 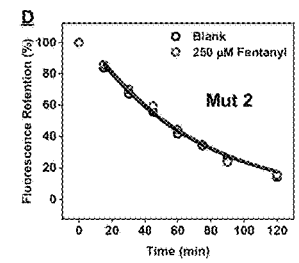
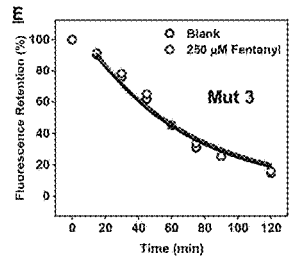 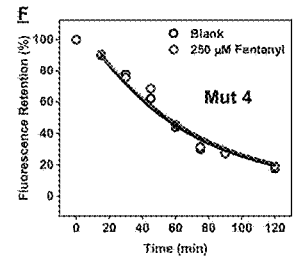 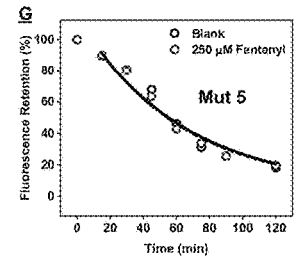
FIG. 34E        FIG. 34F        FIG. 34G FIG. 35A  FIG. 35B  FIG. 35C
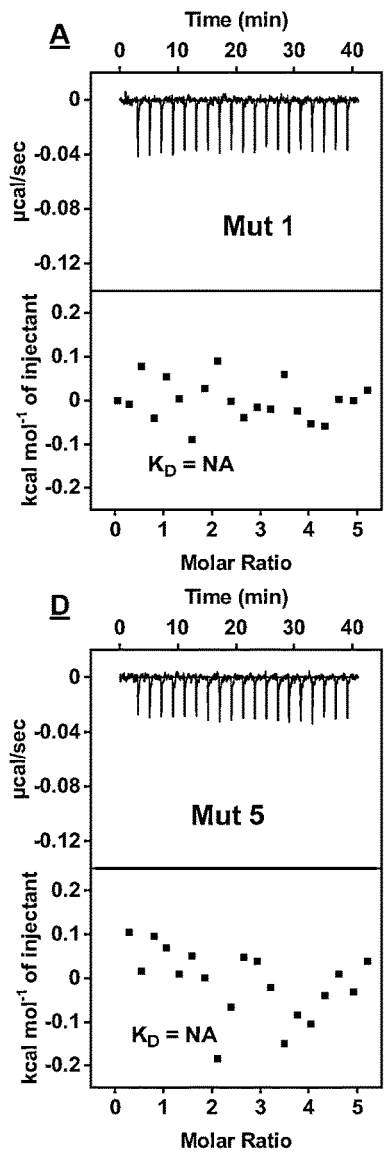
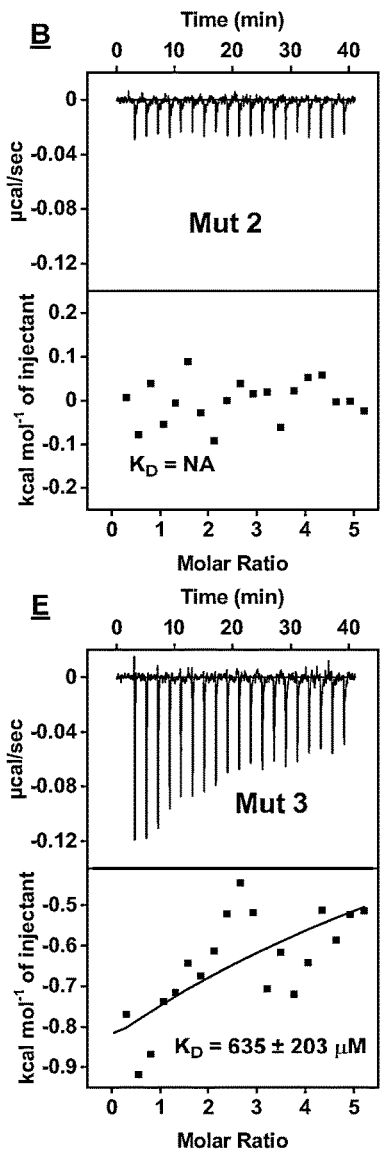
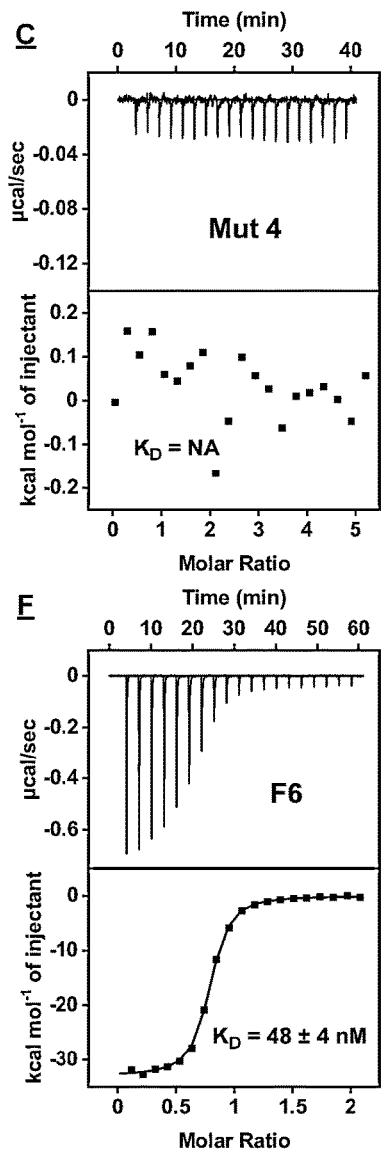
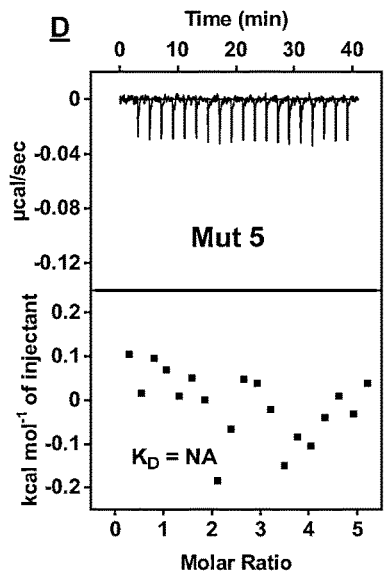
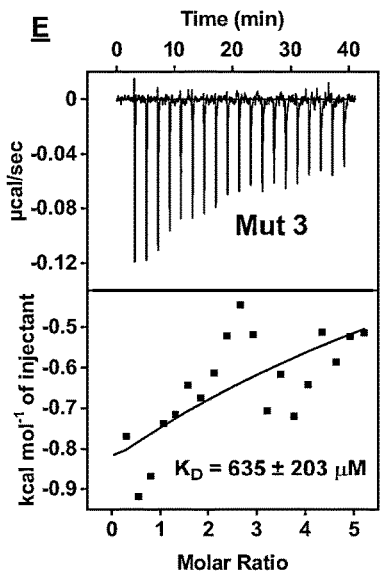
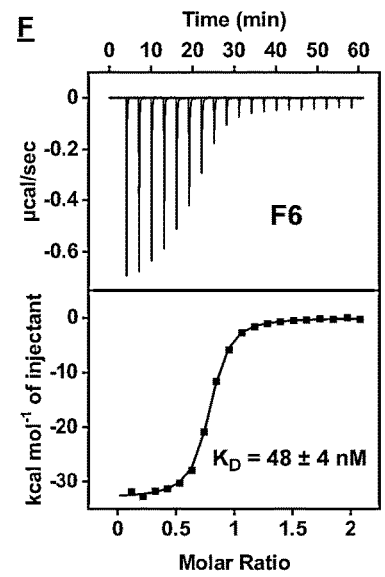
FIG. 35D  FIG. 35E  FIG. 35F

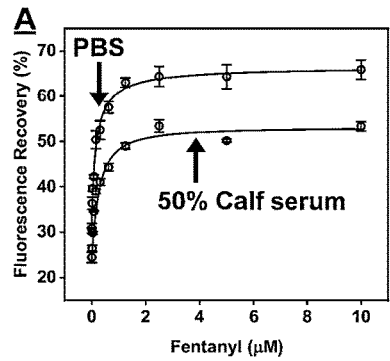 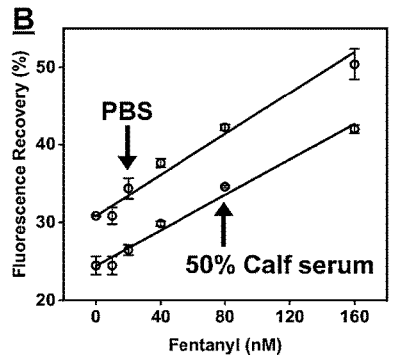 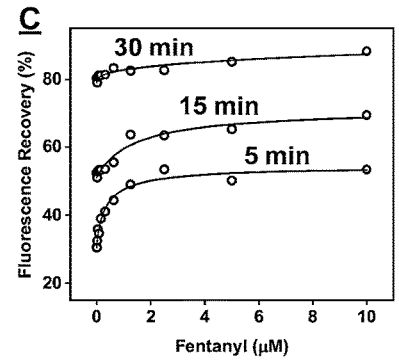
FIG. 36A  FIG. 36B  FIG. 36C
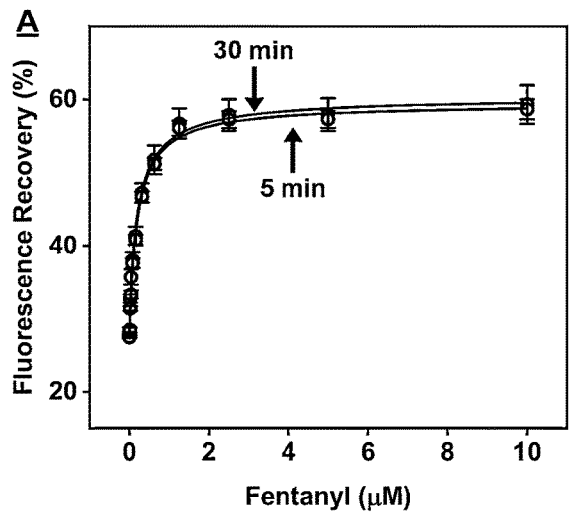 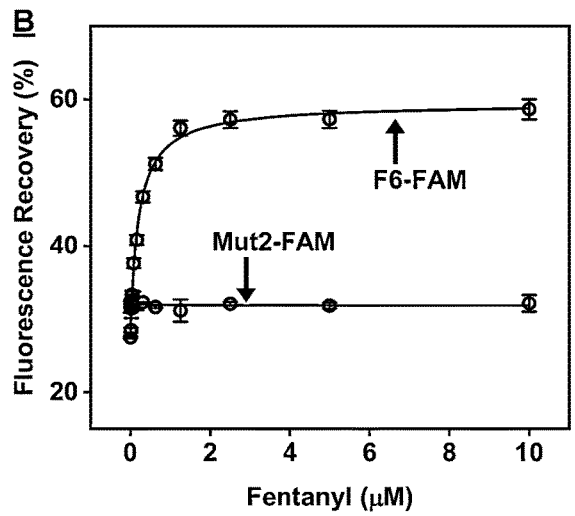
FIG. 37A  FIG. 37B

— 1 —

APTAMER-BASED SENSORS FOR DETECTION OF FENTANYL OPIOIDS

CROSS-REFERENCE TO A RELATED APPLICATION

This application is a continuation application of U.S. Ser. No. 17/354,342, filed Jun. 22, 2021, which claims the benefit of U.S. provisional application Ser. No. 63/042,242, filed Jun. 22, 2020, both of which are incorporated herein by reference in its entirety.

GOVERNMENT SUPPORT

This invention was made with government support under Grant No. 2019-DU-BX-0024 awarded by the National Institute of Justice and under Grant No. IIP1739805 awarded by the National Science Foundation. The government has certain rights in the invention.

SEQUENCE LISTING

The Sequence Listing for this application is labeled "SeqList-06Dec21-ST25.txt," which was created on Dec. 6, 2021, and is 19 KB. The Sequence Listing is incorporated herein by reference in its entirety.

BACKGROUND OF THE INVENTION

Aptamers are single-stranded oligonucleotides or peptides that are isolated from randomized nucleic-acid or peptide libraries through an in vitro method termed systematic evolution of ligands by exponential enrichment (SELEX). In particular, oligonucleotides have several characteristics that make them favorable as bioreceptors including high chemical stability, ease and affordability of synthesis, and low batch-to-batch variability alongside having high target-binding affinities and well-defined specificity. They have recently gained wide appeal as bioreceptors for biosensing, imaging, and therapeutics due to their low cost of production, ease of modification, and long shelf life.

Extensive research has been performed on aptamers regarding their application in remedying a variety of problems in various areas such as medical diagnostics, environmental monitoring, drug detection, and food safety. In tandem, and arguably to a lesser extent, these applied research thrusts are supplemented by fundamental studies of aptamers, which primarily focus on the process by which they are generated (via SELEX) and the exact nature of the interaction of aptamers with their target ligands.

It has been proffered that the in vitro nature of aptamer generation permits the development of bioreceptors for ligands that antibodies cannot be made for with precise control over affinity and specificity. In fact, aptamers have been isolated against various targets as small as ions to as large as whole cells.

It is challenging to generate suitable bioreceptors for a family of small molecules which share the same core structure. Usually, modifications onto the core structure can impair the binding affinity of existing antibodies. Therefore, antibody-based immunoassays face difficulties in detecting such family members. Aptamers are an excellent alternative as bioreceptors for these small-molecule families, as their cross-reactivity can be tuned using in vitro isolation strategies such as serial-and-parallel selection and their specificity can be precisely controlled by well-designed counter SELEX strategies, which allow for the isolation of aptamers with broad cross-reactivity to the target family members and excellent specificity against non-family compounds.

Fentanyl and its analogs are highly potent synthetic opioids that pose a serious threat to public health and safety. These compounds are a new danger for law enforcement officials. Fentanyl has a role as an opioid analgesic, a μ-opioid receptor agonist, an anesthesia adjuvant, an intravenous anesthetic, an adjuvant and an anesthetic. It is typically used to treat patients with severe pain or to manage pain after surgery. Fentanyl, however, as a μ-opiate agonist, can produce drug dependence and tolerance, which may cause significant issues.

Current immunoassays used for fentanyl screening are prone to false negatives and positives due to inability to control antibody cross-reactivity and specificity during the generation process. Thus, there is a need to develop and isolate aptamers that can broadly bind challenging small molecules, e.g., fentanyl and its analogs, and use such aptamers for rapidly and selectively detecting these small molecules for, e.g., drug abuse, dependence, and addiction.

BRIEF SUMMARY OF THE INVENTION

The subject invention provides methods, assays and materials for rapid and specific detection of small molecules in a sample, in particular, in both clinical and field settings. In one embodiment, the method for detecting a small-molecule target in a sample comprises contacting the sample with an aptamer-based sensor selective for the small-molecule target, and detecting the small-molecule target in the sample.

In one embodiment, the small molecules according to the subject invention are selected from the fentanyl family, including fentanyl, its analogs, its derivatives and salts thereof. In a specific embodiment, the small molecule are fentanyl-related molecules that includes, but are not limited to, Fentanyl, Acetyl fentanyl, fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.

The aptamers according to the subject invention bind to and recognize the core structure shared by fentanyl and its analogs and have nanomolar-micromolar affinity for fentanyl and its analogs while having no response for the majority of interferents existing in the sample.

The "salts" can be with an inorganic acid, such as hydrochloric acid, hydrobromic acid, perchloric acid, nitric acid, thiocyanic acid, sulfuric acid, and phosphoric acid; an organic acid, such as citric acid, trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases.

In one embodiment, the subject invention provides an aptamer-based sensor comprising one or more aptamers according to the subject invention and, optionally, a modified complimentary nucleic acid sequence. In a specific embodiment, the aptamer-based sensor comprises three aptamers.

In one embodiment, the subject invention provides an electrochemical aptamer-based (E-AB) sensor comprising a structure-switching aptamer and an electrode, wherein the structure-switching aptamer is labeled with a redox tag at one end and a functional group (such as thiol) at the other end, and wherein the structure-switching aptamer is conjugated to the surface of the electrode via the functional group. Advantageously, the E-AB sensor can perform on-site, interference-free screening for trace amounts of fentanyl and its derivatives in seized substances within seconds.

In one embodiment, the method, according to the subject invention, for rapid, sensitive and specific detection of one or more small molecule targets in a sample comprises contacting the sample with an aptamer-based sensor selective for the small-molecule target, wherein the aptamer-based sensor comprises one or more aptamers, and detecting one or more small-molecule targets in the sample, wherein the detection of the small-molecule target comprises measuring a signal generated upon binding of the small-molecule targets to the binding domain of the aptamer.

In one embodiment, the method comprises contacting the sample with the E-AB sensor of the subject invention, and detecting one or more small-molecule targets in the sample, wherein the detection of small-molecule targets comprises measuring a signal generated from a signal reporter. In a further embodiment, the detection of the small-molecule target comprises measuring a signal generated upon binding of the small-molecule target with the E-AB sensor, wherein the signal is an increase in current.

BRIEF DESCRIPTION OF THE DRAWINGS

FIGS. 4A-4B show the enrichment of acetyl fentanyl-binding aptamers. (A) Library elution during each round upon addition of acetyl fentanyl. (B) Determination of round 10 pool affinity using a gel elution assay. Elution of library was done using 0, 2.5, 5, 10, 25, 50, 100, 250, or 500 µM acetyl fentanyl (left to right).

FIGS. 5A-5B show the determination of cross reactivity of the round 10 acetyl fentanyl pool. (A) Elution of library in the presence of 25 µM acetyl fentanyl, fentanyl, or furanyl fentanyl, or 100 µM of lorazepam or noscapine, or 250 µM of papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, lactose, or mannitol. (B) Cross-reactivity of library against various ligands relative to 25 µM acetyl fentanyl.

FIGS. 8A-8F show the high-throughput sequencing data analysis of fentanyl, acetyl fentanyl, and furanyl fentanyl pools. (A) Analysis of sequence population growth between rounds 9 and 11 for fentanyl pools. (B) Enrichment of sequences present at >1% population of round 11 fentanyl pool. (C) Analysis of sequence population growth between rounds 8 and 10 for acetyl fentanyl pools. (D) Enrichment of sequences present at >1% population of round 10 acetyl fentanyl pool. (E) Analysis of sequence population growth between rounds 7 and 10 for furanyl fentanyl pools. (F) Enrichment of sequences present at >1% population of round 10 furanyl fentanyl pool. Sequences selected for synthesis are highlighted by the shaded area.

FIG. 9 shows the screening of high-affinity aptamers using an exonuclease assay. $t_{1/2}$ ratio of each aptamer was calculated for 100 µM of their respective selection target.

FIGS. 21A-21D show the screening the cross-reactivity of four aptamer candidates to fentanyl and its analogs using an exonuclease digestion assay. Time course digestion and $t_{1/2}$ ratio of (A) F23, (B) F24, (C) F25, and (D) F27. Aptamers were digested in the absence and presence of 100 μM Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.

FIGS. 22A-22C show the strand-displacement fluorescence assay for detection of fentanyl and its analogs. The strand-displacement fluorescence assay utilizes a quencher (Dabcyl, Dab) modified cDNA (15-cDNA-Dab) and fluorophore (Fluorescein, FAM) modified aptamer. (A) When these two strands are hybridized, the fluorophore is brought in close proximity to the quencher, suppressing its fluorescence. (B) Upon addition of fentanyl, the aptamer will fold, displacing the 15-cDNA-Dab and recovering fluorescence. (C) Fluorescence quenching efficiency of F4-FAM, F13-FAM, and F27-FAM. Aptamers were incubated with 0, 8, 16, 31, 62.5, 125, 250, 500, or 1000 nM 15-cDNA-Dab.

FIGS. 24A-24B show the strand-displacement fluorescence assay performance using a triple-aptamer sensor. (A) Fentanyl calibration curve and (B) specificity of the triple-aptamer sensor. Calibration curve was constructed using 0, 0.01, 0.03, 0.05, 0.1, 0.3, 0.5, 1, 3, 5, 10, 30, 50, 100, 300, and 500 μM fentanyl. Specificity test was performed against 500 μM cocaine, mannitol, lactose, quinine, lidocaine, heroin, benzocaine, (+)-methamphetamine, diphenhydramine, (+)-pseudoephedrine, acetaminophen, codeine, chlorpromazine, papaverine, noscapine, morphine, caffeine, procaine, and lorazepam, and their cross-reactivities were calculated relative to the signal produced by 100 μM fentanyl.

FIGS. 25A-25C show the cross-reactivity of the triple-aptamer sensor against fentanyl and 15 of its analogs. Cross-reactivity observed for (A) 50, (B) 5, and (C) 0.5 μM of Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl. Cross-reactivity was calculated relative to the signal produced by fentanyl.

FIG. 26A-26C show the detection of fentanyl using a strand-displacement fluorophore-quencher assay based on F27-FAM/15-cDNA-Dab. (A) A calibration curve was constructed using different concentrations of fentanyl (0, 0.006, 0.012, 0.025, 0.05, 0.1, 0.2, 0.4, 0.8, 1.6, 3.2, 6.4, 12.8, and 25.6 μM) in selection buffer (10 mM Tris-HCl, 20 mM NaCl, 0.5 MgCl$_2$, pH 7.4). (B) Linear range of fentanyl detection at low concentrations. (C) Performance of the assay with 0, 0.006, 0.012, 0.025, 0.05, 0.1, 0.2, 0.4, 0.8, 1.6, 3.2, 6.4, 12.8, and 25.6 µM fentanyl in selection buffer versus 1×PBS (10 mM Phosphate buffer, 137 mM NaCl, 2.7 mM KCl, 1 mM MgCl$_2$, pH 7.4). Error bars indicate the standard error from three individual experiments.

FIGS. 27A-27B show the design of Q-cDNA strands for detection of fentanyl in 1×PBS. (A) The initial design features a 15-nt complementary region between F27-FAM and 15-cDNA-Dab that competes with the 8-bp stem of the target-bound aptamer. (B) Alternative cDNA designs with reduced complementarity or replacement of a single matched base-pair with a mutated G-T wobble pair (dot).

FIGS. 28A-28E show the detection of 0, 50, 100, 150, and 200 nM fentanyl using F27-FAM and (A) 14-3' cDNA, (B) m-GT cDNA, (C) 14-5' cDNA, (D) 5'-GT cDNA or (E) 3'-GT cDNA in 1×PBS. Error bars indicate the standard error between three individual experiments.

FIGS. 29A-29C show the calibration curves at concentrations of 0, 0.006, 0.012, 0.025, 0.05, 0.1, 0.2, 0.4, 0.8, 1.6, 3.2, 6.4, 12.8, and 25.6 µM fentanyl for sensors constructed with 50 nM F27-FAM and 150 nM (A) 14-5' cDNA, (B) 5'-GT cDNA, or (C) 3'-GT cDNA. Error bars indicate the standard error from three individual experiments.

FIGS. 30A-30C show the determination of binding affinity of fentanyl-binding aptamers using ITC. Binding affinity of F27 in (A) selection buffer or (B) 1×PBS. (C) Binding affinity of F6 in 1×PBS. Top panels display the heat generated from each titration of fentanyl into the aptamer. Bottom panels show the integrated heat of each titration after correcting for the heat of dilution of the titrant.

FIGS. 31A-31H show the detection of 0, 50, 100, and 200 nM fentanyl in 1×PBS using sensors constructed with 50 nM F6-FAM and (A) 150 nM 14-5' cDNA, (B) 150 nM 5'-GT cDNA, (C) 150 nM m-GT cDNA, (D) 150 nM 3'-GT cDNA, (E) 50 nM 14-5' cDNA, (F) 50 nM 5'-GT cDNA, (G) 50 nM m-GT cDNA, or (H) 50 nM 3'-GT. Error bars indicate the standard error of three individual experiments.

FIGS. 32A-32C show the calibration curves from 0, 0.006, 0.012, 0.025, 0.05, 0.1, 0.2, 0.4, 0.8, 1.6, 3.2, 6.4, 12.8, and 25.6 µM fentanyl with sensors based on 50 nM F6-FAM and 50 nM (A) 5'-GT cDNA, (B) m-GT cDNA, or (C) 3'-GT cDNA in 1×PBS. Top panels display entire calibration curves and bottom panels represent calibration linear ranges. Error bars indicate the standard error between three experiments.

FIGS. 33A-33B show the binding affinity of aptamer mutants to fentanyl. (A) Design of five point mutants derived from F6, with mutation sites circled in red. (B) Scheme of the exonuclease digestion assay, in which target binding (top) interferes with the enzymatic digestion of the aptamer, which would otherwise be completely digested to mononucleotides (bottom).

FIGS. 34A-34G show the screening fentanyl affinity of F6 mutants using the exonuclease digestion assay. F6 in (A) selection buffer or (B) 1×PBS was tested. (C) Mut 1, (D) Mut 2, (E) Mut 3, (F) Mut 4, and (G) Mut 5 in 1×PBS were screened. All plots show fluorescence in the absence or presence of 250 µM fentanyl.

FIGS. 35A-35F show the affinity determination of (A) Mut 1, (B) Mut 2, (C) Mut 4, (D) Mut 5, (E) Mut 3 and (F) F6 via ITC. The top panels display the heat generated from each titration of fentanyl into the aptamer. The bottom panels show the integrated heat of each titration after correcting for the heat of dilution of the titrant.

FIGS. 36A-36C show the performance of the 3'-GT cDNA/F6-FAM pair in 50% calf serum. (A) Calibration curves for 0.01, 0.02, 0.04, 0.08, 0.16, 0.32, 0.64, 1.28, 2.56, 5.12, and 10.24 µM fentanyl in 1×PBS and 50% calf serum. (B) Linear ranges for data from panel A. (C) Serum nuclease degradation of the 3'-GT cDNA/F6-FAM pair reduces sensor performance over time.

FIGS. 37A-37B show the performance of 3'-GT cDNA/F6-FAM pair in 50% deactivated calf serum. (A) Fentanyl calibration curve in 50% deactivated calf serum after 5 min and 30 min incubation. (B) Fentanyl calibration curve for 3'-GT cDNA with F6-FAM or mut2-FAM in 50% deactivated calf serum. Error bars indicate the standard error from three individual experiments.

BRIEF DESCRIPTION OF SEQUENCES

Figures 1A, 1B:
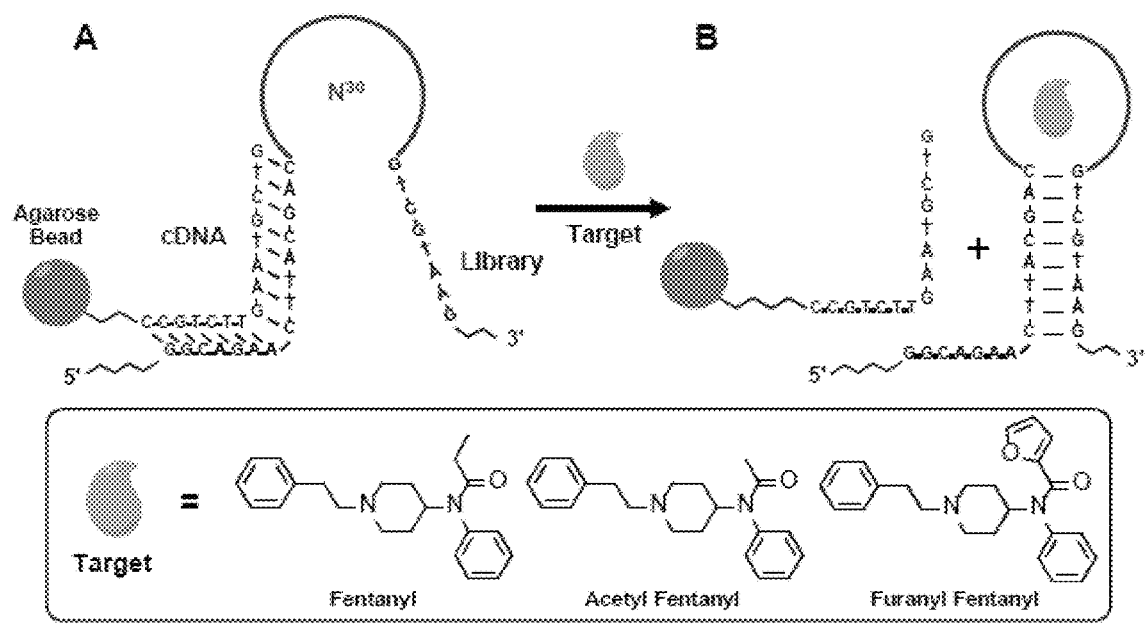
FIGS. 1A-1B show the selection strategy of library-immobilized SELEX employing a structured library design. (A) The library (SEQ ID NO: 1) is designed of a 30-nucleotide random region (N30) flanked by two constant regions comprised of a self-complementary 8-nucleotide region and two primer binding sites. The library is complementary to a 15-nucleotide complementary DNA (cDNA, SEQ ID NO: 84) modified with a biotin tag allowing for immobilization onto a streptavidin-modified agarose bead. (B) The binding of the target to the library stabilizes the self-complementary 8-nucleotide region and displaces the cDNA. The three selection targets are displayed in the box below.

SEQ ID NO: 1 is a DNA library contemplated for use according to the subject invention, wherein N30 are random bases.

SEQ ID NO: 2 is a biotinylated-cDNA sequence contemplated for use according to the subject invention.

SEQ ID NO: 3 is a forward primer contemplated for use according to the subject invention.

SEQ ID NO: 4 is a biotinylated-reverse primer contemplated for use according to the subject invention.

SEQ ID NO: 5 is a reverse primer contemplated for use according to the subject invention.

SEQ ID NOs: 6-33 are sequences of isolated DNA aptamers contemplated for use according to the subject invention.

SEQ ID NOs: 34-36 are sequences of isolated DNA aptamers with a fluorescent label contemplated for use according to the subject invention.

SEQ ID NO: 37 is a quencher-modified cDNA complementary strand for use according to the subject invention.

SEQ ID NO: 38 is a sequences of a truncated DNA aptamer contemplated for use according to the subject invention.

SEQ ID NO: 39 is a 5'-thiol and 3'-methylene blue modified DNA aptamer contemplated for use according to the subject invention.

SEQ ID NO: 40 is a complimentary DNA sequence contemplated for use according to the subject invention.

SEQ ID NO: 41 is a sequence of a truncated DNA aptamer library contemplated for use according to the subject invention.

SEQ ID NOs: 42-69 are sequences of the N30 region of DNA aptamers contemplated for use according to the subject invention.

SEQ ID NO: 70 is a sequence of a DNA aptamer library with a 8-bp stem and 5'-8 nt extension contemplated for use according to the subject invention.

SEQ ID NOs: 71-72 are sequences of non-N30 region of DNA aptamers contemplated for use according to the subject invention.

SEQ ID NOs: 73-77 are cDNA complementary strands for use according to the subject invention.

SEQ ID NOs: 78-82 are sequences of mutant DNA aptamers contemplated for use according to the subject invention.

SEQ ID NO: 83 is a sequence of isolated DNA aptamers with a fluorescent label contemplated for use according to the subject invention.

DETAILED DESCRIPTION OF THE INVENTION

The subject invention provides methods, assays and materials for rapid and specific detection of small molecules in a sample, in particular, in both clinical and field settings. In one embodiment, the method for detecting a small-molecule target in a sample comprises contacting the sample with an aptamer-based sensor selective for the small-molecule target, and detecting the small-molecule target in the sample. Advantageously, the aptamer-based sensor comprises one or more aptamers, according to the subjection, having low nanomolar-micromolar affinity for their targets and minimal response to structurally-similar or dissimilar non-target compounds.

In one embodiment, the detection of the small-molecule target comprises measuring a signal generated upon assembly of the aptamer-target complex. In another embodiment, the method further comprises determining the concentration of the small-molecule target in the sample.

In one embodiment, the sample is a biological sample of a subject. In specific embodiments, the biological sample is selected from blood, serum, plasma, urine, tears, sweat, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized sample, e.g., seized drug sample, for instance, a plant material sample, or a street drug sample seized by law enforcement or school or government officials.

The subject invention provides methods for isolating nucleic acid molecules, e.g., aptamers, which bind to small molecules with high target-affinity and specificity. Advantageously, the methods of the subject invention use appropriate selection strategy and conditions, and include next generation sequencing techniques and bioinformatics.

The subjection invention provides functional nucleic acids that bind to small molecules with high target-affinity and specificity. Such functional nucleic acids, e.g., aptamers, may be isolated from unmodified DNA libraries through SELEX by e.g., library-immobilized SELEX method.

The term "small molecule" or "small-molecule target" used herein extends to any molecule capable of being detected using an aptamer technique. In some embodiments, the small-molecule target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In another embodiment, the small-molecule target may be an infective agent, antigen, toxin, disease biomarker and/or specific metal ion.

In one embodiment, the small molecules according to the subject invention are drug molecules, including fentanyl and its analogs, and salts thereof. In a further embodiment, the drug molecule is selected from fentanyl family, such as Fentanyl, Acetyl fentanyl, and Furanyl fentanyl. Fentanyl analogs may include, but are not limited to Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.

Aptamers

The subject invention provides aptamer-based sensors for use in detecting fentanyl and/or its analogs. The aptamers of the subject invention are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX).

In one embodiment, the aptamer-based sensor comprises one or more aptamers according to the subject invention and, optionally, one or more complimentary nucleic acid sequences. In one embodiment, the aptamer is derived from SEQ ID NO: 1. In a preferred embodiment, the aptamer comprises a nucleic acid sequence selected from 5'-CTTACGAC(N30)GTCGTAAG-3' (SEQ ID NO: 41) and 5'-TGGCAGAACTTACGAC(N30)GTCGTAAG-3' (SEQ ID NO: 70), wherein N30 is selected from SEQ ID NOs: 42-69, as shown below:

| Sequences ID | Sequence (5'-3') |
|---|---|
| SEQ ID NO: 42 | 5'-ACGAGGTGTTTGGACTAAGTTCGGTTTCGG-3' |
| SEQ ID NO: 43 | 5'-GACTGCGTGTGGCCGGTGTGAGGGAGGGTT-3' |
| SEQ ID NO: 44 | 5'-AGCGGGTGTATGTACTAAGTCCGGTTCGGT-3' |
| SEQ ID NO: 45 | 5'-ACTGGCAGGAGGGTCGGGTGTGGGAACGTG-3' |
| SEQ ID NO: 46 | 5'-CAGGCCTACGGAAGCAGCGTCAGCGGGGGG-3' |
| SEQ ID NO: 47 | 5'-TAGTGGAGTAGGGTCGGGTAGTGGGCCTCA-3' |
| SEQ ID NO: 48 | 5'-CACCATGGGAATCGGGTGGCTTGGAGGTGC-3' |
| SEQ ID NO: 49 | 5'-GAGCATCGGTTTTTTCGGTGATGTCTGGGA-3' |
| SEQ ID NO: 50 | 5'-GGAGGTTGGGAAGGAGGGGGAGGCCGGAGA-3' |
| SEQ ID NO: 51 | 5'-GGCAGGTGTTTGCACTAAGTCCGGTATGTC-3' |
| SEQ ID NO: 52 | 5'-CGGTGTGCTCGGGGAAGGGGGGCCCTAGGT-3' |
| SEQ ID NO: 53 | 5'-ATCTGCGTGTGGCCGGTGTGAGGGAGGGAT-3' |
| SEQ ID NO: 54 | 5'-CATGGGTGTTTGCACTAAGTCCGGTTCTTG-3' |
| SEQ ID NO: 55 | 5'-CGGTGTGCTCGGGGAAGGGGGCCCTAGGTG-3' |
| SEQ ID NO: 56 | 5'-ACCGGGATCCAGATGGGTAGTTTGATGTGT-3' |
| SEQ ID NO: 57 | 5'-CGGCGGAAGGCTGGAGGGGTTGGGGGAGGT-3' |
| SEQ ID NO: 58 | 5'-CGGTGGGGAGGCCGGAGTTGGGAACGGGGG-3' |
| SEQ ID NO: 59 | 5'-CGGGATCCTTTGGGACAACCTGGTGGGCAT-3' |
| SEQ ID NO: 60 | 5'-GGGGTACCCGGACAGTGATGTTTGGTGTTC-3' |
| SEQ ID NO: 61 | 5'-GAAGCAACGGGGTTTCGGAGGGCAGGTGTC-3' |
| SEQ ID NO: 62 | 5'-CGGACATGTGATCGGGCAGCTGGGAGTCGG-3' |
| SEQ ID NO: 63 | 5'-GTCGAGGGGTACCCTTTGGCGTTCGTCGAG-3' |
| SEQ ID NO: 64 | 5'-CAGGCTACGTGGGGAGGGTGGGAAGACGG-3' |
| SEQ ID NO: 65 | 5'-ACAGGGTGTGTTGTGCTCAGTGGTGTATGT-3' |
| SEQ ID NO: 66 | 5'-AGGGGTACCCGCGTATAACGTGGCGTTCGT-3' |
| SEQ ID NO: 67 | 5'-GGGGTGGGGCGGCTTCCCATGGGAGGGGT-3' |
| SEQ ID NO: 68 | 5'-GAGCGCGTGTGGCCGGCGTGAGGGAGGTGA-3' |
| SEQ ID NO: 69 | 5'-GGGTGGGGAGGCCCTCTAGTTGGGAACGGT-3' |

In one embodiment, the N30 region serves as the target binding domain.

In specific embodiments, the aptamer-based sensor comprises an aptamer, the aptamer comprising a nucleic acid sequence selected from SEQ ID Nos: 6-36, 83, and 38-39. The complimentary nucleic acid sequence may comprise a sequence of 5'-GTCGTAAG-3' (SEQ ID NO: 40), SEQ ID NO: 37, SEQ ID NOs: 73-77 or SEQ ID No: 2.

The aptamers are identified using the library-immobilized SELEX method where the library is immobilized on a solid support. Preferably, the library is a DNA library comprising at least $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $6 \times 10^{14}$ oligonucleotides. The DNA library comprises more than one library pool. The same or different library pools may be used for fentanyl and/or each of its analogs.

As used herein, the terms "library," "nucleic acid library," "polynucleotide library," and the like, generally refer to a mixture of nucleic acid molecules having variable sequences from which an aptamer is selected for a specific target or target family of small molecules. The nucleic acid molecules of the library have a length ranging from about 5 to about 500 nucleotides, to about 450 nucleotides, to about 400 nucleotides, to about 350 nucleotides, to about 300 nucleotides, to about 250 nucleotides, to about 200 nucleotides, to about 150 nucleotides, to about 100 nucleotides, or to about 50 nucleotides. In some embodiments, the nucleic acid molecules of the library have a length between about 10 nucleotides and about 100 nucleotides, between about 20 nucleotides and about 90 nucleotides, between about 30 nucleotides and about 70 nucleotides, or between about 40 nucleotides and about 60 nucleotides. In certain embodiments, the nucleic acid molecules of the library have a length of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides.

The constituent molecules of a nucleic acid library may be naturally occurring nucleic acids or fragments thereof (e.g., in a cDNA), chemically synthesized nucleic acids, enzymatically synthesized nucleic acids or nucleic acids made using any combination of the aforementioned techniques. Preferably, the nucleic acid library comprises sequences of unmodified nucleic acids.

In some embodiments, each nucleic acid molecule in the library may include one or more fixed (e.g., known) nucleotide sequences 5' to, 3' to, or flanking, the variable region for the purpose of facilitating the enrichment and identification of target aptamers (such as by using PCR, affinity chromatography, or any similar methods used to purify or enrich target nucleic acids).

In a specific embodiment, each library strand comprises a stem-loop structure and 73 nucleotides in length. Such library strand comprises a stem having at least 4, 5, 6, 7, 8, or 9 base-pairs and a randomized loop region comprising 25, 26, 27, 28, 29, 30, 31, 32 or 33 nucleotides.

In a preferred embodiment, the DNA library comprises a sequence of SEQ ID NO: 1 where N represents a random nucleotide and N30 represents the randomized 30 nucleotides. The randomized nucleotides are each independently selected from adenine (A), thymine (T), cytosine (C) and guanine (G). The randomized region comprises the target-binding domain of the aptamer. Preferably, the randomized region is the target-binding domain of the aptamer.

The aptamers isolated according to the subject invention are capable of binding to the small molecule of interest, such as fentanyl, its analogs, and/or salts thereof. The aptamer is an oligonucleotide, such as DNA or RNA molecules and may be single-stranded. In a preferred embodiment, the aptamer is a DNA aptamer.

As used herein, the terms "polynucleotide," "nucleotide," "oligonucleotide," and "nucleic acid" can be used to refer to a nucleic acid comprising DNA, RNA, derivatives thereof, or combinations thereof.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions such as hydrophobic and electrostatic interactions, hydrogen bonding, van der Waals forces, and $\pi$-$\pi$ stacking as well as shape complementarity.

In certain embodiments, the aptamer according to the present invention may comprise at least 20, at least 30, at least 40, at least 50, at least 60, at least 70, or at least 80 nucleotides. The aptamer, preferably, comprises 20 to 200 nucleotides, preferably 25 to 150 nucleotides, more preferably 30 to 100 nucleotides, most preferably, 35 to 60 nucleotides.

In one embodiment, the aptamer according to the present invention may have a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention may have free ends. For example, the 3' and 5' ends may not be ligated to form a loop, although they may be conjugated to other molecules or otherwise modified. The aptamers may adopt a tertiary structure such as a hairpin loop. In some embodiments, the aptamers may be looped. For example, the 5' and 3' ends of the nucleic acid are covalently bonded to form a loop not having any free ends.

In one embodiment, the aptamer according to the subject invention comprises at least one stems, two stems, or three stems. Each stem may be fully or partially complementary. Each stem may comprise the same or different number of nucleotides. Exemplary lengths of each stem may be 1, 2, 3, 4, 5, 6, 7, 8, 9, 10, 11, 12, 13, 14, or 15 base pairs. Other exemplary lengths of each stem may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. A partially complementary stem may comprise more than one wobble base pair.

In one embodiment, the aptamer comprises at least one junction, which is formed when two or more stems meet. In certain embodiments, the junction may be a loop between two stems, or a three-way junction (TWJ). The junction may comprise, for example, 10, 11, 12, 13, 14, 15, 16, 17, 18, 19, 20, 21, 22, 23, 24, 25, 26, 27, 28, 29, or 30 nucleotides. The junction in an aptamer can serve as a binding domain for a small-molecule target.

In one embodiment, the aptamer has at least one hairpin/stem-loop structure. The loop may have a minimum length of, for example, 10, 11, 12, 13, 14, 15, 16, 17, 18, 19, 20, 21, 22, 23, 24, 25, 26, 27, 28, 29, or 30 nucleotides. The loop may have a maximum length of, for example, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. The loop may comprise, for example, 20, 21, 22, 23, 24, 25, 26, 27, 28, 29, 30, 31, 32, 33, 34, 35, 36, 37, 38, 39, or 40 nucleotides. Preferably, the loop comprises 30 nucleotides. The loop region is the target-binding site of the aptamer. In specific embodiments, the aptamer comprises a stem and a loop region. The loop region is specific for binding small molecules of interest.

In one embodiment, the aptamer comprises a nucleic acid sequence selected from SEQ ID NOs: 41 and 70, and sequences sharing at least 50%, 55%, 60%, 65%, 70%, 75%, 80%, 85%, 90%, 95% or 99% identity with SEQ ID NOs: 41 and 70. In a specific embodiment, the aptamer comprises SEQ ID No: 1. In a further embodiment, the N30 sequence of SEQ ID NOs: 1, 41 and 70 comprises a nucleic acid sequence selected from SEQ ID NOs: 42-69 and sequences sharing at least 50%, 55%, 60%, 65%, 70%, 75%, 80%, 85%, 90%, 95% or 99% identity with SEQ ID NOs: 42-69.

In one embodiment, the aptamer comprises a nucleic acid sequence selected from SEQ ID NOs: 41 and 70, wherein the N30 sequence comprises SEQ ID NO: 47, or a sequence sharing at least 50%, 55%, 60%, 65%, 70%, 75%, 80%, 85%, 90%, 95% or 99% identity with SEQ ID NO: 47, and wherein the sequence sharing at least 50%, 55%, 60%, 65%, 70%, 75%, 80%, 85%, 90%, 95% or 99% identity with SEQ ID NO: 47 comprises G at positions 6, 12, 17, and 24, and C at position 15. In a specific embodiment, the sequence sharing at least 50%, 55%, 60%, 65%, 70%, 75%, 80%, 85%, 90%, 95% or 99% identity with SEQ ID NO: 47 does not comprise T at one or more positions selected from positions 6, 12, 17, and 24, and/or A at position 15.

In one embodiment, the aptamer comprises a nucleic acid sequence selected from SEQ ID Nos: 6-36, 83, and 38-39 and sequences sharing at least 50%, 55%, 60%, 65%, 70%, 75%, 80%, 85%, 90%, 95% or 99% identity with SEQ ID Nos: 6-36, 83, and 38-39.

In specific embodiments, the aptamer comprises a nucleic acid sequence selected from SEQ ID Nos: 6-33 and sequences sharing at least 50%, 55%, 60%, 65%, 70%, 75%, 80%, 85%, 90%, 95% or 99% identity with SEQ ID Nos: 6-33. In a specific embodiment, the aptamer consists of a nucleic acid sequence selected from SEQ ID Nos: 6-33

In some embodiments, the aptamer comprises a nucleic acid sequence selected from SEQ ID Nos: 9-14, 17-20, and 28-30, and sequences sharing at least 50%, 55%, 60%, 65%, 70%, 75%, 80%, 85%, 90%, 95% or 99% identity with SEQ ID Nos: 9-14, 17-20, and 28-30. In specific embodiments, the aptamer consists of a nucleic acid sequence selected from SEQ ID Nos: 9-14, 17-20, and 28-30.

In certain embodiments, the aptamer comprises a nucleic acid sequence selected from SEQ ID Nos: 21-23 and 31-33, and sequences sharing at least 50%, 55%, 60%, 65%, 70%, 75%, 80%, 85%, 90%, 95% or 99% identity with SEQ ID Nos: 21-23 and 31-33. In specific embodiments, the aptamer consists of a nucleic acid sequence selected from SEQ ID Nos: 21-23 and 31-33.

In preferred embodiments, the aptamer comprises a nucleic acid sequence selected from SEQ ID Nos: 9-11, 17-19, 22-23, 28-30 and 32, and sequences sharing at least 50%, 55%, 60%, 65%, 70%, 75%, 80%, 85%, 90%, 95% or 99% identity with SEQ ID Nos: 9-11, 17-19, 22-23, 28-30 and 32. In specific embodiments, the aptamer consists of a nucleic acid sequence selected from SEQ ID Nos: 9-11, 17-19, 22-23, 28-30 and 32.

In one embodiment, the aptamer comprises SEQ ID NO: 11, or a sequence sharing at least 50%, 55%, 60%, 65%, 70%, 75%, 80%, 85%, 90%, 95% or 99% identity with SEQ ID NO: 11, and wherein the sequence sharing at least 50%, 55%, 60%, 65%, 70%, 75%, 80%, 85%, 90%, 95% or 99% identity with SEQ ID NO: 11 comprises G at positions 14, 20, 25, and 32, and C at position 23. In a specific embodiment, the sequence sharing at least 50%, 55%, 60/c, 65%, 70%, 75%, 80%, 85%, 90%, 95% or 99% identity with SEQ ID NO: 11 does not comprise T at one or more positions selected from positions 14, 20, 25, and 32, and/or A at position 23.

In one embodiment, the aptamer comprises two or more copies of the nucleic acid sequence selected from SEQ ID Nos: 6-36, 83, and 38-39, and/or sequences sharing at least 50%, 55%, 60%, 65%, 70%, 75%, 80%, 85%, 90%, 95% or 99% identity with SEQ ID Nos: 6-36, 83, and 38-39. In a specific embodiment, the aptamer comprises two or more copies of the nucleic acid sequence selected from SEQ ID Nos: 6-33.

In one embodiment, the aptamer is rich in G. For example, the aptamer comprises at least 10, 11, 12, 13, 14, 15, 16, 17, 18, 19, 20, 21, 22, 23, 24 or 25 Gs. The target-binding domain of the aptamer may comprise at least 5, 6, 7, 8, 9, 10, 11, 12, 13, 14, 15, 16, 17, 18, 19, or 20 Gs. In specific embodiments, the aptamer comprises 10, 11, 12, 13, 14, 15, 16, 17, 18, 19, 20, 21, 22, 23, 24 or 25 Gs. The target-binding domain of the aptamer comprises 5, 6, 7, 8, 9, 10, 11, 12, 13, 14, 15, 16, 17, 18, 19, or 20 Gs.

The aptamer of the present invention may or may not be truncated after isolation. The truncation may occur from 5', 3' or both ends, up to 1, 2, 3, 4, 5, 6, 7, 8, 9, 10, 11, 12, 13, 14, 15, 16, 17, 18, 19 or 20 nucleotides.

The aptamers of the present invention may or may not include chemical modifications. The chemical modifications include a chemical substitution at a sugar position, a phosphate position, and/or a base position of the nucleic acid including, for example, incorporation of a modified nucleotide, incorporation of a capping moiety (e.g., 5' or 3' capping) or a tail moiety, conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include locked nucleic acids (LNA), 2'-amine nucleotides (2'-NH$_2$), 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

In specific embodiments, the aptamer according to the subject invention may be modified by addition, subtraction, and substitution of one or more nucleotides from 5', 3' or both ends or within sequences of the stem region of the aptamer. Advantageously, such addition, subtraction and substitution of one or more nucleotides from 5', 3' or both ends of the aptamer may not affect the binding of the aptamer to small molecule targets. Such addition, subtraction and substitution of one or more nucleotides from 5', 3' or both ends of the aptamer are well established in the art.

The aptamers may or may not be modified by addition of one or more reporter labels (or detectable labels). In some embodiments, the label may be attached to either the 5' or 3' end of the aptamer. The label may also be attached with the backbone or pyrimidine/purine base of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers may or may not comprise a reporter label, such as a fluorescent dye, electroactive tag, nanoparticle (e.g., a gold nanoparticle (AuNP)), a fluorescent dye and quencher pair or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA™, rhodamine, TEXAS RED™, ALEXA FLUOR™ (e.g., ALEXA FLUOR™ 488, ALEXA FLUOR™ 532, ALEXA FLUOR™ 546, ALEXA FLUOR™ 594, ALEXA FLUOR™ 633 and ALEXA FLUOR™ 647), cyanine dye (e.g., CY7™, CY7.5™, CY5™, CY5.5™ and CY3™), TYE™ dye (e.g., TYE™ 563, TYE™ 665, and TYE™ 705), ATTO™ dye (e.g., ATTO™ 594 and ATTO™ 633), Hexachlorofluorescein, FAM (6-carboxyfluorescein), BODIPY FL, OliGreen, 40,6-diamidino-2-phenylindol (DAPI), Hoechst 33,258, malachite green (MG), and FITC. The nanoparticle can be an upconversion nanoparticle. Electroactive tag can be a methylene blue or ferrocene molecule. In some embodiments, the fluorophore is selected from the group consisting of fluorophores that emit a blue, green, near red or far red fluorescence.

In some embodiments, the aptamer may bind to a complementary sequence. The aptamer and the complementary sequence may be labeled by a fluorescent dye and quencher pair. In certain embodiments, a fluorophore is conjugated at one end of the aptamer and a quencher at one end of the complementary sequence. In the absence of its target, the complementary sequence binds to the aptamer, thereby positioning the fluorophore close to the quencher. Target binding to the aptamer displaces the complementary sequence, resulting in the separation of the fluorophore and the quencher. The resulting recovery of the fluorescence signal directly reflects the extent of the binding and can be used for detection and quantitative measurement of the target concentration. The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In some embodiments, the fluorophore is at a location of, for example, 1st, 2nd, 3rd, 4th, 5th, 6th, 7th, 8th, 9th, or 10th nucleotide from either 5' end or 3' end of the aptamer. The quencher is at a location of, for example, 1st, 2nd, 3rd, 4th, 5th, 6th, 7th, 8th, 9th, or 10th nucleotide from either 3' end or 5' end of the complementary sequence.

In preferred embodiments, the location of the fluorophore and quencher is such that the proximity of the fluorophore and quencher in a complementary sequence binding conformation provide maximal quenching and the fluorophore and quencher in a separated conformation provide maximal fluorescence of the fluorophore. For optimized detection of fluorescence changes that allows utilization of aptamers for target detection, it is desirable that the fluorescence in the quenched conformation is as low as possible and the fluorescence in the unquenched conformation is as high as possible combined with the most rapid interconversion from one conformation to the other.

In one embodiment, the aptamer-based sensor comprises a fluorophore-modified aptamer and quencher-modified cDNA pair. The aptamer is one of the aptamers of the subject invention. In one embodiment, the quencher-modified cDNA comprises a nucleic acid sequence that is complementary or contains a single mismatch to the non-N30 sequence of SEQ ID NOs: 1, 41 and 70. In a specific embodiment, the non-N30 sequence comprises SEQ ID NO: 40, 5'-CTTACGAC-3' (SEQ ID NO: 71) or 5'-TGGCAGAACTTACGAC-3' (SEQ ID NO: 72). In a preferred embodiment, the cDNA is modified with, for example, a quencher. In some embodiments, the quencher-modified cDNA comprises SEQ ID NO: 2, 37, 5'-TCGTAAGTTCTGCC-3' (SEQ ID NO: 73), 5'-GTCGTAAGTTCTGC-3' (SEQ ID NO: 74), 5'-GTTGTAAGTTCTGCC-3' (5'-GT cDNA, SEQ ID NO: 75), 5'-GTCGTAGGTTCTGCC-3' (m-GT cDNA, SEQ ID NO: 76), or 5'-GTCGTAAGTTTTGCC-3' (3'-GT cDNA, SEQ ID NO: 77).

In specific embodiments, the aptamer specifically recognizes fentanyl, its analogs, and/or salts thereof. The aptamer can specifically bind to one or more, for example, Fentanyl, Acetyl fentanyl, and Furanyl fentanyl with nanomolar-micromolar dissociation constant and does not bind to, for example, lorazepam, noscapine, papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, mannitol, or lactose.

In one embodiment, the aptamer binds to the small molecule with a dissociation constant of, for example, about 10 nM, about 50 nM, about 100 nM, about 150 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1 µM, about 2 µM, about 3 µM, about 4 µM, about 5 µM, about 6 µM, about 7 µM, about 8 µM, about 9 µM, or about 10 µM.

Method of Using the Aptamer

The aptamers according to the subject invention have high binding affinity and specificity for their targets, which enables their use for sensitive detection of fentanyl, its analogs, and/or salts thereof for analytical purposes.

The subject invention provides aptamer-based sensors for rapid, sensitive, and specific detection of small-molecule targets in a sample. The aptamer-based sensor comprises one or more aptamers, according to the subject invention, that can bind to fentanyl, its analogs, and/or salts thereof. The subject invention also provides methods of using the aptamer-based sensor for detecting one or more small-molecule targets in a complex sample.

In one embodiment, the method for detecting a small-molecule target comprises contacting the sample with an aptamer-based sensor selective for a small-molecule target, wherein the aptamer-based sensor comprises one or more aptamers of the subject invention and detecting the small-molecule target in the sample, wherein the detection of the small-molecule target comprises measuring a signal generated upon binding of the small-molecule targets to the binding domain of the aptamer.

In one embodiment, the method further comprises determining the concentration of the small-molecule target in the sample. The determination comprises comparing the signal (e.g., fluorescence) generated upon binding of the small-molecule target with the aptamer-based sensor with a standard curve.

In some embodiments, the aptamer-based sensor comprises one or more aptamers selected from SEQ ID Nos: 6-36, and 38-39 and sequences sharing at least 50%, 55%, 60%, 65%, 70%, 75%, 80%, 85%, 90%, 95% or 99% identity with SEQ ID Nos: 6-36, and 38-39. Preferably, the aptamer-based sensor comprises one or more aptamers selected from SEQ ID Nos: 9-14, 17-20, and 28-30, and sequences sharing at least 50%, 55%, 60%, 65%, 70%, 75%, 80%, 85%, 90%, 95% or 99% identity with SEQ ID Nos: 9-14, 17-20, and 28-30. More preferably, the aptamer-based sensor comprises one or more aptamers selected from SEQ ID Nos: 21-23 and 31-33, and sequences sharing at least 50%, 55%, 60%, 65%, 70%, 75%, 80%, 85%, 90%, 95% or 99% identity with SEQ ID Nos: 21-23 and 31-33. Most preferably, the aptamer-based sensor comprises one or more aptamers selected from SEQ ID Nos: 9-11, 17-19, 22-23, 28-30 and 32, and sequences sharing at least 50%, 55%, 60%, 65%, 70%, 75%, 80%, 85%, 90%, 95% or 99% identity with SEQ ID Nos: 9-11, 17-19, 22-23, 28-30 and 32.

In one embodiment, the aptamer-based sensor comprises at one, two, or three aptamer sequences. In a specific embodiment, the aptamer-based sensor is a triple-aptamer sensor that comprises three aptamers. Preferably, the triple-aptamer sensor comprises three aptamers, for example, F4-FAM, F13-FAM, and F27-FAM.

In one embodiment, the aptamer-based sensor further comprises a nucleic acid sequence that is complimentary to up to 8, 9, 10, 11, 12, 13, 14, or 15 nucleotides from the 5' or 3' end of the aptamer of the subject invention. The complimentary nucleic acid sequence comprises at least 5, 6, 7, 8, 9, 10, 11, 12, 13, 14, or 15 nucleotides. Exemplary lengths of each stem may be 10, 11, 12, 13, 14, or 15 nucleotides.

In specific embodiments, the aptamer-based sensor is labeled with a fluorophore-quencher pair wherein the aptamer comprises a fluorophore at the 5' or 3' end while the complimentary nucleic acid sequence comprises a quencher at the 3' or 5' end. In a preferred embodiment, the fluorophore is fluorescein (e.g., FAM) at 5'-end, and the quencher is a dabcyl quencher at the 3'-end.

In such strand-displacement fluorescence assay, the complimentary strand labelled with a quencher is initially associated with the aptamer labeled with a fluorophore so that the fluorophore is in the quenched conformation. In the presence of a target of the aptamer, the binding of the target to the target-binding domain of the aptamer may induce a conformation change to displace the complimentary sequence from the aptamer, causing the fluorophore to adopt an unquenched conformation and resulting in a change in, for example, its fluorescence. Advantageously, the assay has excellent specificity because the aptamer does not cross-react to other interferents.

In some embodiments, the fluorophore may be used at a concentration ranging from about 0.01 µM to about 100 µM, from about 0.1 µM to about 90 µM, from about 0.1 µM to about 80 µM, from about 0.1 µM to about 70 µM, from about 1 µM to about 60 µM, from about 1 µM to about 50 µM, from about 1 µM to about 40 µM, from about 1 µM to about 30 µM, from about 1 µM to about 20 µM, or from about 1 µM to about 10 µM.

In one embodiment, the method further comprises determining the concentration of the small-molecule target in the sample. The determination can comprise comparing the signal generated upon target binding with a standard curve of such signal. For example, the determination comprises comparing the fluorescence signal generated upon binding of aptamer-target complex with a standard curve of the fluorescence intensity of fluorescein. The fluorescence intensity read-out can be quantified in seconds by, for example, a microplate-reader or portable photometer, allowing for high-throughput or on-site detection, respectively.

In one embodiment, the method for rapid, sensitive and specific detection of fentanyl, its analogs, and/or salts thereof in a sample comprises contacting the sample with a aptamer-based sensor selective for fentanyl and its analogs, and salts thereof, wherein the aptamer-based sensor comprises one or more aptamers of the subject invention, and, optionally, a complimentary nucleic acid sequence and detecting whether a signal change occurs, the signal being a change in fluorescence intensity, the signal change being indicative of the presence of the fentanyl, its analogs, and/or salts thereof in the sample. Preferably, fentanyl analogs are selected from Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.

Other forms of detection of fentanyl, analogs and salts thereof may also utilize the aptamers of the subject invention in, for example, electrochemical sensors, gold nanoparticle assays, enzyme linked aptamer sorbent assays (ELASA), microplate/well assays, lateral flow assays and/or any other appropriate form of detection.

In some embodiments, the aptamer according to the subject invention may be used at a concentration from about 1 nM to about 10 mM, about 10 nM to about 5 mM, about 20 nM to about 2 mM, about 50 nM to about 1 mM, about 100 nM to about 500 µM, about 200 nM to about 200 µM, about 500 nM to about 100 µM, about 1 µM to about 50 µM, from about 1 µM to about 40 µM, from about 1 µM to about 30 µM, from about 1 µM to about 20 µM, from about 1 µM to about 10 µM, from about 2 µM to about 9 µM, from about 2 µM to about 8 µM, from about 2 µM to about 7 µM, from about 3 µM to about 6 µM, from about 4 µM to about 6 µM, and from about 5 µM to about 6 µM. In specific embodiments, the aptamer according to the subject invention may be used at a concentration of 1 nM, 10 nM, nM, 25 nM, 50 nM, 100 nM, 200 nM, 500 nM, 1 µM, 2 µM, 3 µM, 4 µM, or 5 µM.

In one embodiment, the method according to the subject invention can achieve superior sensitivity for target detection at low micromolar or nanomolar concentration, for example, as low as about 200 µM, about 150 µM, about 100 µM, about 10 µM, about 5 µM, about 1 µM, about 500 nM, about 200 nM, about 100 nM, about 50 nM, about 20 nM, about nM, about 5 nM, or about 1 nM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, about 25 minutes to about 40 minutes, about 5 minutes to about 40 minutes, about 5 minutes to about 30 minutes, about 5 minutes to about 25 minutes, about 5 minutes to about 20 minutes, or about 5 minutes to about 15 minutes.

In one embodiment, the method can be completed in about 5 minutes, about 10 minutes, about 15 minutes, about 20 minutes, about 25 minutes, about 30 minutes, about 35 minutes, about 40 minutes, about 45 minutes, or about 50 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides an electrochemical aptamer-based (E-AB) sensor and a method for rapid and sensitive detection of one or more small-molecule targets in a sample by using the E-AB sensor.

In one embodiment, the method for rapid and sensitive detection of one or more small-molecule targets in a sample by incorporating a structure-switching aptamer into the E-AB sensor, which has demonstrated target-induced conformational changes within the aptamer and has achieved excellent sensor performance. The method comprises contacting the sample with the E-AB sensor, and detecting one or more small-molecule targets in the sample, wherein the detection of the small-molecule target comprises measuring a signal generated from a signal reporter. In a further embodiment, the detection of the small-molecule target comprises measuring a signal generated upon binding of the small-molecule target with the E-AB sensor, wherein the signal is an increase in current.

In one embodiment, the E-AB sensor comprises a structure-switching aptamer and an electrode, wherein the structure-switching aptamer is labeled with a redox tag at one end and a functional group at the other end, and wherein the structure-switching aptamer is conjugated to the surface of the electrode via the functional group. The functional groups include, but are not limited to, thiol, sulfide, disulfide, amide, ester, alkenyl, alkynyl, carbonyl, aldehyde, carboxylate, carboxyl, and carbonate ester groups. Preferably, the functional group is thiol, and the redox tag is a methylene blue (MB) redox tag, which may label the aptamer at the 5' end, 3' end, and pyrimidine/purine base within the aptamer via a linker having 1-10 carbons, preferably, a linker having 6 or 7 carbons.

In a specific embodiment, the structure-switching aptamer comprises a nucleic acid sequence selected from SEQ ID NOs: 42-69.

In the absence of a target, the structure-switching aptamer is primarily unfolded, prohibiting electron transfer from the redox tag to the electrode. In the presence of a target, the structure-switching aptamer undergoes a target-induced conformational change that brings the redox tag close to the electrode surface, facilitating efficient electron transfer and resulting in an increase in current within seconds.

In one embodiment, the electrode is made of an electroconductive material, for example, gold, silver, or platinum. The electrode may have any shape suitable for the E-AB sensor. Exemplary shapes of electrode include, but are not limited to, wire, flake, rod, sheet, plate, disk, and paper-based electrodes. The electrode may have a size ranging from about 100 nm to about 50 mm, from about 500 nm to about 10 mm, from about 1 mm to about 5 mm. In a specific embodiment, the electrode has a diameter about 3 mm.

In certain embodiments, the aptamer is immobilized on the electrode of the E-AB sensor at a density ranging from about $1\times10^{10}$ to about $1\times10^{15}$, about $5\times10^{10}$ to about $5\times10^{14}$, about $1\times10^{11}$ to about $1\times10^{14}$, about $5\times10^{11}$ to about $5\times10^{13}$, about $1\times10^{12}$ to about $5\times10^{13}$, and about $1\times10^{12}$ to about $1\times10^{13}$ molecules/cm$^2$. In specific embodiment, the aptamer is immobilized on the electrode at a density of $1\times10^{12}$, $1.5\times10^{12}$, $1.57\times10^{12}$, $2.92\times10^{12}$, $3\times10^{12}$, $3.3\times10^{12}$, $3.74\times10^{12}$, $5\times10^{12}$, $7.3\times10^{12}$, or $12\times10^{12}$ molecules/cm$^2$.

In one embodiment, the E-AB sensor further comprises a backfiller to fill vacant areas on the electrode surface. The backfiller includes 6-mercapto-1-hexanol (MCH), 1-hexanethiol, thiol-PEG, dithiothreitol (DTT), and/or a combination thereof. The backfiller is immobilized on the surface of the electrode, for example, via thiol-gold chemistry.

In certain embodiments, the backfiller may be used at concentrations between about 10 µM to about 50 mM, from about 100 µM to about 40 mM, from about 200 µM to about 30 mM, from about 500 µM to about 20 mM, from about 1 mM to about 10 mM, from about 2 mM to about 9 mM, and from about 2 mM to about 5 mM. In a preferred embodiment, the backfiller is used, either alone or in combination, at a concentration of 1 mM, 2 mM, 3 mM, 4 mM, or 5 mM.

In a specific embodiment, the E-AB sensor comprises a structure-switching aptamer, and an electrode, wherein the electrode is a gold electrode (e.g., gold disc) or paper-based electrode, wherein the structure-switching aptamer is labeled with a 5' thiol and a 3' methylene blue (MB) redox tag, and conjugated to the gold electrode surface via thiol-gold chemistry.

In specific embodiments, the E-AB sensor is a three-electrode system comprising a working electrode, a reference electrode and a counter electrode, wherein the working electrode is an aptamer-modified electrode that is functionalized with a structure-switching aptamer of the subject invention. Preferably, the structure-switching aptamer is labeled with a 5' thiol and a 3' methylene blue (MB) redox tag and conjugated to the working electrode surface via thiol-gold chemistry.

In one embodiment, the method further comprises determining the concentration of the small-molecule target in the sample. The determination comprises comparing the current generated upon binding of the small-molecule target with the E-AB sensor with a standard curve. The read-out can be quantified in seconds by, for example, a potentiostat. Thus, the current measured upon binding of the small-molecule target with the E-AB sensor is indicative of the presence of the small-molecule target in such sample.

In one embodiment, the method according to the subject invention can be used to detect one or more target molecules selected from fentanyl, analogs and salts thereof in a sample. The method comprises contacting the sample with an E-AB sensor, wherein the E-AB sensor comprises a structure-switching aptamer selective for fentanyl, analogs, and/or salts thereof, and the structure-switching aptamer is conjugated to the surface of a gold electrode; and detecting one or more fentanyl, analogs, and/or salts thereof in the sample, wherein the detection comprises measuring a current generated upon binding of fentanyl, its analogs, and/or salts thereof with the E-AB sensor. Advantageously, this method using E-AB sensor can detect fentanyl, its analogs, and/or salts thereof in a sample within 10 seconds of the reaction.

In one embodiment, the E-AB sensor is used to detect fentanyl, its analogs, and/or salts thereof in a buffer solution comprising at least one salt containing, for example, $Mg^{2+}$ and/or $Na^+$. The salt may be, for example, $MgCl_2$ and/or NaCl. The salt may be used at the physiological concentration or any concentrations suitable for maintaining the function and binding affinity of isolated aptamers and the E-AB sensor.

In a specific embodiment, the 5'-truncated version of the structure-switching aptamer (e.g., F13-39 (SEQ ID NO: 38)) is modified with a 5' thiol and a 3' methylene blue redox tag, i.e., F13-39-MB (SEQ ID NO: 39). The thiol group may be linked to the 5' end of the aptamer via a first linker and the methylene blue redox tag may be linked to the 3' end of the aptamer via a second linker. The first and second linkers may be different or identical. Each of the first and second linkers independently comprises 1-10 carbons. Preferably, each of the first and second linkers independently comprises 2-8 carbons. More preferably, the first linker is a 6 or 7-carbon linker (e.g., —$(CH_2)_6$—) and the second linker is a 10-atom linker (i.e., —$(CH_2)_6$—(NHCO)—$(CH_2)_2$).

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain.

In one embodiment, the subject invention also further provides a kit for detecting fentanyl, analogs and/or salts thereof, the kit comprising the aptamer-based sensor according to the subject invention and instructions for using such aptamer-based sensor to detect fentanyl, analogs, and/or salts thereof.

The subject invention encompasses the use of sequences having a degree of sequence identity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Experimental Section

Reagents.

Exonuclease III (*E. coli*) (100 U/µL) and Exonuclease I (*E. coli*) (20 U/µL) were purchased from New England Biolabs. Fentanyl (hydrochloride), Acetyl fentanyl (hydrochloride), Furanyl fentanyl (hydrochloride), Acrylfentanyl (hydrochloride), Butyryl fentanyl (hydrochloride), Valeryl fentanyl (hydrochloride), Cyclopropyl fentanyl (hydrochloride), Methoxyacetyl fentanyl (hydrochloride), Remifentanil (hydrochloride), alpha-methyl Thiofentanyl (hydrochloride), o-methyl Furanyl fentanyl (hydrochloride), p-Fluoroisobutyryl fentanyl (hydrochloride), heroin (hydrochloride), morphine (sulfate), codeine (phosphate), and lorazepam were purchased from Cayman Chemicals. Cis-3-methyl Fentanyl (hydrochloride), p-methoxy Furanyl fentanyl (hydrochloride), p-Fluoro fentanyl (hydrochloride), and p-methoxy Butyryl fentanyl (hydrochloride) were provided as drug standards by the DEA's southwest laboratory. Noscapine (hydrochloride) was purchased from Tokyo Chemical Industry. Papaverine (hydrochloride) was purchased from Acros Organic. Lidocaine was purchased from Alfa Aesar. SYBR Gold was purchased from Invitrogen. Formamide was purchased from Fisher Scientific. Cocaine (hydrochloride), (+)-pseudoephedrine (hydrochloride), (+)-methamphetamine (hydrochloride), chlorpromazine (hydrochloride), procaine (hydrochloride), quinine (sulfate), acetaminophen, benzocaine, diphenhydramine (hydrochloride), mannitol, lactose, caffeine and all other chemicals were purchased from Sigma Aldrich unless otherwise noted. Streptavidin-modified agarose beads, ExoSAP-IT Express PCR Purification Kit, and Nunc 384-well black plate were purchased from Thermo Fisher Scientific. 800 µL microgravity columns were purchased from Bio-Rad. GoTaq Hot Start Colorless Master Mix was purchased from Promega. 3 kDa cut-off spin filters were purchased from Millipore. All unmodified oligonucleotides were purchased from Integrated DNA Technologies with standard desalting purification. Fluorophore or quencher modified DNA was purchased from Integrated DNA technologies with HPLC purification. All oligonucleotides were dissolved in PCR-quality water and their concentrations were measured using a spectrophotometer (NanoDrop 2000). Thiolated methylene blue modified DNA for electrochemical aptamer-based sensing was purchased from LGC Biosearch Technologies with dual-HPLC purification and dissolved in TE Buffer (10 mM Tris-HCl with 1 mM ethylenediaminetetraacetic acid, pH 8.0). The DNA sequences employed in this work are listed below:

TABLE 1

DNA sequences used in this work.

| Sequences ID | Sequence (5'-3') |
|---|---|
| Random library (SEQ ID NO: 1) | CGAGCATAGGCAGAACTTACGAC(N30)GTCGTAAGAGCGAGTCATTC |
| Bio-cDNA (SEQ ID NO: 2) | TTTTTGTCGTAAGTTCTGCCATTTT-/3BioTEG/ |
| Forward primer (SEQ ID NO: 3) | CGAGCATAGGCAGAACTTAC |
| Biotinylated-reverse primer (SEQ ID NO: 4) | /3BioTEG/-GAATGACTCGCTCTTACGAC |
| Reverse primer (SEQ ID NO: 5) | GAATGACTCGCTCTTACGAC |
| F1 (SEQ ID NO: 6) | CTTACGACACGAGGTGTTTGGACTAAGTTCGGTTTCGGGTCGTAAG |
| F2 (SEQ ID NO: 7) | CTTACGACGACTGCGTGTGGCCGGTGTGAGGGAGGGTTGTCGTAAG |
| F3 (SEQ ID NO: 8) | CTTACGACAGCGGGTGTATGTACTAAGTCCGGTTCGGTGTCGTAAG |
| F4 (SEQ ID NO: 9) | CTTACGACACTGGCAGGAGGGTCGGGTGTGGAACGTGGTCGTAAG |
| F5 (SEQ ID NO: 10) | CTTACGACCAGGCCTACGGAAGCAGCGTCAGCGGGGGGTCGTAAG |
| F6 (SEQ ID NO: 11) | CTTACGACTAGTGGAGTAGGGTCGGGTAGTGGGCCTCAGTCGTAAG |
| F7 (SEQ ID NO: 12) | CTTACGACCACCATGGGAATCGGGTGGCTTGGAGGTGCGTCGTAAG |
| F8 (SEQ ID NO: 13) | CTTACGACGAGCATCGGTTTTTTCGGTGATGTCTGGGAGTCGTAAG |
| F9 (SEQ ID NO: 14) | CTTACGACGGAGGTTGGGAAGGAGGGGAGGCCGGAGAGTCGTAAG |
| F10 (SEQ ID NO: 15) | CTTACGACGGCAGGTGTTTGCACTAAGTCCGGTATGTCGTCGTAAG |
| F11 (SEQ ID NO: 16) | CTTACGACCGGTGTGCTCGGGGAAGGGGGCCCTAGGTGTCGTAAG |
| F12 (SEQ ID NO: 17) | CTTACGACATCTGCGTGTGGCCGGTGTGAGGGAGGGATGTCGTAAG |
| F13 (SEQ ID NO: 18) | CTTACGACCATGGGTGTTTGCACTAAGTCCGGTTCTTGGTCGTAAG |
| F14 (SEQ ID NO: 19) | CTTACGACCGGTGTGCTCGGGGAAGGGGGCCCTAGGTGGTCGTAAG |

TABLE 1-continued

DNA sequences used in this work.

| Sequences ID | Sequence (5'-3') |
|---|---|
| F15 (SEQ ID NO: 20) | CTTACGACACCGGGATCCAGATGGGTAGTT TGATGTGTGTCGTAAG |
| F16 (SEQ ID NO: 21) | CTTACGACCGGCGGAAGGCTGGAGGGGTTG GGGGAGGTGTCGTAAG |
| F17 (SEQ ID NO: 22) | CTTACGACCGGTGGGGAGGCCGGAGTTGGG AACGGGGGGTCGTAAG |
| F18 (SEQ ID NO: 23) | CTTACGACCGGGATCCTTTGGGACAACCTG GTGGGCATGTCGTAAG |
| F19 (SEQ ID NO: 24) | CTTACGACGGGGTACCCGGACAGTGATGTT TGGTGTTCGTCGTAAG |
| F20 (SEQ ID NO: 25) | CTTACGACGAAGCAACGGGGTTTCGGAGGG CAGGTGTCGTCGTAAG |
| F21 (SEQ ID NO: 26) | CTTACGACCGGACATGTGATCGGGCAGCTG GGAGTCGGGTCGTAAG |
| F22 (SEQ ID NO: 27) | CTTACGACGTCGAGGGGTACCCTTTGGCGT TCGTCGAGGTCGTAAG |
| F23 (SEQ ID NO: 28) | CTTACGACCAGGCTACGTGGGGAGGGTGG GAAGACGGGTCGTAAG |
| F24 (SEQ ID NO: 29) | CTTACGACACAGGGTGTGTTGTGCTCAGTG GTGTATGTCGTAAG |
| F25 (SEQ ID NO: 30) | CTTACGACAGGGGTACCCGCGTATAACGTG GCGTTCGTGTCGTAAG |
| F26 (SEQ ID NO: 31) | CTTACGACGGGGTGGGGCGGCTTCCCATG GGAGGGGTGTCGTAAG |
| F27 (SEQ ID NO: 32) | CTTACGACGAGCGCGTGTGGCCGGCGTGAG GGAGGTGAGTCGTAAG |
| F28 (SEQ ID NO: 33) | CTTACGACGGGTGGGGAGGCCCTCTAGTTG GGAACGGTGTCGTAAG |
| F4-FAM (SEQ ID NO: 34) | /FAM/TGGCAGAACTTACGACACTGGCAGG AGGGTCGGGTGTGGGAACGTGGTCGTAAG |
| F13-FAM (SEQ ID NO: 35) | /FAM/TGGCAGAACTTACGACCATGGGTGT TTGCACTAAGTCCGGTTCTTGGTCGTAAG |
| F27-FAM (SEQ ID NO: 36) | /FAM/TGGCAGAACTTACGACGAGCGCGTG TGGCCGGCGTGAGGGAGGTGAGTCGTAAG |
| cDNA-Dab (SEQ ID NO: 37) | GTCGTAAGTTCTGCC/Dab/ |
| F13-39 (SEQ ID NO: 38) | CTTACGACCATGGGTGTTTGCACTAAGTCC GGTTCTTGG |
| F13-39-MB (SEQ ID NO: 39) | /Thio1C6/CCATGGGTGTTTGCACTAAGT CCGGTTCTTGG/MB/ |
| F6-FAM (SEQ ID NO: 83) | /FAM/TGGCAGAACTTACGACTAGTGGAGT AGGGTCGGGTAGTGGGCCTCAGTCGTAAG |
| cDNA (SEQ ID NO: 84) | GTCGTAAGTTCTGCC | a. N30 represents 30 random nucleotides;
b. /3BioTEG/ represents biotin tag;
c. /FAM/ represents fluorescein tag
d. /Dab/ represents dabcyl quencher tag;
e. /Thio1C6/ represents thiol group with six-carbon spacer
f. /MB/ represents methylene blue redox tag SELEX Procedure The isolation of aptamers was carried out following a previously reported library-immobilized SELEX protocol. The initial single-stranded DNA library used for each pool consisted of $6 \times 10^{14}$ oligonucleotides. The random library pool is composed of a randomized 30-nt loop flanked by an 8-nt stem-forming constant region and two PCR primer-binding sites. Prior to each round of selection, the library/pool was mixed with biotinylated complementary strands (bio-cDNA) at a molar ratio of 1:5 in selection buffer (10 mM Tris-HCl, 20 mM NaCl, 0.5 mM $MgCl_2$, 1% MeOH, pH 7.4), heated at 95° C. for 10 mins and cooled to room temperature over 20 mins to ensure hybridization between the library and bio-cDNA. A micro-gravity column was prepared with 250 µL streptavidin coated agarose beads (15-28 µg biotin/mL), followed by three washes of 250 µL selection buffer. 250 µL of the hybridized bio-cDNA-library solution was flowed through the column three times to immobilize the bio-cDNA-library duplex onto the agarose beads. The column was subsequently washed ten times with 250 µL selection buffer and subjected to additional 250 µL washing steps with selection buffer or counter target mixtures according to the selection strategy and conditions listed in tables 2, 3, or 4. The column was then washed three times with 250 µL of the target (Fentanyl, Acetyl fentanyl, or Furanyl fentanyl) dissolved in selection buffer. Library molecules that bound to the target undergo a conformational change, which frees the library molecules from the agarose beads into solution. The eluent from target washing steps was collected and concentrated to a final volume of 100 µL using a 3 kDa cut-off centrifugal filter. The concentrated pool was then mixed with 600 µL of 2× GoTaq Hot Start Colorless Master Mix with 2 µM forward primer and 2 µM biotinylated reverse primer and diluted to a final volume of 1200 µL with PCR-quality water for subsequent PCR. Amplification was performed using a Bio-Rad C1000 thermal cycler with the following conditions: 2 min at 95° C.; 11 cycles of 95° C. for 15 s, 58° C. for 30 s and 72° C. for 45 s, ended with 5 min at 72° C. The optimal amplification cycles to regenerate the library without generating PCR by-products was determined using pilot PCR. Amplification of the enriched pool was confirmed using 3% agarose gel electrophoresis. Following PCR amplification, a micro-gravity column was prepared as previously described for single-stranded DNA generation. The amplified pool was then flowed through the column three times to conjugate the biotinylated double-stranded PCR products to the beads. The column was then washed six times with 250 μL separation buffer (10 mM Tris-HCl, 20 mM NaCl, pH 7.4). The column was capped followed by addition of 300 μL 0.2 M NaOH and incubated for 10 mins. Library sequences are then denatured from their biotinylated complementary strands and dissociated into the solution. An additional 100 μL 0.2 M NaOH was added to elute residual library strands from the column. The eluents were combined and neutralized using 1 M HCl followed by concentration with a 3 kDa cut-off centrifugation filter to a final volume of ~100 μL.

Gel Elution Assay for Measuring Binding Affinity and Specificity of Enriched Pools.

The affinity and specificity of the round 11 fentanyl pool, round 10 acetyl fentanyl pool, and round 10 furanyl fentanyl pool were determined using a previously reported gel elution assay. Specifically, 0.4 μM of the enriched library was incubated with 2 μM of bio-cDNA in 160 μL of selection buffer. The mixture was heated at 95° C. for 10 mins and slowly cooled to room temperature over 20 mins. Streptavidin coated agarose beads (160 μL) were added into a micro-gravity column and washed five times with 250 μL selection buffer, after which, they were transferred to a 1.5 mL microcentrifuge tube. The bio-cDNA-library complex was then added to the beads and allowed to incubate on an end-over-end rotator for 30 mins. Following incubation, the beads were centrifuged, and the supernatant was discarded. To remove non-specific eluting library strands, the beads were washed five times by adding 800 μL of selection buffer, incubating on an end-over-end rotator for 5 mins, followed by centrifugation and removal of the supernatant. The volume of the library-immobilized beads was adjusted to 960 μL using selection buffer and 100 μL of the final solution was aliquoted into nine tubes, afterwards, the tubes were centrifuged, and 80 μL of supernatant was removed. 50 μL of the selection target (0, 2.5, 5, 10, 25, 50, 100, 250, or 500 μM) was added to each tube and allowed to rotate on an end-over-end rotator for 60 mins, after which, the beads were centrifuged and 40 μL of the supernatant containing library strands eluted by the target was collected. The target-eluted aptamer solution was analyzed via denaturing polyacrylamide gel electrophoresis and measured their concentrations using a standard library solution. A calibration curve was created by plotting the fraction of eluted strands against the target concentration and fit using a Langmuir equation. The same protocol was used with the appropriately scaled volumes to determine the cross-reactivity and specificity of the enriched pool against fentanyl, acetyl fentanyl, furanyl fentanyl, lorazepam, noscapine, papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, mannitol, and lactose.

High Throughput Sequencing

High-throughput sequencing (HTS) for rounds 9 & 11 fentanyl pools, rounds 8 & 10 acetyl fentanyl pools, and rounds 7 & 10 furanyl fentanyl pools, was performed using Ion Torrent Sequencing. To prepare samples for sequencing, the library pool (Final concentration: 10 nM) was mixed with 2× GoTaq Hot Start Colorless Master Mix (Final concentration: 1×), forward primer (Final concentration: 1 μM) and reverse primer (Final concentration: 1 μM) and diluted with PCR-quality water to a final volume of 50 μL. Nine cycles of PCR was performed using the PCR conditions described in the SELEX procedure. Then 40 μl of PCR product was added into 16 μl of ExoSAP-IT reagent in an ice bath. The mixture was then incubated at 37° C. for 15 min to degrade remaining primers and dNTP's, followed by incubation at 80° C. for 15 min to inactivate the ExoSAP-IT magnet, after which, the samples were submitted to FIU's DNA Core Facility for HTS. HTS was performed using an Ion Personal Genome Machine System with an Ion 318 v2 chip (Thermo Fisher Scientific). Upon obtaining the sequencing data, the primer sequences were trimmed by cutadapt, and the population of sequences from each pool were calculated using FASTAptamer.

Screening of Aptamer Binding Affinity and Specificity Using an Exonuclease-Digestion Assay.

Aptamer digestion experiments were performed using the following procedure unless otherwise specified. A 1 μL solution of 50 μM aptamer was added into 29 μL of Tris-HCl buffer (pH 7.4) and heated to 95° C. for 10 mins and immediately cooled on ice, after which, salts, methanol, and BSA were added to the mixture (Final concentrations: 10 mM Tris-HCl, 20 mM NaCl, 0.5 mM $MgCl_2$, 1% MeOH, 0.1 mg/mL BSA, pH 7.4). 5 μL of 1 mM fentanyl, its analogs, or interferent molecules was added to the reaction mixture and incubated in a thermal cycler (C1000 touch, Bio-Rad) at 25° C. for 60 min, after which 5 μL of the enzymes (Final concentrations: 0.025 U/μL Exo III and 0.05 U/μL Exo I) was added to each reaction mixture. For all experiments, 5 μL of sample was collected at various time points and loaded directly into the wells of a Nunc 384-well black plate containing 25 μL of quench solution (Final concentrations: 10 mM Tris-HCl, 12.5% formamide, 10 mM ethylenediaminetetraacetic acid, 1×SYBR Gold). Fluorescence intensity at 537 nm was recorded using a Tecan microplate reader (Tecan Infinite M1000 PRO, Switzerland) with a 495 nm excitation wavelength.

Analysis of Aptamer Digestion Rates.

The time-course of aptamer digestion was fitted using first order reaction kinetics as described by equation 1:

$$F_t = F_0 2^{-\frac{t}{t_{1/2}}} + C \quad (1)$$

Where t is the time in minutes, $F_t$ is the fluorescence intensity of SYBR Gold at time 't', $F_0$ is the max fluorescence intensity of the inhibition product, C is a constant to correct for background fluorescence, and $t_{1/2}$ is the half-life of the reaction in minutes. During fitting the first point was excluded and bounds were placed on $F_0$ and C, allowing these values to vary between 75-100% and 0-5% of the fluorescence intensity of the undigested aptamer, respectively. Error bars represent the standard error of fitting obtained using Origin 2019 software. The $t_{1/2}$ ratio was obtained by dividing the $t_{1/2}$ in the presence of ligand, by the tin in the absence of ligand.

Polyacrylamide Gel Electrophoresis (PAGE) Analysis of Digestion Products.

F13 digestion products were analyzed by denaturing polyacrylamide gel electrophoresis (PAGE) by collecting 5 μL of digestion samples at various time intervals and mixing it with 10 μL of formamide loading buffer (75% formamide, 10% glycerol, 0.125% SDS, 10 mM EDTA, and 0.15% (w/v) xylene cyanol). Each collected sample (6 μL) was loaded into the wells of a 15% denaturing PAGE gel. Separation was carried out at 6 V/cm for 30 mins followed by 25 V/cm for 4 h in 0.5×TBE running buffer. The gel was stained with 1×SYBR Gold solution for 25 mins and imaged using a ChemiDoc MP Image system (Bio-Rad).

Confirmation of Aptamer Structure-Switching Using Circular Dichroism Spectroscopy.

Circular dichroism experiments were performed at room temperature. Prior to each experiment, the aptamer (Final concentration: 1.5 µM) was prepared in Tris-HCl buffer (pH 7.4) and heated to 95° C. for 10 mins and immediately cooled on ice, after which, salts and methanol were added to reach the selection buffer conditions. Acetyl fentanyl dissolved in selection buffer was then added to a final concentration of 10 µM. Samples (300 µL) were transferred into a 1 cm quartz cuvette (Hellma Analytics) for measurements. Circular dichroism measurements were performed using a Jasco J-815 circular dichroism spectropolarimeter with a scan range of 210 to 310 nm, scan speed of 50 nm/min, sensitivity of 5 mdeg, response time of 4 s, bandwidth of 1 nm, and accumulation of 5 scans. Reference spectra of selection buffer were taken with and without 10 µM acetyl fentanyl. Reference spectra were subtracted from circular dichroism spectra collected with aptamer in the absence or presence of acetyl fentanyl.

Isothermal Titration Calorimetry (ITC) Experiments.

All ITC experiments were performed in selection buffer with a MicroCal ITC200 instrument (Malvern). For each experiment, an aptamer solution prepared in Tris-HCl buffer (pH 7.4) was heated at 95° C. for 10 mins and immediately cooled down on ice, after which, salts and methanol were added to reach selection buffer conditions and 300 µL of the mixture was loaded into the sample cell. The syringe was loaded with fentanyl, acetyl fentanyl, or furanyl fentanyl in selection buffer. Concentrations of aptamer and ligands are listed in Table 5. Each titration consisted of an initial purge injection of 0.4 µL and 19 successive injections of 2 µL with a spacing of 180 sec between adjacent injections. The raw data was first corrected for the dilution heat of the ligand and then analyzed with the MicroCal analysis kit integrated into Origin 7 software and fitted with a single-site binding model.

Strand-Displacement Fluorescence Assay.

The first step of the strand-displacement fluorescence assay was to optimize the concentration of 15-nt quencher-modified cDNA (15-cDNA-Dab) to reach ~85% quenching efficiency. To accomplish this, 72 µL F4-FAM, F13-FAM, or F27-FAM (Each final concentration: 50 nM) dissolved in selection buffer was aliquot into nine tubes, after which, 8 µL of 0, 0.08, 0.16, 0.31, 0.625, 1.25, 2.5, 5, or 10 µM 15-cDNA-Dab, dissolved in selection buffer, was added to the solution. The aptamer-15-cDNA-Dab mixture was heat to 90° C. for 10 mins, and slowly cooled down to room temperature over 20 mins to promote annealing. Each solution (70 µL) was loaded into the wells of a Nunc 384-well black plate and the fluorescence intensity at 520 nm was recorded using a Tecan microplate reader (Tecan Infinite M1000 PRO, Switzerland) with a 495 nm excitation wavelength. For single-aptamer-based sensors, 100, 500, or 500 nM 15-cDNA-Dab in selection buffer was mixed with 50 nM of F4-FAM, F13-FAM, or F27-FAM, respectively. The same heating and cooling procedure were applied for the aptamer-15-cDNA-Dab mixture to promote annealing. The mixture (72 µL) was aliquot for each sample tested, followed by the addition of 8 µL of fentanyl at various concentrations. Each sample (70 µL) was loaded into the wells of a Nunc 384-well black plate and the fluorescence intensity at 520 nm was recorded using a Tecan microplate reader (Tecan Infinite M1000 PRO, Switzerland) with a 495 nm excitation wavelength. For testing sensor specificity, the above procedure was repeated, except 8 µL of interferent molecules including: lorazepam, noscapine, papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, mannitol, or lactose was added. For the triple-aptamer sensor a solution containing 16.6 nM F4-FAM, 16.6 nM F13-FAM, 16.6 nM F27-FAM, and 360 nM 15-cDNA-Dab was prepared, after which, the same procedure for the single-aptamer sensor was followed. Optimization of various cDNA-Dab with F27-FAM or F6-FAM in different buffer conditions were performed using the protocol described above.

Fabrication of Electrochemical Aptamer-Based Sensors and Detection.

Aptamer-modified gold electrodes were prepared using a previously reported protocol. Prior to aptamer modification, 2 mm-diameter gold disk electrodes (CHI) were polished with 1 µm diamond suspension (BASi) and 0.05 µm alumina suspension (Buehler), respectively. To remove bound particulates, electrodes were sonicated in 70% ethanol solution and DI solution in an ultrasonic bath for 5 mins each. The electrodes were then electrochemically cleaned using a series of cyclic-voltammetric scans in sodium hydroxide and sulfuric acid solutions. Meanwhile, 100 mM Tris(2-carboxyethyl)phosphine hydrochloride was mixed with F13-39-MB for 2 hours to reduce the disulfide bonds between aptamers. The aptamer was further diluted with immobilization buffer (Final concentrations: 10 mM Tris-HCl, 20 mM NaCl, 0.5 mM $MgCl_2$, 50 µM acetyl fentanyl, and 1% MeOH, pH 7.4) to a final concentration of 100 nM. Cleaned electrodes were incubated in the aptamer solution for 13 hours at room temperature in the dark. After rinsing with distilled water, the electrode was backfilled with 1 mM 6-mercapto-1-hexanol containing 50 µM acetyl fentanyl for 2 hours. Finally, the electrodes were carefully rinsed with distilled water and stored in 10 mM Tris buffer (pH 7.4) for 1 hour. The electrochemical measurements were performed using a CHI760D electrochemical workstation with a three-electrode system containing an Ag/AgCl reference electrode (3M KCl) (CHI), a platinum counter electrode (CHI) and an aptamer-modified gold working electrode. Sensor performance was carried out in selection buffer using square wave voltammetry (SWV). Surface coverage was measured using a previously reported method. Measurements were performed with fentanyl (5 µM), 15 fentanyl analogues (5 µM), 19 interferent molecules (200 µM for papaverine, noscapine and lorazepam, 500 µM for others), and 19 binary mixtures composed of 5 µM fentanyl and 19 individual interferents (200 µM for papaverine, noscapine and lorazepam, 500 µM for others). Signal gain was calculated using the following equation (2):

$$\text{Signal gain} = \frac{I - I_0}{I_0} \times 100 \quad (2)$$

Where $I_0$ is the SWV peak current in the absence of target and I is the SWV peak current in the presence of target. The cross-reactivity was calculated relative to the signal gain obtained in the presence of 5 µM acetyl fentanyl. All data represented the average of measurements taken with three independently fabricated sensors.

Example 1—Selection Strategy and Conditions

To isolate a high-affinity aptamer which is cross reactive to fentanyl and its analogs, selection against three fentanyl family members: Fentanyl, Acetyl fentanyl, and Furanyl fentanyl was performed by using a library-immobilized SELEX technique with a structured library design (FIG. 1). The library pool possesses a 30-nucleotide (nt) random region (FIG. 1, N30) and constant regions composed of two primer binding sites and an 8-nt complementary stem (FIG. 1). The library was hybridized to a biotin-modified 15-base pair (bp) complementary DNA (bio-cDNA) (FIG. 1) which was immobilized onto streptavidin-coated agarose beads via streptavidin-biotin interaction (FIG. 1A). After immobilization of the library pool to the beads, the modified beads were washed with selection buffer to remove library strands which spontaneously elute from the column. A solution of fentanyl or its analogs was then flowed through the column. Aptamer binding to the target dissociated the bio-cDNA. The aptamer-target complexes were eluted into solution (FIG. 1B). These eluted aptamer strands were then PCR amplified, the amplicons were used to generate the single-stranded DNA pool for next round of selection.

To enhance the specificity of the isolated aptamer, counter SELEX was performed. During counter SELEX, interferent compounds were added to the library-bead mixture. Non-specific aptamers which bound to these interferent molecules were eluted from the beads and discarded, the remaining pool was then subjected to positive SELEX. Specifically, the interferent molecules used as counter SELEX targets comprised of adulterants/cutting agents (procaine, lidocaine, quinine, acetaminophen, benzocaine, diphenhydramine, chlorpromazine, lactose, mannitol, caffeine, noscapine, and papaverine) and illicit drugs (cocaine, heroin, codeine, morphine, (+)-methamphetamine, (+)-pseudoephedrine, and lorazepam). The counter SELEX targets were used either individually or combined.

Over the SELEX process, during positive SELEX, target concentration was gradually reduced to increase the stringency of selection conditions to obtain high-affinity aptamers. Counter SELEX was started from round two and the concentration of counter targets was increased over each SELEX round. Specifically, counter selection against lorazepam, noscapine, and papaverine during fentanyl selection began at round seven. The final fentanyl pool was found to still cross react to these counter targets, thus counter selection was performed against these counter targets at earlier rounds for SELEX against acetyl fentanyl and furanyl fentanyl. A total of 11, 10, and 10 rounds for SELEX was performed for fentanyl, acetyl fentanyl, and furanyl fentanyl, respectively, with the selection conditions highlighted in Tables 2, 3, and 4.

TABLE 2

Selection procedure for fentanyl aptamer isolation. The counter SELEX mixtures are as follows. Group 1 (cocaine, procaine, and lidocaine), Group 2 (heroin and quinine), Group 3 (acetaminophen, benzocaine, (+)-methamphetamine, (+)-pseudoephedrine, and diphenhydramine), Group 4 (codeine, morphine, and chlorpromazine), Group 5 (lactose, mannitol, and caffeine), Group 6 (lorazepam), Group 7 (papaverine), and Group 8 (noscapine).

| Round | Pool (pmol) | Wash steps | Counter SELEX | Wash steps | Target (µM) |
|---|---|---|---|---|---|
| 1 | 1000 | 10 | NA | NA | 500 |
| 2 | 350 | 10 | Cocaine (100 µM)　　　　　Heroin (100 µM) | 30 | 500 |
| 3 | 350 | 30 | Group 1 (100 µM)　　　　　Group 2 (100 µM) | 30 | 250 |
| 4 | 300 | 30 | Group 1 (100 µM)　　　　　Group 2 (100 µM) | 30 | 250 |
| 5 | 300 | 30 | Group 1 (100 µM)　　　　　Group 2 (100 µM) | 30 | 250 |
| 6 | 300 | 30 | Group 1 (100 µM)　　　　　Group 2 (100 µM) | 30 | 250 |
| 7 | 300 | 30 | Group 1　Group 2　Group 3　Group 4　Group 5　Group 6　Group 7　Group 8<br>100 µM　100 µM　100 µM　100 µM　100 µM　100 µM　100 µM　100 µM | 30 | 200 |
| 8 | 200 | 30 | Group 1　Group 2　Group 3　Group 4　Group 5　Group 6　Group 7　Group 8<br>250 µM　250 µM　250 µM　250 µM　250 µM　250 µM　250 µM　250 µM | 30 | 100 |
| 9 | 200 | 30 | Group 1　Group 2　Group 3　Group 4　Group 5　Group 6　Group 7　Group 8<br>500 µM　500 ply1　500 µM　500 µM　500 µM　250 µM　250 µM　250 µM | 30 | 75 |
| 10 | 200 | 30 | Group 1　Group 2　Group 3　Group 4　Group 5　Group 6　Group 7　Group 8<br>500 µM　500 µM　500 µM　500 µM　500 µM　250 µM　250 µM　250 µM | 30 | 50 |
| 11 | 200 | 30 | Group 1　Group 2　Group 3　Group 4　Group 5　Group 6　Group 7　Group 8<br>500 µM　500 µM　500 µM　500 µM　500 µM　250 µM　250 µM　250 µM | 30 | 50 |

TABLE 3

Selection procedure for acetyl fentanyl aptamer isolation. The counter SELEX mixtures are as follows. Group 1 (cocaine, procaine, and lidocaine), Group 2 (heroin and quinine), Group 3 (acetaminophen, benzocaine, (+)-methamphetamine, (+)-pseudoephedrine, and diphenhydramine), Group 4 (codeine, morphine, and chlorpromazine), Group 5 (lactose, mannitol, and caffeine), Group 6 (lorazepam), Group 7 (papaverine), and Group 8 (noscapine).

| Round | Pool (pmol) | Wash steps | Counter SELEX | Wash steps | Target (µM) |
|---|---|---|---|---|---|
| 1 | 1000 | 10 | NA | NA | 500 |
| 2 | 350 | 10 | Cocaine (100 µM)　　　　　Heroin (100 µM) | 30 | 500 |
| 3 | 350 | 30 | Group 1 (100 µM)　　　　　Group 2 (100 µM) | 30 | 250 |
| 4 | 300 | 30 | Group 1 (100 µM)　　　　　Group 2 (100 µM) | 30 | 250 |
| 5 | 300 | 30 | Group 1　Group 2　Group 6　Group 7　Group 8<br>100 µM　100 µM　250 µM　250 µM　250 µM | 30 | 250 |
| 6 | 300 | 30 | Group 1　Group 2　Group 6　Group 7　Group 8<br>100 µM　100 µM　250 µM　250 µM　250 µM | 30 | 250 |
| 7 | 300 | 30 | Group 1　Group 2　Group 3　Group 4　Group 5　Group 6　Group 7　Group 8<br>100 µM　100 µM　100 µM　100 µM　100 µM　250 µM　250 µM　250 µM | 30 | 200 |

TABLE 3-continued

Selection procedure for acetyl fentanyl aptamer isolation. The counter SELEX mixtures are as follows.
Group 1 (cocaine, procaine, and lidocaine), Group 2 (heroin and quinine), Group 3 (acetaminophen,
benzocaine, (+)-methamphetamine, (+)-pseudoephedrine, and diphenhydramine), Group 4 (codeine,
morphine, and chlorpromazine), Group 5 (lactose, mannitol, and caffeine), Group 6 (lorazepam),
Group 7 (papaverine), and Group 8 (noscapine).

| Round | Pool (pmol) | Wash steps | Counter SELEX | | | | | | | | Wash steps | Target (µM) |
|---|---|---|---|---|---|---|---|---|---|---|---|---|
| 8 | 200 | 30 | Group 1 250 µM | Group 2 250 µM | Group 3 250 µM | Group 4 250 µM | Group 5 250 µM | Group 6 250 µM | Group 7 250 µM | Group 8 250 µM | 30 | 100 |
| 9 | 200 | 30 | Group 1 500 µM | Group 2 500 µM | Group 3 500 µM | Group 4 500 µM | Group 5 500 µM | Group 6 250 µM | Group 7 250 µM | Group 8 250 µM | 30 | 75 |
| 10 | 200 | 30 | Group 1 500 µM | Group 2 500 µM | Group 3 500 µM | Group 4 500 µM | Group 5 500 µM | Group 6 250 µM | Group 7 250 µM | Group 8 250 µM | 30 | 50 |

TABLE 4

Selection procedure for furanyl fentanyl aptamer isolation. The counter SELEX mixtures are as follows.
Group 1 (cocaine, procaine, and lidocaine), Group 2 (heroin and quinine), Group 3 (acetaminophen,
benzocaine, (+)-methamphetamine, (+)-pseudoephedrine, and diphenhydramine), Group 4 (codeine,
morphine, and chlorpromazine), Group 5 (lactose, mannitol, and caffeine), Group 6 (lorazepam),
Group 7 (papaverine), and Group 8 (noscapine).

| Round | Pool (pmol) | Wash steps | Counter SELEX | | | | | | | | Wash steps | Target (µM) |
|---|---|---|---|---|---|---|---|---|---|---|---|---|
| 1 | 1000 | 10 | NA | | | | | | | | NA | 500 |
| 2 | 350 | 10 | Cocaine (100 µM) | | | | Heroin (100 µM) | | | | 30 | 500 |
| 3 | 350 | 30 | Group 1 100 µM | Group 2 100 µM | | | Group 6 250 µM | | Group 7 250 µM | Group 8 250 µM | 30 | 250 |
| 4 | 300 | 30 | Group 1 100 µM | Group 2 100 µM | | | Group 6 100 µM | | Group 7 250 µM | Group 8 250 µM | 30 | 250 |
| 5 | 300 | 30 | Group 1 100 µM | Group 2 100 µM | | | Group 6 250 µM | | Group 7 250 AM | Group 8 250 µM | 30 | 250 |
| 6 | 300 | 30 | Group 1 100 µM | Group 2 100 µM | | | Group 6 250 µM | | Group 7 250 µM | Group 8 250 µM | 30 | 250 |
| 7 | 300 | 30 | Group 1 100 µM | Group 2 100 µM | Group 3 100 µM | Group 4 100 µM | Group 5 100 µM | Group 6 100 µM | Group 7 100 µM | Group 8 100 µM | 30 | 200 |
| 8 | 200 | 30 | Group 1 250 µM | Group 2 250 µM | Group 3 250 µM | Group 4 250 µM | Group 5 250 µM | Group 6 250 µM | Group 7 250 µM | Group 8 250 µM | 30 | 100 |
| 9 | 200 | 30 | Group 1 500 µM | Group 2 500 µM | Group 3 500 µM | Group 4 500 µM | Group 5 500 µM | Group 6 250 µM | Group 7 250 µM | Group 8 250 µM | 30 | 50 |
| 10 | 200 | 30 | Group 1 500 µM | Group 2 500 µM | Group 3 500 µM | Group 4 500 µM | Group 5 500 µM | Group 6 250 µM | Group 7 250 µM | Group 8 250 µM | 30 | 25 |

Example 2—Fentanyl SELEX

Figures 2A, 2B:
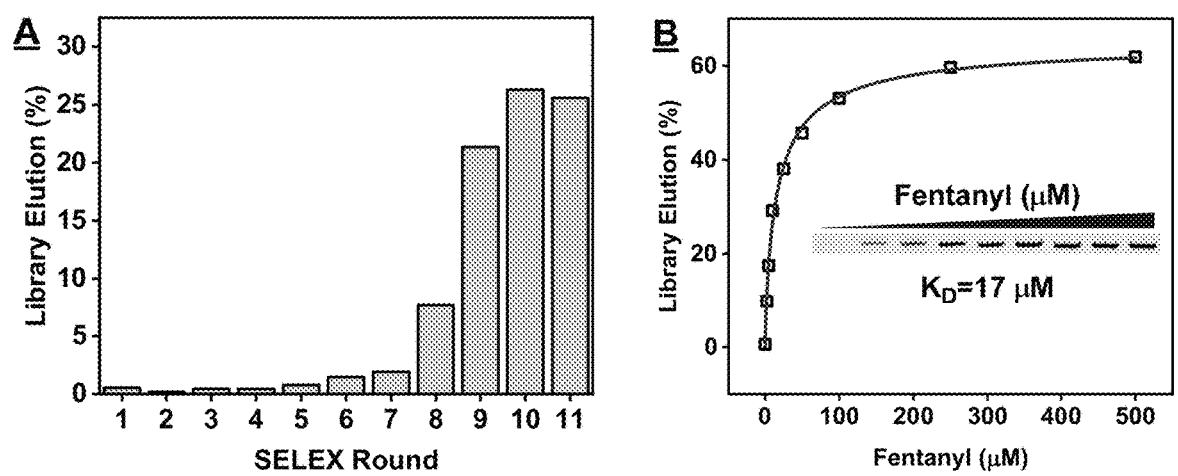
FIGS. 2A-2B show the enrichment of fentanyl-binding aptamers. (A) Library elution during each round upon addition of fentanyl. (B) Determination of round 11 pool affinity using a gel elution assay. Elution of library was done using 0, 2.5, 5, 10, 25, 50, 100, 250, or 500 µM fentanyl (left to right).

The enrichment of fentanyl-binding aptamers was monitored using a gel elution assay. Between selection rounds of 1-7 there was little to no change in the amount of library strands which were eluted by fentanyl from the beads (FIG. 2A, <2%), indicating that fentanyl-binding aptamers have yet to be enriched. During rounds 8 and 9 there was an exponential increase in the fentanyl-eluted library (FIG. 2A). This indicates that the fentanyl-binding aptamers have begun to be enriched. Saturation of enrichment was observed during rounds 10 and 11 (FIG. 2A). Throughout rounds 8-11, the concentration of fentanyl used for elution was reduced from 100 to 50 µM to rapidly enrich high-affinity fentanyl-binding aptamers (Table 2).

Figure 3A:
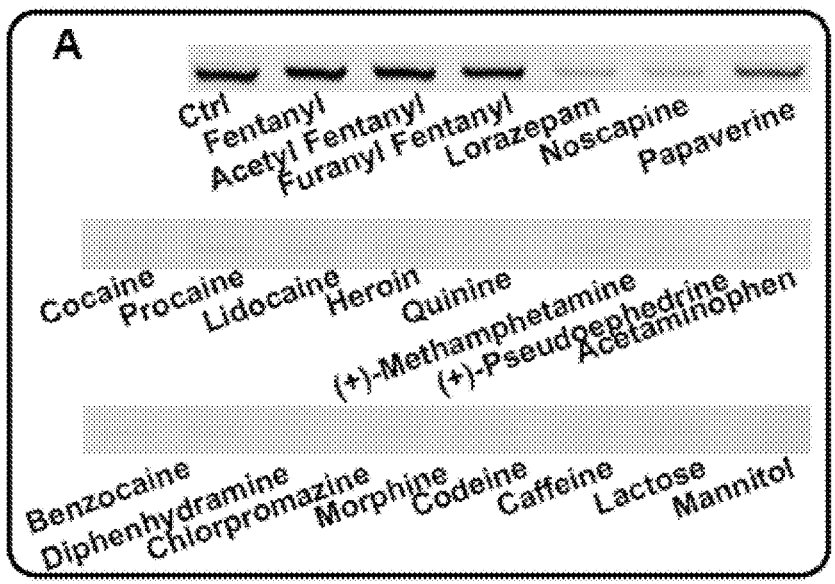
FIGS. 3A-3B show the determination of cross reactivity of the round 11 fentanyl pool. (A) Elution of library in the presence of 25 µM fentanyl, acetyl fentanyl, or furanyl fentanyl, or 100 µM of lorazepam or noscapine or 250 µM of papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, lactose, or mannitol. (B) Cross-reactivity of library against various ligands relative to 25 µM fentanyl.
Figure 3B:
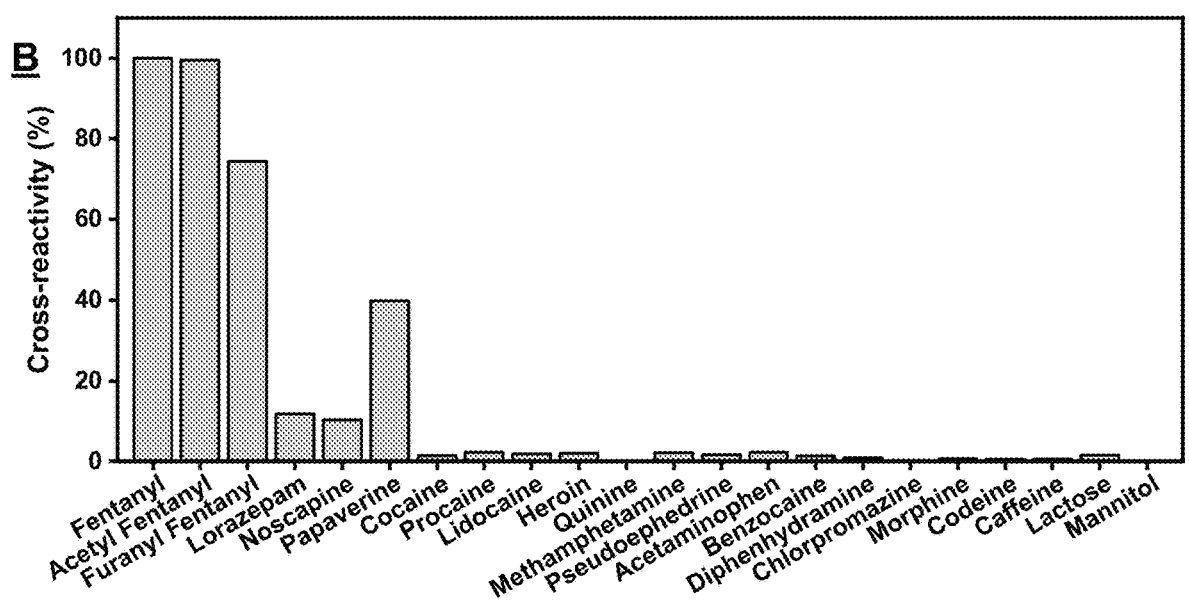

A gel elution assay was performed to characterize the binding properties of the round 11 fentanyl pool. The binding affinity of the round 11 pool was first determined by challenging library-immobilized beads against a variety of fentanyl concentrations and quantifying the eluted library strands. The pool affinity was determined to be 17 µM (FIG. 2B), indicating that the pool is highly enriched with fentanyl-binding aptamers (FIG. 2B). The same assay was then used to characterize the cross reactivity of the pool to fentanyl analogs as well as the counter SELEX targets described in Table 2. Cross reactivities of 99% and 74% for 25 µM acetyl fentanyl and 25 µM furanyl fentanyl, respectively, relative to 100% cross reactivity observed with 25 µM fentanyl (FIG. 3) were observed. Moreover, the pool demonstrated excellent specificity against 16 counter SELEX targets at ten-fold higher concentrations (FIG. 3), with less than 5% cross reactivity from cocaine, procaine, lidocaine, heroin, quinine, acetaminophen, benzocaine, diphenhydramine, (+)-methamphetamine, (+)-pseudoephedrine, codeine, morphine, chlorpromazine, lactose, mannitol, and caffeine. However, three counter SELEX targets demonstrated high binding affinity to the enriched pool with 11.7%, 10.2%, and 39.8% cross reactivity for lorazepam, noscapine, and papaverine, respectively (FIG. 3B).

Example 3—Acetyl Fentanyl SELEX

Based on the results of the fentanyl SELEX, the SELEX procedure was modified for acetyl fentanyl. Specifically, between rounds 1-6, a steady increase was observed in the eluted library strands by acetyl fentanyl (FIG. 4A). Counter SELEX was started from round 5 to remove nonspecific aptamers against lorazepam, noscapine, and papaverine. During rounds 7 and 8 there was an exponential increase in the quantity of eluted library strands with saturation of pool enrichment from rounds 9 to 10 (FIG. 4A). Throughout rounds 7-10 the acetyl fentanyl concentration was reduced from 200 to 50 µM to increase the SELEX stringency for isolating high-affinity acetyl fentanyl-binding aptamers (Table 3).

Figure 5B:
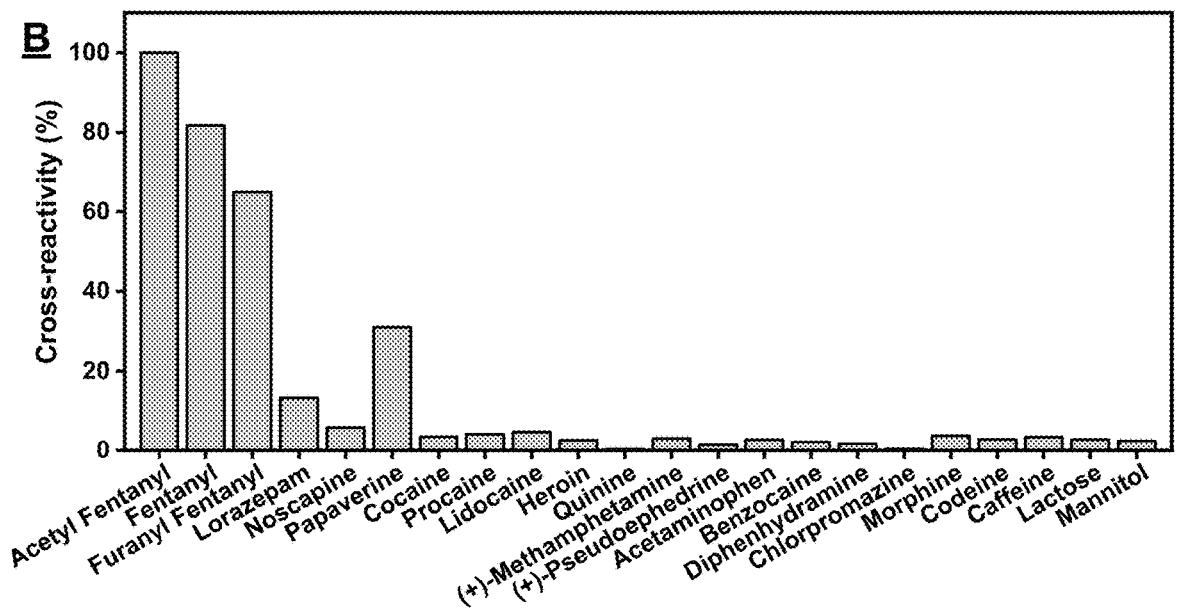

The binding affinity and cross reactivity of the round 10 acetyl fentanyl pool was then characterized using the gel elution assay. The pool affinity was determined to be 15 µM (FIG. 4B). Moderate cross-reactivities of 81% and 64% for 25 µM fentanyl and 25 µM furanyl fentanyl, respectively, relative to 100% cross reactivity observed with 25 µM acetyl fentanyl (FIG. 5) were observed. Finally, the cross-reactivity of the pool was measured against 250 µM of either of the 19 counter SELEX targets (Table 3). Much like the round 11 fentanyl aptamer pool, the round 10 acetyl fentanyl pool displayed little to no cross reactivity (<5%) to all counter targets except lorazepam, noscapine, and papaverine which displayed cross-reactivities of 13.2, 5.8, and 30.9%, respectively (FIG. 5B). The use of earlier counter SELEX against lorazepam had little effect on the final cross reactivity (11.7% vs 13.2%). However, earlier counter SELEX had a moderate improvement in the specificity against noscapine (10.2% to 5.8%) and papaverine (39.8% to 30.9%), indicating that even earlier counter SELEX against these molecules may further improve the specificity.

Example 4—Furanyl Fentanyl SELEX

Figure 6A:
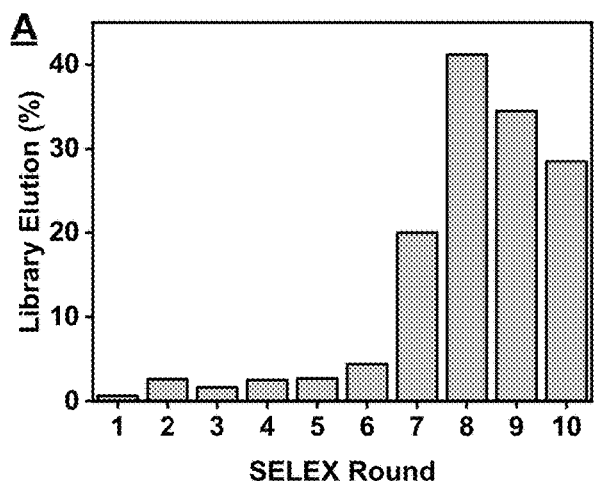
FIGS. 6A-6B show the enrichment of furanyl fentanyl-binding aptamers. (A) Library elution during each round upon addition of furanyl fentanyl. (B) Determination of round 10 pool affinity using a gel elution assay. Elution of library was done using 0, 2.5, 5, 10, 25, 50, 100, 250, or 500 µM furanyl fentanyl (left to right).
Figure 6B:
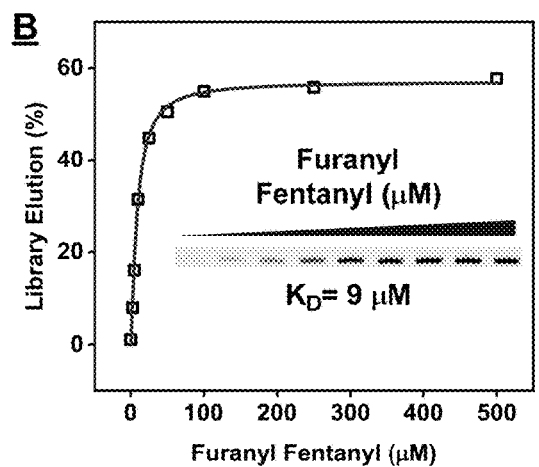
Figure 7A:
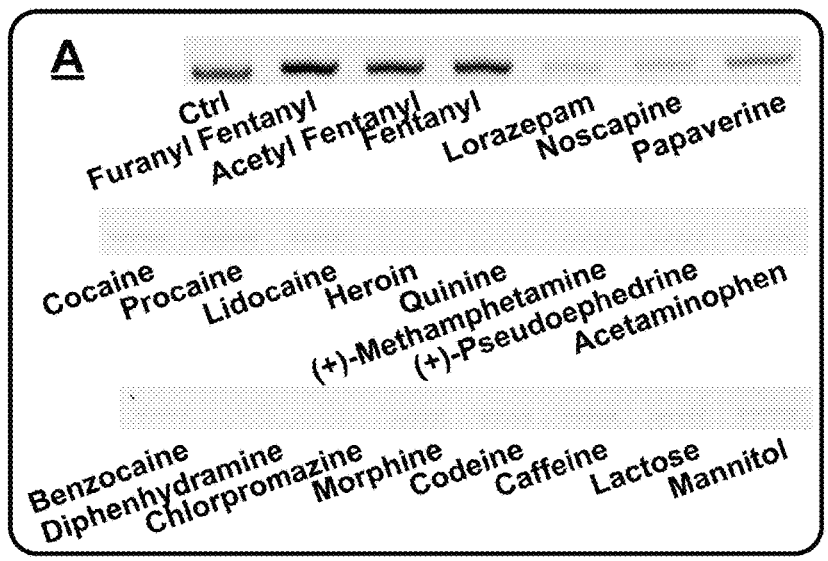
FIGS. 7A-7B show the determination of cross reactivity of the round 10 furanyl fentanyl pool. (A) Elution of library in the presence of 25 µM furanyl fentanyl, acetyl fentanyl, or fentanyl, or 100 µM of lorazepam or noscapine, or 250 µM of papaverine, cocaine, procaine, lidocaine, heroin, quinine, (+)-methamphetamine, (+)-pseudoephedrine, acetaminophen, benzocaine, diphenhydramine, chlorpromazine, morphine, codeine, caffeine, lactose, or mannitol. (B) Cross-reactivity of library against various ligands relative to 25 µM furanyl fentanyl.
Figure 7B:
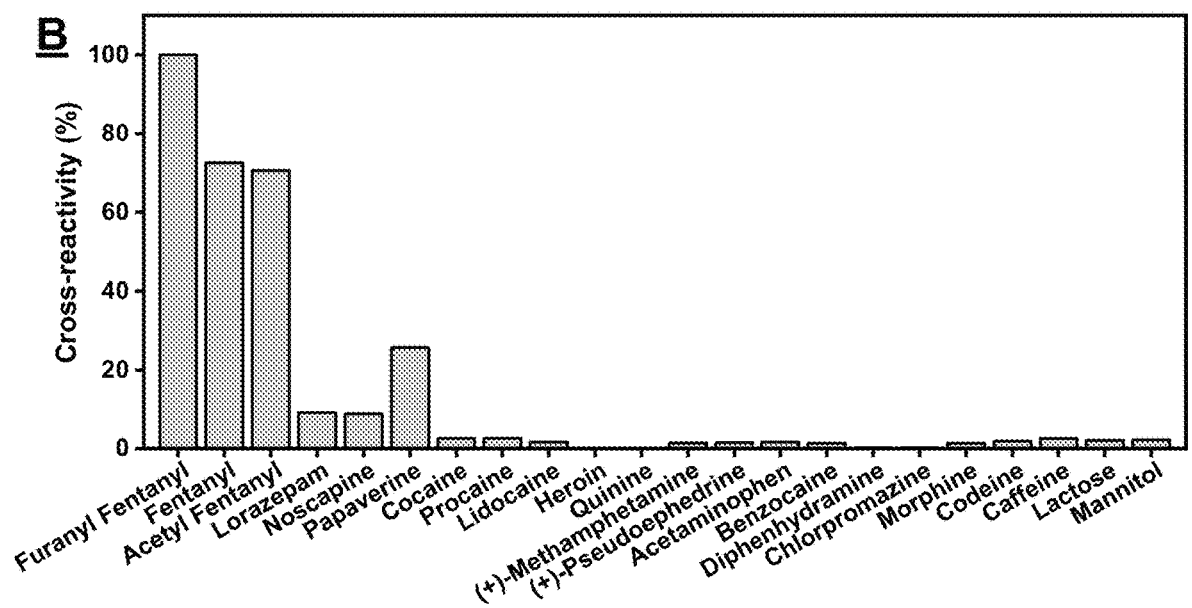

Based on our previous selection procedures against fentanyl and acetyl fentanyl, the furanyl fentanyl selection process was designed with even earlier counter SELEX, particularly against lorazepam, noscapine, and papaverine starting from round 3 (Table 4). Exponential enrichment was not observed up to round 7 (FIG. 6A). The same strategy was used to enrich high-affinity aptamers by reducing the furanyl fentanyl concentration from 200 to 25 µM over the following rounds (Table 4). Saturation of pool enrichment was observed at round 8. There was a slight decrease in the eluted library by furanyl fentanyl for rounds 9 and 10, due to the reduction in target concentration used (FIG. 6A). The binding affinity and cross reactivity of the round 10 furanyl fentanyl pool was characterized using the previously described gel elution assay. A pool affinity of 9 µM was obtained for furanyl fentanyl (FIG. 6B). Cross-reactivities of 80% and 78% for 25 µM fentanyl and 25 µM acetyl fentanyl (FIG. 7), respectively, were observed relative to 100% cross reactivity obtained with 25 µM furanyl fentanyl. Much like the previous selection attempts, little to no cross reactivity (<5%) was observed for 16 of the tested counter SELEX targets (FIG. 7). However, cross reactivities of 9.2, 8.9, and 25.7% was determined for lorazepam, noscapine, and papaverine, respectively (FIG. 7B).

Example 5—High-Throughput Sequencing of Enriched Pools

After observing saturation of pool enrichment and determining that each pool had low micromolar binding affinity, high throughput sequencing of six enriched pools was performed to identify desired aptamer candidates. Specifically, the pools from rounds 9 and 11 for fentanyl, rounds 8 and 10 for acetyl fentanyl, and rounds 7 and 10 for furanyl fentanyl were sequenced. An earlier and final pools were selected for sequencing in order to compare the enrichment-fold of sequences found in both pools. The six selected pools were sequenced using Ion Torrent Sequencing. A total of 3,667,347 reads were obtained for all six pools with 435,632, 521,281, 381,252, 492,320, 410,943, and 1,425,919 reads for round 9 fentanyl pool, round 11 fentanyl pool, round 8 acetyl fentanyl pool, round 10 acetyl fentanyl pool, round 7 furanyl fentanyl pool, and round 10 furanyl fentanyl pool, respectively. The primer sequences were trimmed using cutadapt software and the population and enrichment-fold of sequences from each of the pools were calculated using FASTAptamer software.

The population of sequences found in the early and final selection pools were plotted to identify aptamers with high enrichment-fold (FIGS. 8A, C, & E). Each black dot represents a unique sequence, and its position relative to the dashed line represents its enrichment-fold (FIGS. 8A, C, & E). The dashed line is simulated data representing the same population of the same sequence between two enriched pools. Sequences above or below the line indicate positive or negative enrichment, which demonstrates they were increasing or decreasing in population between the rounds, respectively. In each of the selections, large groups of sequences were observed demonstrating positive and negative enrichment. Only sequences with positive enrichment or high population were considered as potential aptamer candidates as they were able to compete and grow during SELEX. Although many sequences with lower than 1% population demonstrated high enrichment-fold (FIGS. 8A, C, & E), they were disregarded because they lack good binding affinity to out compete other sequences into a greater population. The population of the remaining sequences was then plotted against their enrichment-folds. Two selection thresholds, either population higher than 3.5%, or enrichment-fold higher than 2 with population between 1-3.5%, were set up to find aptamer candidates with high binding affinity and good specificity (FIGS. 8B, D, & F). Based on the first criteria of high population, there were 4, 4, and 4 sequences from the fentanyl, acetyl fentanyl, and furanyl fentanyl pools, respectively, which pass (FIGS. 8B, D, & F), however, 2 from the fentanyl pool also appeared in the furanyl fentanyl pool (F21 and F28), therefore a total of 10 unique sequences were selected from these pools. There were 7, 6, and 8 sequences from the fentanyl, acetyl fentanyl, and furanyl fentanyl pools, respectively, which meet our second criteria of high enrichment-fold (FIGS. 8B, D, & F). However, 1 from the acetyl fentanyl pool also appeared in the furanyl fentanyl pool (F27) and 2 from the furanyl fentanyl pool also appeared in the fentanyl pool (F2 and F6). Therefore, 28 unique sequences were selected and synthesized for further testing (Table 1).

Example 6—Rapid Screening of 28 Aptamer Candidates for their Target-Binding Affinity Using the Exonuclease Digestion Assay Based on HTS analysis, the binding affinity and specificity of 28 aptamer candidates were characterized using a solution-based exonuclease digestion assay. A mixture of exonuclease III (Exo III), a 3'-to-5' double-strand exonuclease, and exonuclease I (Exo I), a 3'-to-5' single-strand exonuclease, can differentiate between unbound- and target-bound DNA aptamers. Specifically, Exo III and Exo I are capable of progressively digesting the double- and single-stranded portions of a DNA aptamer into mononucleotides, in a sequence independent manner. However, digestion of a ligand-bound aptamer is stalled a few nucleotides prior to the binding domain, resulting in aptamer digestion products which can be quantified using the DNA binding dye, SYBR Gold. As a result, aptamers which bind tightly to their targets demonstrate strong enzyme inhibition and emit high fluorescence, whereas unbound or weakly-bound aptamers are digested into mononucleotides and emit low fluorescence. We began by digesting each of the 28 aptamer candidates in the presence or absence of 100 μM of their respective selection target. Throughout the digestion, 5 μL samples were collected from the reaction mixture at various time points and quenched the reaction using quench solution, after which, the remaining oligonucleotide products was quantified using SYBR Gold. The fluorescence intensity was plotted against the reaction time to monitor the digestion progress.

To accurately discriminate high-binding affinity aptamers from weak binders, the enzyme digestion progress of each aptamer candidate was fitted using a first order rate equation. Specifically, we determined the half-life ($t_{1/2}$) of the reaction using equation 1 described above.

The digestion of each aptamer was performed under the same reaction conditions. A variety of reaction rates was observed in the absence of the target, with 27 of the aptamers requiring 1-2 hours for complete digestion and 1 aptamer requiring 4 hours. This difference in reaction rates may be due to the formation of complex tertiary structures which resist digestion at various levels. In order to eliminate the effect of aptamer tertiary structure on the digestion rate, we employed the ratio of $t_{1/2}$ in the presence and absence of 100 μM target as a metric to determine target-binding-resulted enzyme inhibition. A large $t_{1/2}$ ratio indicates a strong enzyme inhibition, whereas, a $t_{1/2}$ ratio of 1 indicates no enzyme inhibition. To ensure that the final selected aptamers have high binding affinity, we used a $t_{1/2}$ ratio of 3.5 as our screening criteria (FIG. 9). Nine aptamers had $t_{1/2}$ ratios less than 3.5 and were omitted from further testing as they did not pass our selection criteria (FIG. 9). Thirteen aptamers (F4, F5, F6, F7, F8, F9, F12, F13, F14, F15, F23, F24, and F25) had $t_{1/2}$ ratios between 3.5-10 and six aptamers (F16, F17, F18, F26, F27, and F28) had $t_{1/2}$ ratios greater than 10. We believe that these nineteen aptamers have high-target binding affinity, thus are selected for detailed characterization of their binding properties.

Figure 10:
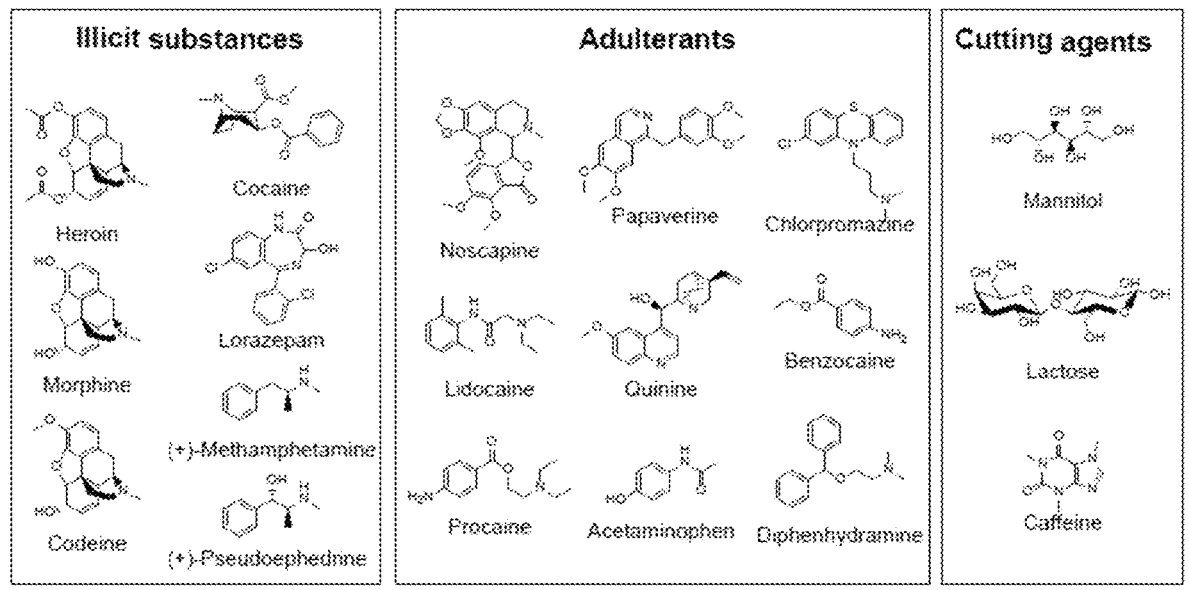
FIG. 10 shows the names and structures of nineteen interferent molecules including illicit substances (heroin, morphine, codeine, cocaine, lorazepam, (+)-methamphetamine, and (+)-pseudoephedrine), adulterants (noscapine, papaverine, chlorpromazine, lidocaine, quinine, benzocaine, procaine, acetaminophen, and diphenhydramine), and cutting agents (mannitol, lactose, and caffeine).
Figure 11A:
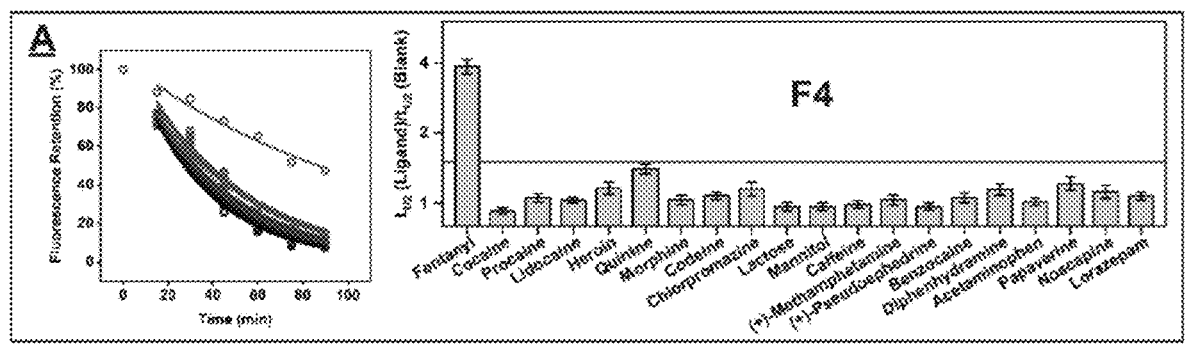
FIGS. 11A-11D show the screening the specificity of four aptamer candidates using an exonuclease digestion assay. Time course digestion and $t_{1/2}$ ratio of (A) F4, (B) F5, (C) F6, and (D) F7. Aptamers were digested in the absence and presence of 100 µM cocaine, lidocaine, procaine, heroin, quinine, codeine, morphine, chlorpromazine, lactose, mannitol, caffeine, (+)-methamphetamine, (+)-pseudoephedrine, benzocaine, diphenhydramine, acetaminophen, papaverine, noscapine, lorazepam, or their selection target (fentanyl).
Figure 11B:
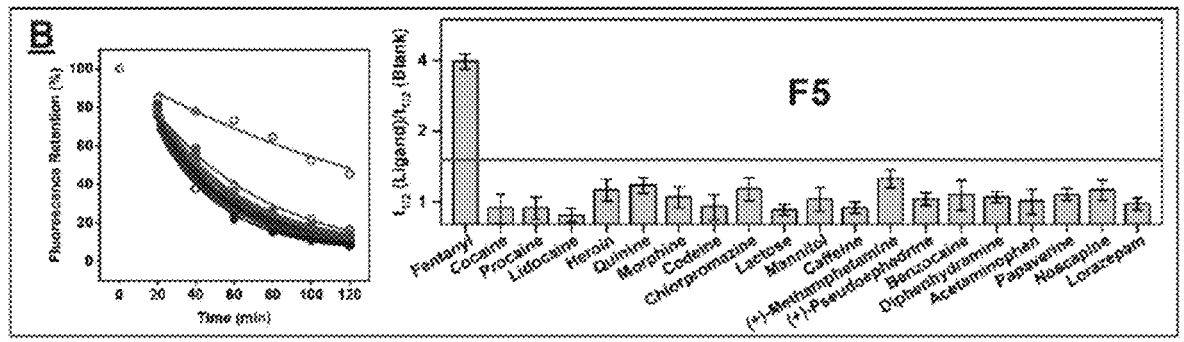
Figure 11C:
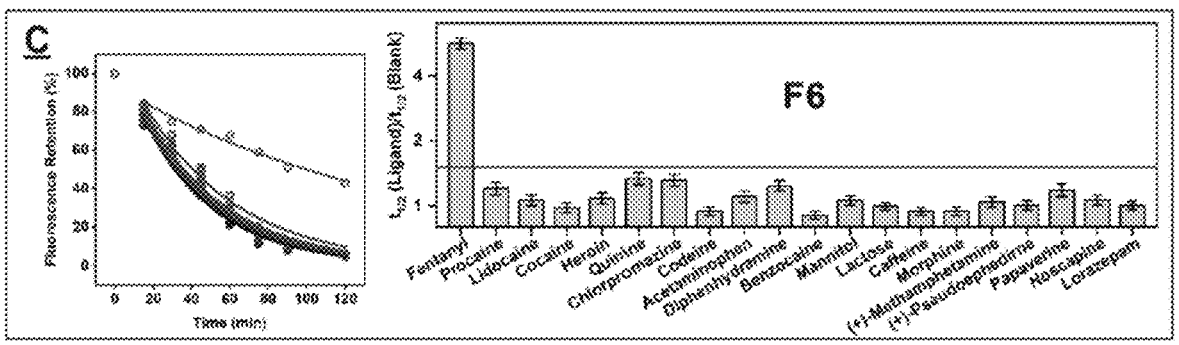
Figure 11D:
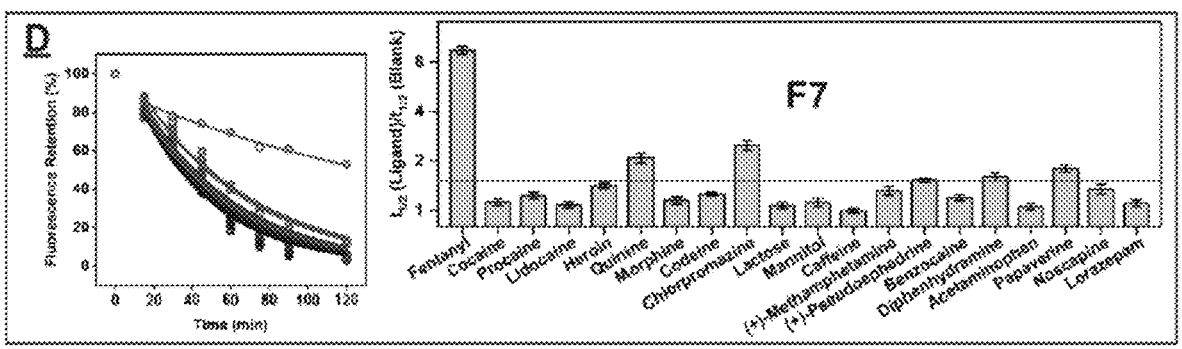
Figure 12A:
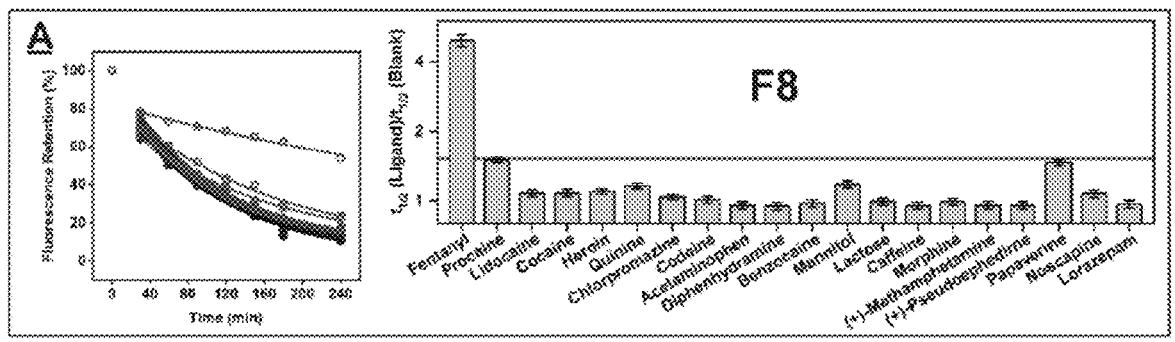
FIGS. 12A-12D show the screening the specificity of four aptamer candidates using an exonuclease digestion assay. Time course digestion and $t_{1/2}$ ratio of (A) F8, (B) F9, (C) F12, and (D) F13. Aptamers were digested in the absence and presence of 100 µM cocaine, lidocaine, procaine, heroin, quinine, codeine, morphine, chlorpromazine, lactose, mannitol, caffeine, (+)-methamphetamine, (+)-pseudoephedrine, benzocaine, diphenhydramine, acetaminophen, papaverine, noscapine, lorazepam, or their selection target (fentanyl or acetyl fentanyl).
Figure 12B:
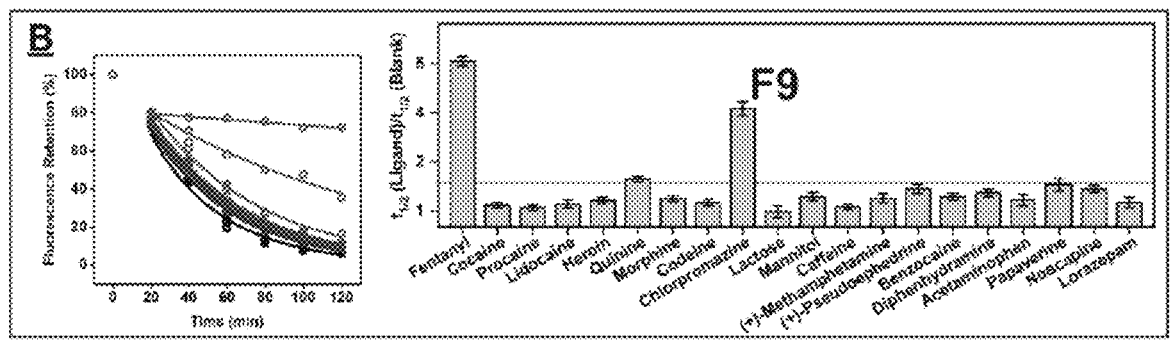
Figure 12C:
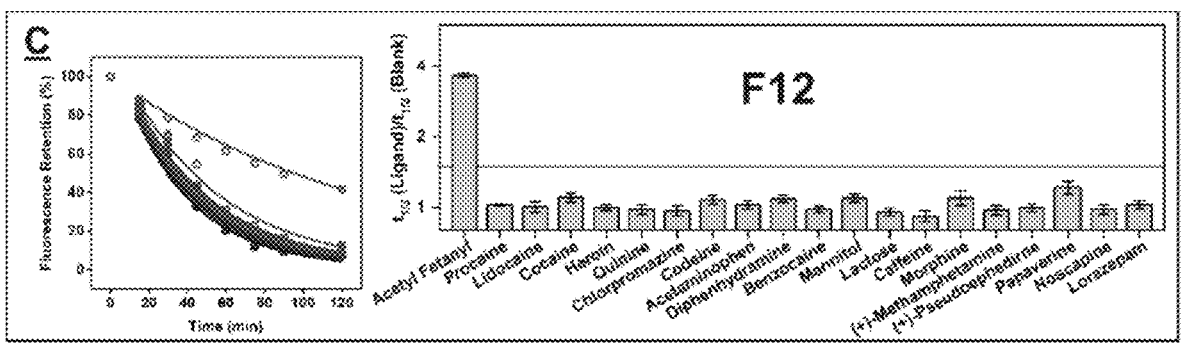
Figure 12D:
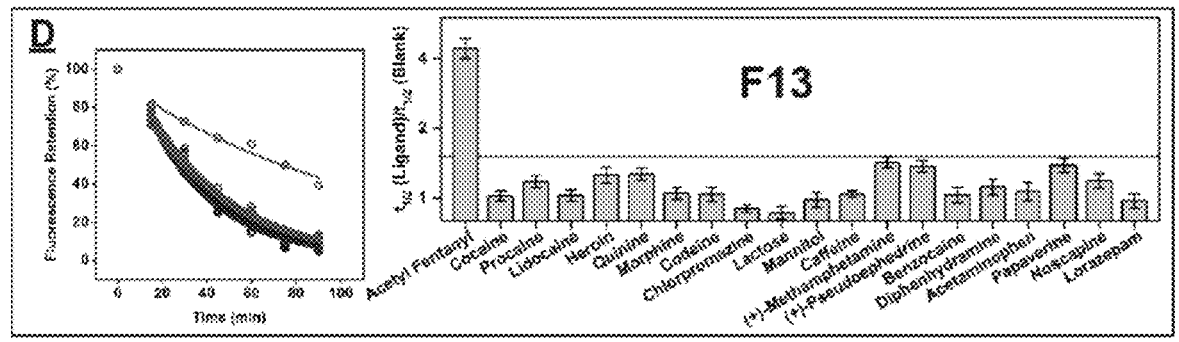
Figure 13A:
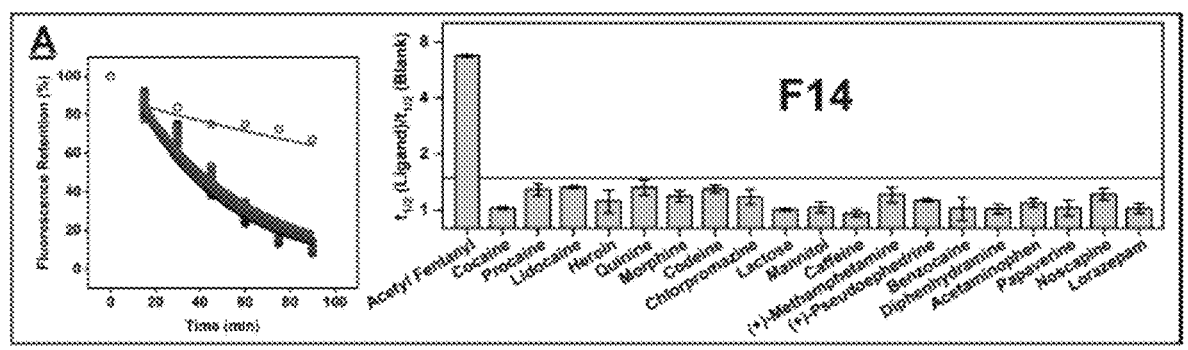
FIGS. 13A-13D show the screening the specificity of four aptamer candidates using an exonuclease digestion assay. Time course digestion and $t_{1/2}$ ratio of (A) F14, (B) F15, (C) F16, and (D) F17. Aptamers were digested in the absence and presence of 100 µM cocaine, lidocaine, procaine, heroin, quinine, codeine, morphine, chlorpromazine, lactose, mannitol, caffeine, (+)-methamphetamine, (+)-pseudoephedrine, benzocaine, diphenhydramine, acetaminophen, papaverine, noscapine, lorazepam, or their selection target (acetyl fentanyl).
Figure 13B:
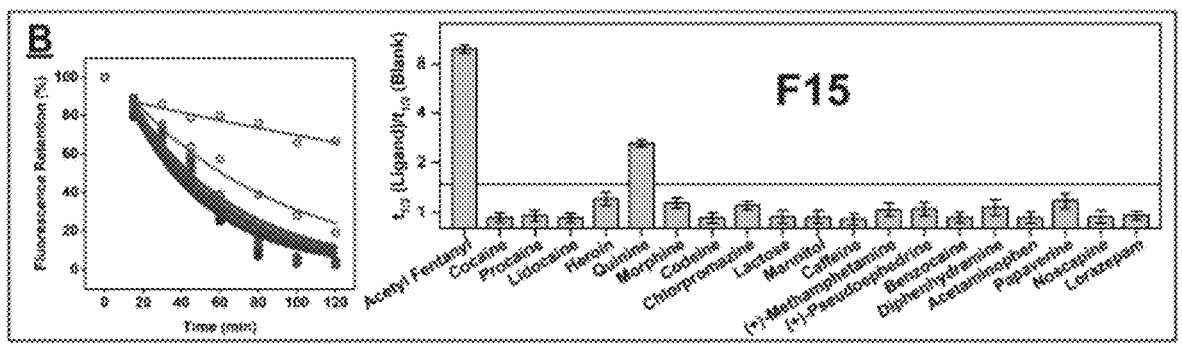
Figure 13C:
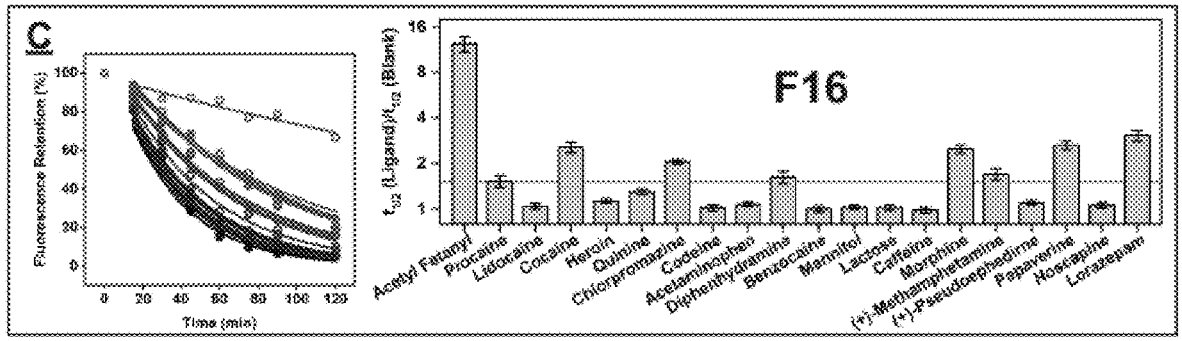
Figure 13D:
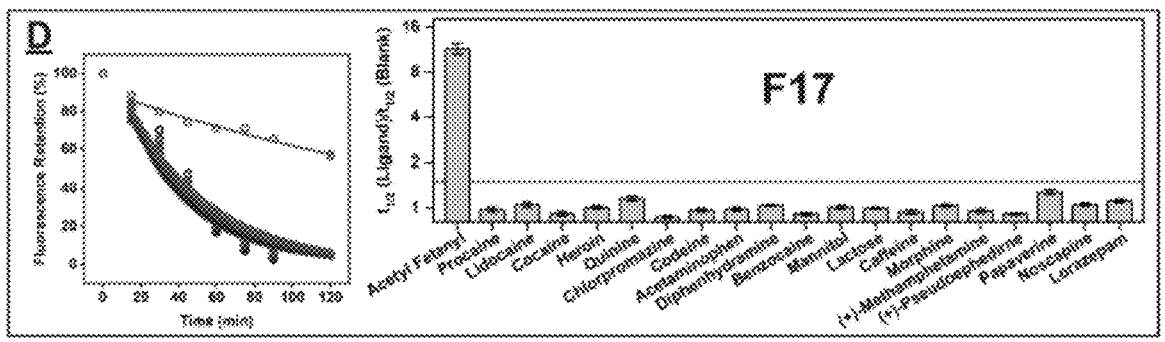
Figure 14A:
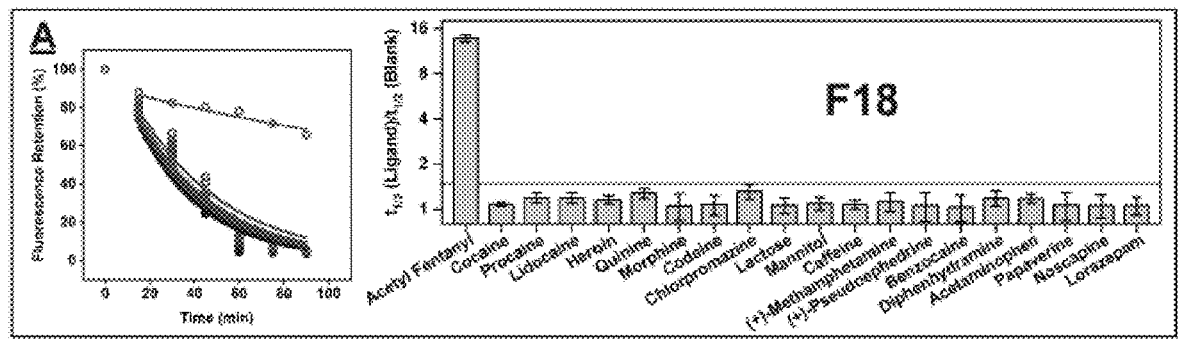
FIGS. 14A-14D show the screening the specificity of four aptamer candidates using an exonuclease digestion assay. Time course digestion and $t_{1/2}$ ratio of (A) F18, (B) F23, (C) F24, and (D) F25. Aptamers were digested in the absence and presence of 100 μM cocaine, lidocaine, procaine, heroin, quinine, codeine, morphine, chlorpromazine, lactose, mannitol, caffeine, (+)-methamphetamine, (+)-pseudoephedrine, benzocaine, diphenhydramine, acetaminophen, papaverine, noscapine, lorazepam, or their selection target (acetyl fentanyl or furanyl fentanyl).
Figure 14B:
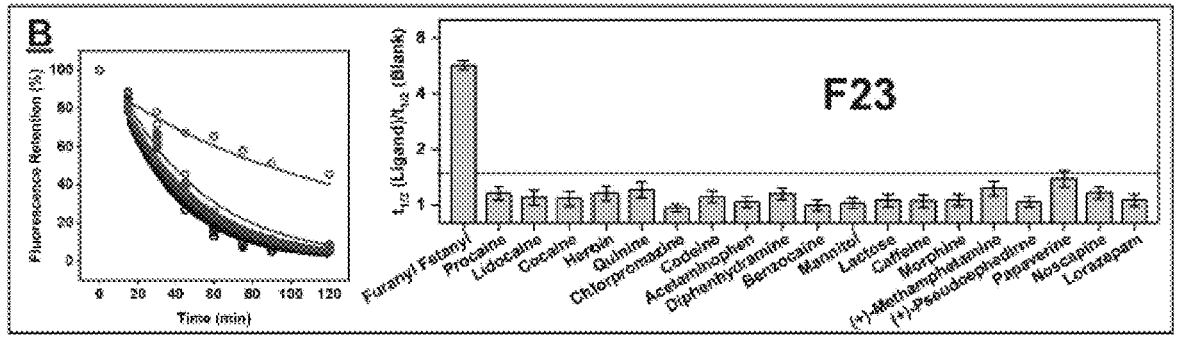
Figure 14C:
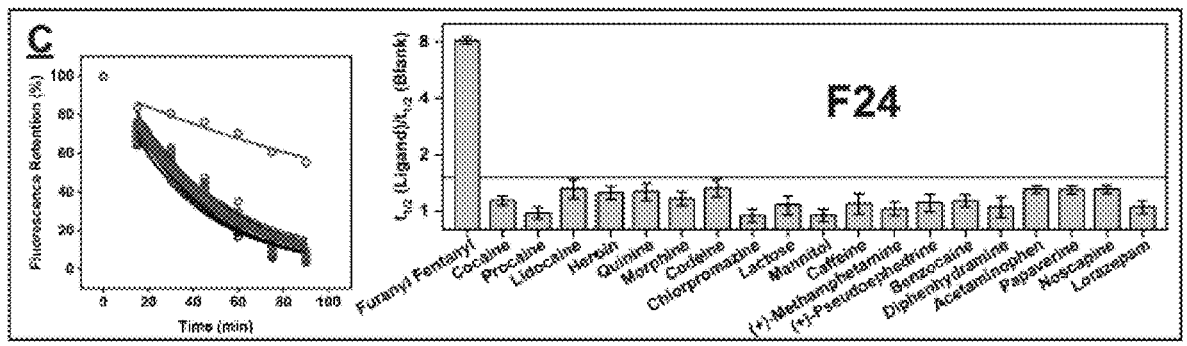
Figure 14D:
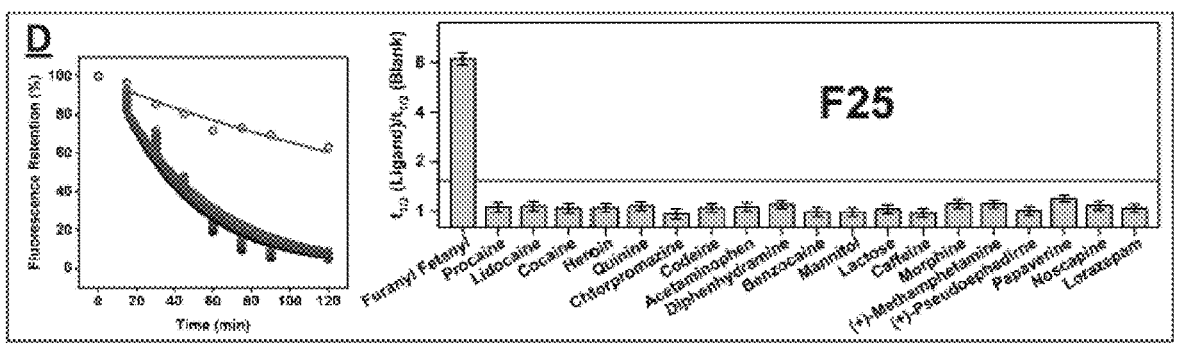
Figure 15A:
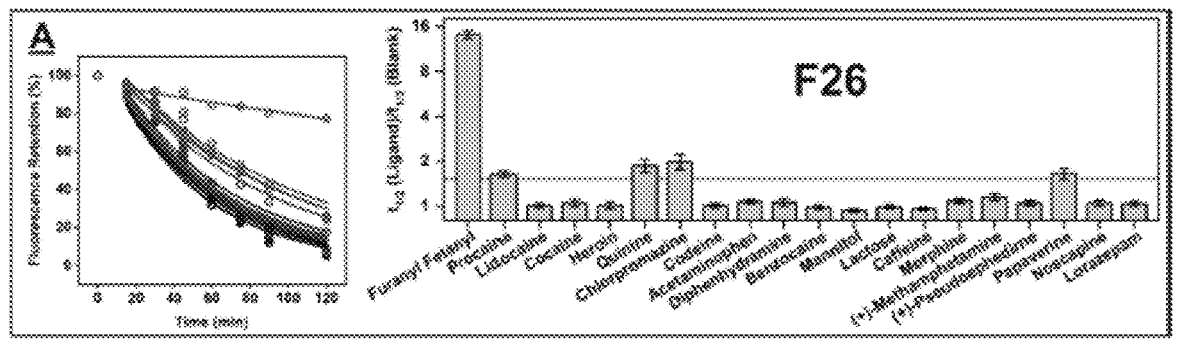
FIGS. 15A-15C show the screening the specificity of four aptamer candidates using an exonuclease digestion assay. Time course digestion and $t_{1/2}$ ratio of (A) F26, (B) F27, and (C) F28. Aptamers were digested in the absence and presence of 100 μM cocaine, lidocaine, procaine, heroin, quinine, codeine, morphine, chlorpromazine, lactose, mannitol, caffeine, (+)-methamphetamine, (+)-pseudoephedrine, benzocaine, diphenhydramine, acetaminophen, papaverine, noscapine, lorazepam, or their selection target (furanyl fentanyl).
Figure 15B:
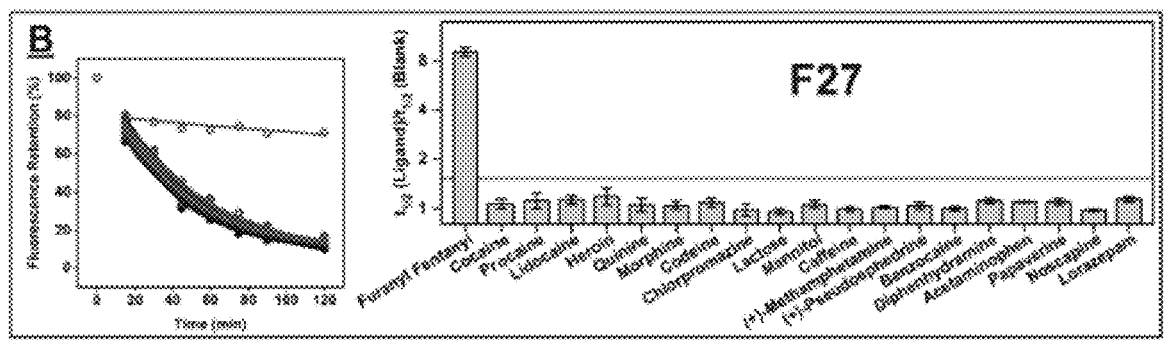
Figure 15C:
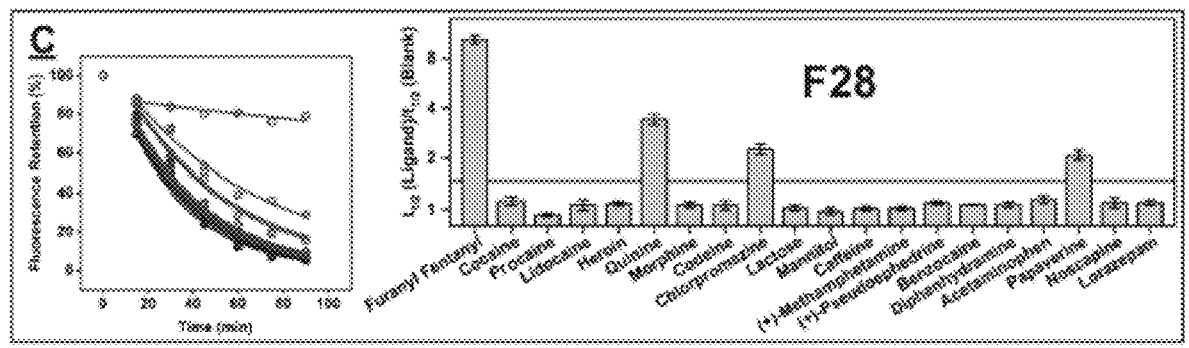
Figure 16A:
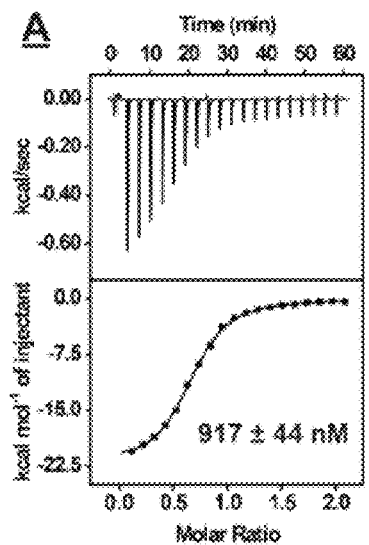
FIGS. 16A-16F show the characterization of target-binding affinity of six aptamer candidates using ITC. Top panels display the heat generated from each titration of fentanyl to (A) F4, (B) F5, (C) F6, and of acetyl fentanyl to (D) F12, (E) F13, and (F) F14. Bottom panels show the integrated heat of each titration after correcting for the heat of dilution of the titrant.
Figure 16B:
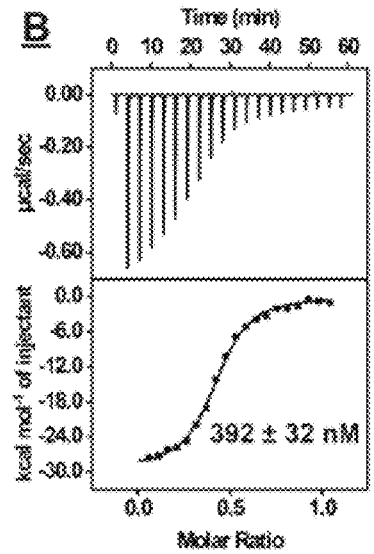
Figure 16C:
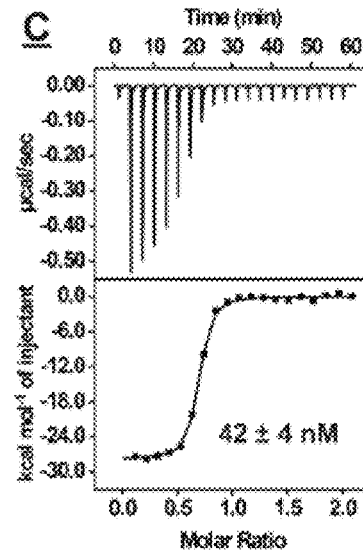
Figure 16D:
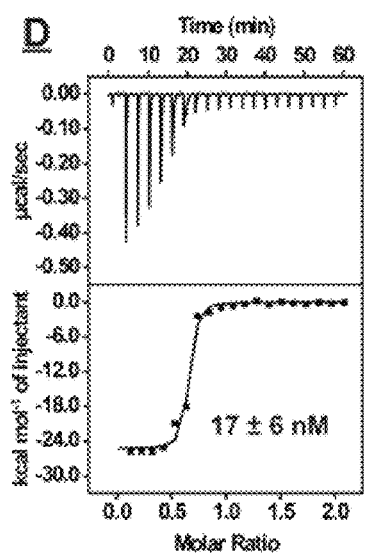
Figure 16E:
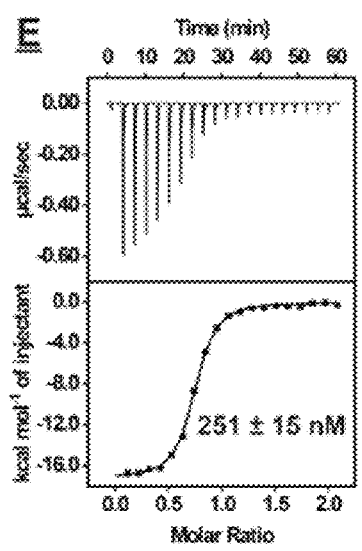
Figure 16F:
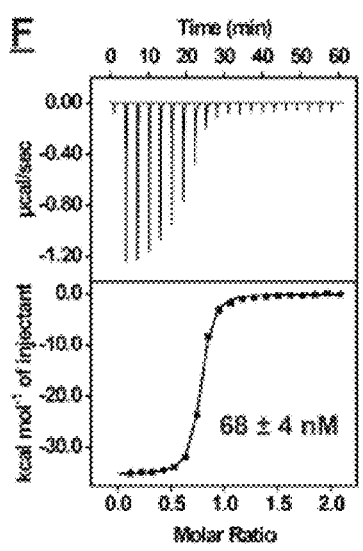
Figure 17A:
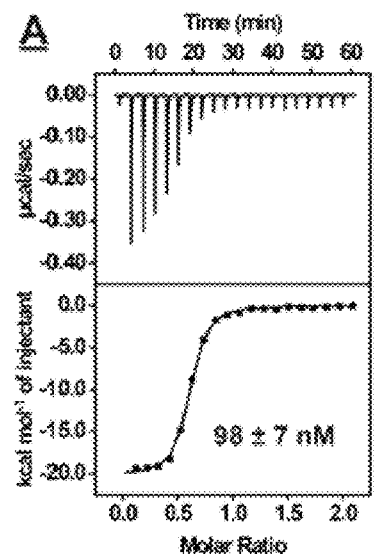
FIGS. 17A-17F show the characterization of target-binding affinity of six aptamer candidates using ITC. Top panels display the heat generated from each titration of acetyl fentanyl to (A) F17, (B) F18, and of furanyl fentanyl to (C) F23, (D) F24, (E) F25, and (F) F27. Bottom panels show the integrated heat of each titration after correcting for the heat of dilution of the titrant.
Figure 17B:
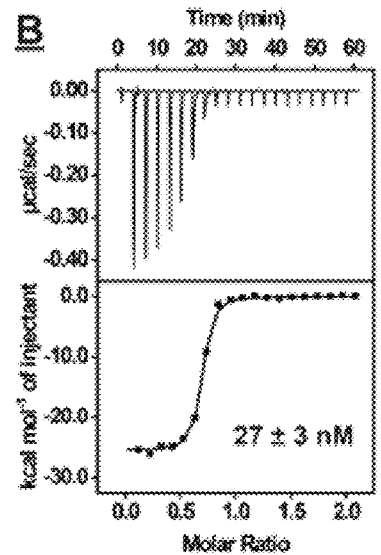
Figure 17C:
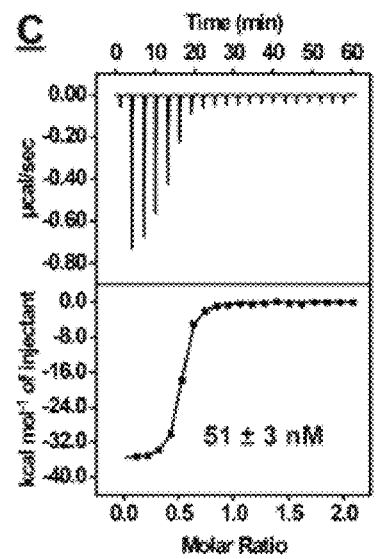
Figure 17D:
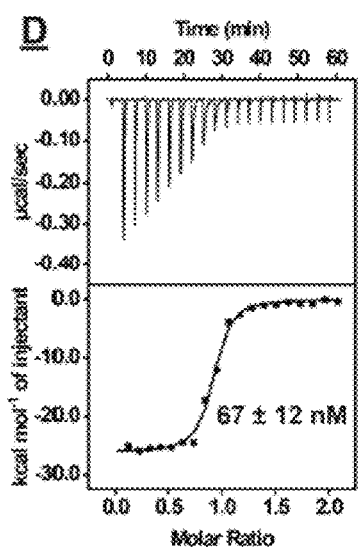
Figure 17E:
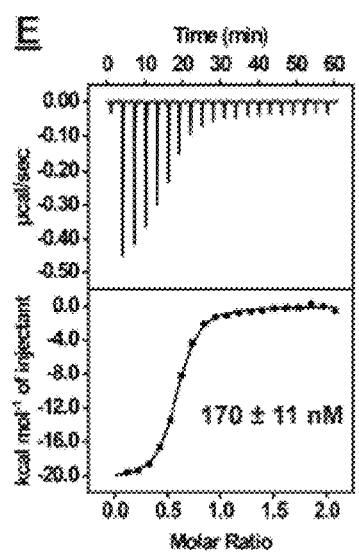
Figure 17F:
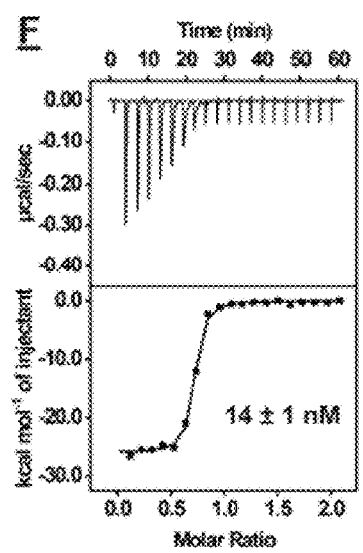

Example 7—Rapid Screening of Specificity of Nineteen Aptamer Candidates Using the Exonuclease Digestion Assay We further tested the specificity of these 19 aptamer candidates against 19 counter-SELEX targets. Specifically, we monitored the digestion progress of each of the aptamer candidates using the same enzyme digestion assay described above, in the absence or presence of 100 μM interferent molecules, including illicit substances (cocaine, heroin, codeine, morphine, (+)-methamphetamine, (+)-pseudoephedrine and lorazepam), adulterants (procaine, lidocaine, quinine, acetaminophen, benzocaine, diphenhydramine, chlorpromazine, papaverine, and noscapine) and cutting agents (caffeine, lactose, and mannitol) (FIG. 10). We used a $t_{1/2}$ ratio of 1.5 to evaluate aptamer specificity as the value <1.5 indicates little to no binding affinity of aptamer to the interferent molecule tested. However, if an aptamer produced a $t_{1/2}$ ratio >1.5 for any interferent molecule, it would be considered nonspecific and omitted from further testing.

From exonuclease-based screening with these 19 aptamer candidates (FIGS. 11-15), we found that 7 aptamers (F7, F8, F9, F15, F16, F26, and F28) had a $t_{1/2}$ ratio >1.5 for at least one interferent molecule (cocaine, diphenhydramine, lorazepam, morphine, quinine, chlorpromazine, or papaverine) and were omitted from further characterization. This is problematic as these molecules are often encountered in seized fentanyl samples. Twelve aptamers (F4, F5, F6, F12, F13, F14, F17, F18, F23, F24, F25, and F27) had $t_{1/2}$ ratios <1.5 for all tested interferent molecules, demonstrating excellent specificity against the tested interferent molecules.

Example 8—Characterization of the Binding Affinity of Twelve Aptamer Candidates Using Isothermal Titration Calorimetry We then identified the binding affinity of the twelve highly-specific aptamer candidates using isothermal titration calorimetry (ITC), since it is the gold standard for determining the binding affinity ($K_D$) of small-molecule-binding aptamers ranging from low nanomolar to high micromolar. We determined a fentanyl binding affinity of 917±44, 392±32, and 42±4 nM for F4, F5, and F6, respectively, an acetyl fentanyl binding affinity of 17±6, 251±15, 68±4, 98±7, and 27±3 nM for F12, F13, F14, F17, and F18, respectively, and a furanyl fentanyl binding affinity of 51±3, 67±12, 170±11, and 14±1 nM for F23, F24, F25, and F27, respectively (FIGS. 16 & 17). ITC experimental conditions, including sequence ID, syringe concentration, aptamer concentration, and dissociation constant are provided in Table 5.

TABLE 5

Aptamer, aptamer concentrations, ligands, and ligand concentrations used for ITC experiments as well as determined $K_D$s.

| Sequence ID | Target | Ligand concentration (μM) | Aptamer concentration (μM) | Dissociation constant (nM) |
| --- | --- | --- | --- | --- |
| F4 | Fentanyl | 200 | 20 | 917 ± 44 |
| F5 | Fentanyl | 100 | 20 | 392 ± 32 |
| F6 | Fentanyl | 100 | 10 | 42 ± 4 |
| F12 | Acetyl fentanyl | 100 | 10 | 17 ± 6 |
| F13 | Acetyl fentanyl | 200 | 20 | 251 ± 15 |
| F14 | Acetyl fentanyl | 200 | 20 | 68 ± 4 |
| F17 | Acetyl fentanyl | 100 | 10 | 98 ± 7 |
| F18 | Acetyl fentanyl | 100 | 10 | 27 ± 3 |
| F23 | Furanyl fentanyl | 100 | 10 | 51 ± 3 |
| F24 | Furanyl fentanyl | 100 | 10 | 67 ± 12 |
| F25 | Furanyl fentanyl | 100 | 10 | 170 ± 11 |
| F27 | Furanyl fentanyl | 100 | 10 | 14 ± 1 |

Figure 18:
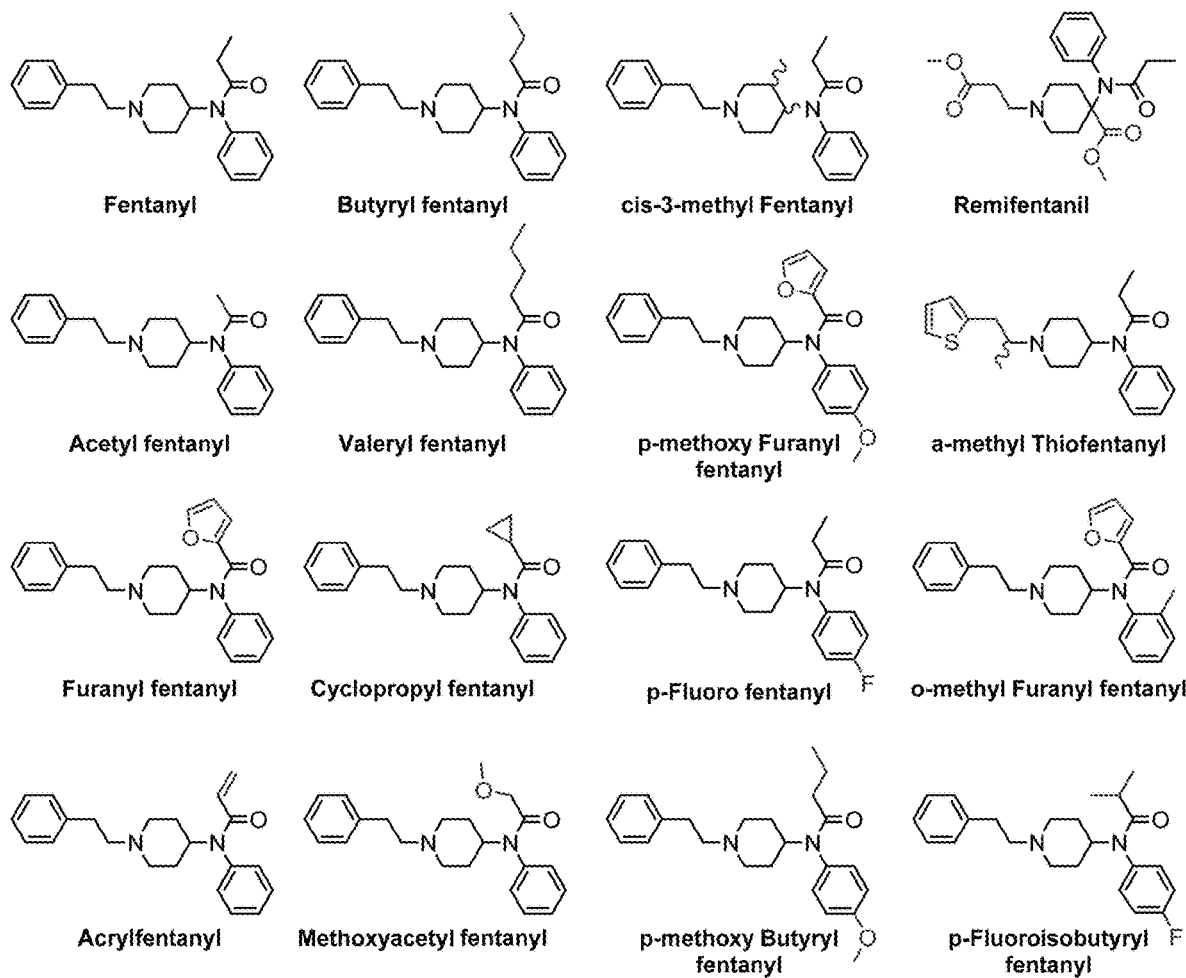
FIG. 18 shows the names and structures of fentanyl and 15 fentanyl analogs. Modifications to the fentanyl structure are highlighted in red.
Figure 19A:
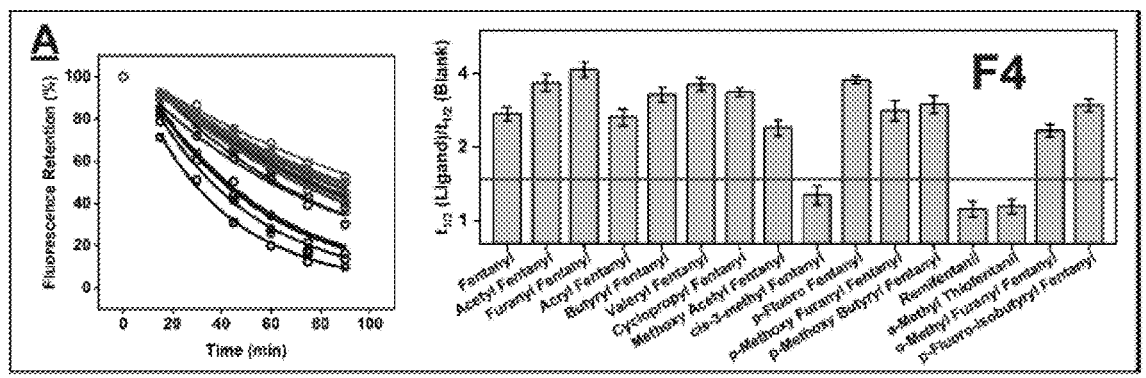
FIGS. 19A-19D show the screening the cross-reactivity of four aptamer candidates to fentanyl and its analogs using an exonuclease digestion assay. Time course digestion and $t_{1/2}$ ratio of (A) F4, (B) F5, (C) F6, and (D) F12. Aptamers were digested in the absence and presence of 100 μM Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.
Figure 19B:
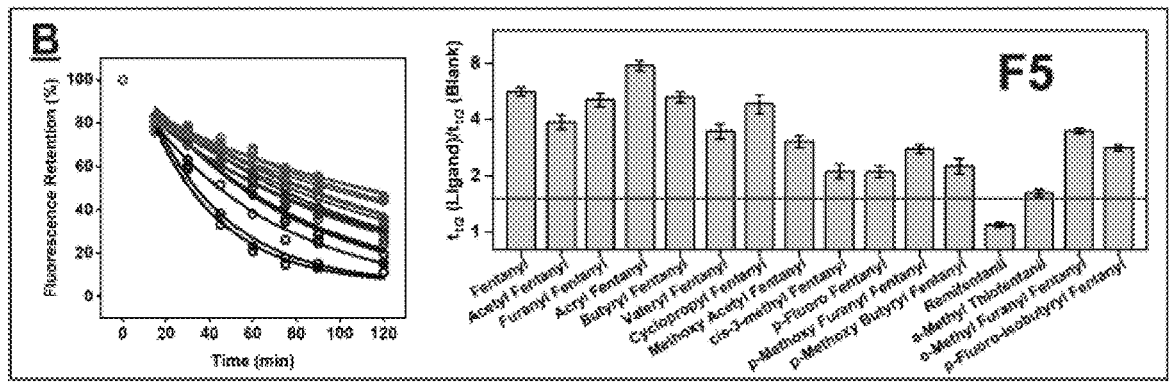
Figure 19C:
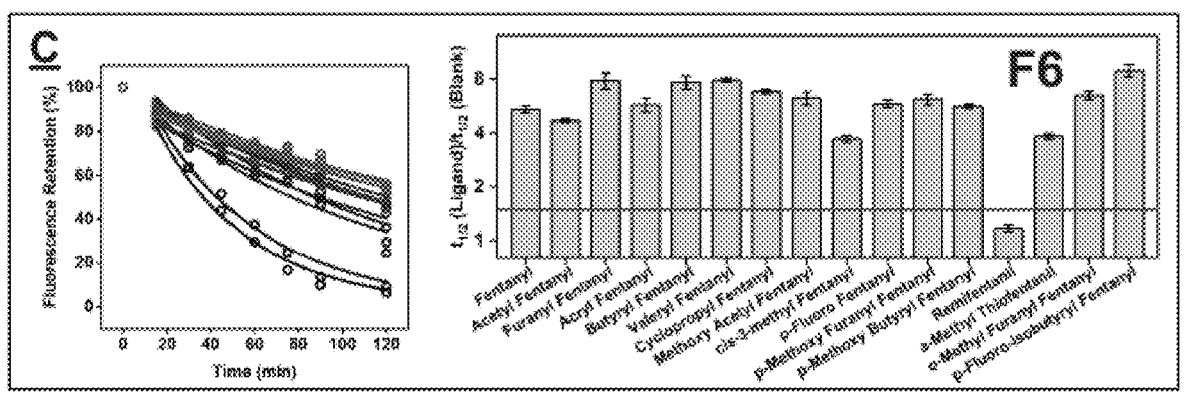
Figure 19D:
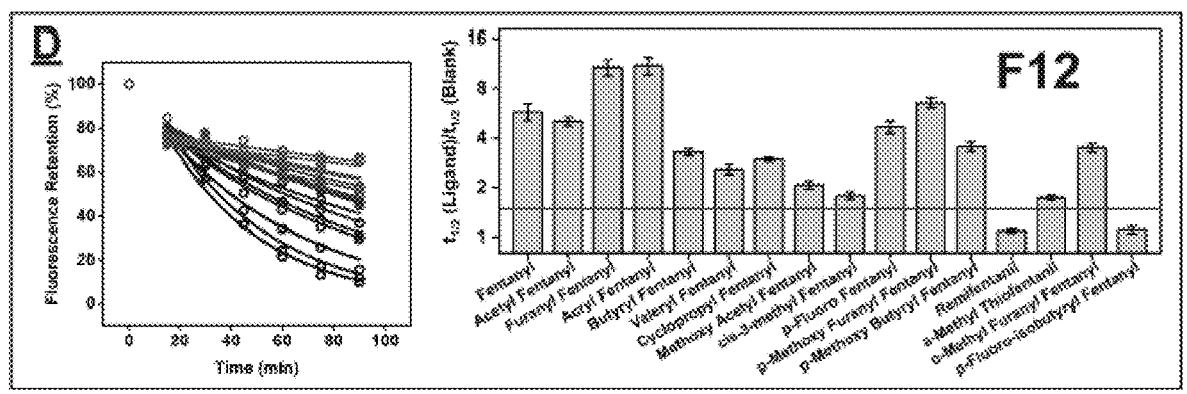

Example 9—Rapid and Accurate Screening of the Cross Reactivities of Twelve Aptamer Candidates Against Fentanyl and its Analogs Using the Exonuclease Digestion Assay We further tested the cross reactivity of twelve aptamer candidates (F4, F5, F6, F12, F13, F14, F17, F18, F23, F24, F25, and F27) against Fentanyl and 15 of its analogs (Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl) (FIG. 18).

Figure 20A:
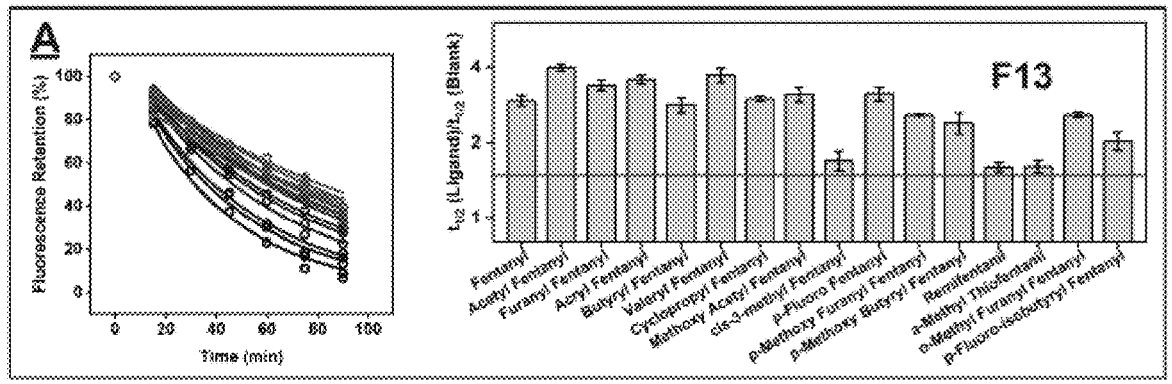
FIGS. 20A-20D show the screening the cross-reactivity of four aptamer candidates to fentanyl and its analogs using an exonuclease digestion assay. Time course digestion and $t_{1/2}$ ratio of (A) F13, (B) F14, (C) F17, and (D) F18. Aptamers were digested in the absence and presence of 100 μM Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl.
Figure 20B:
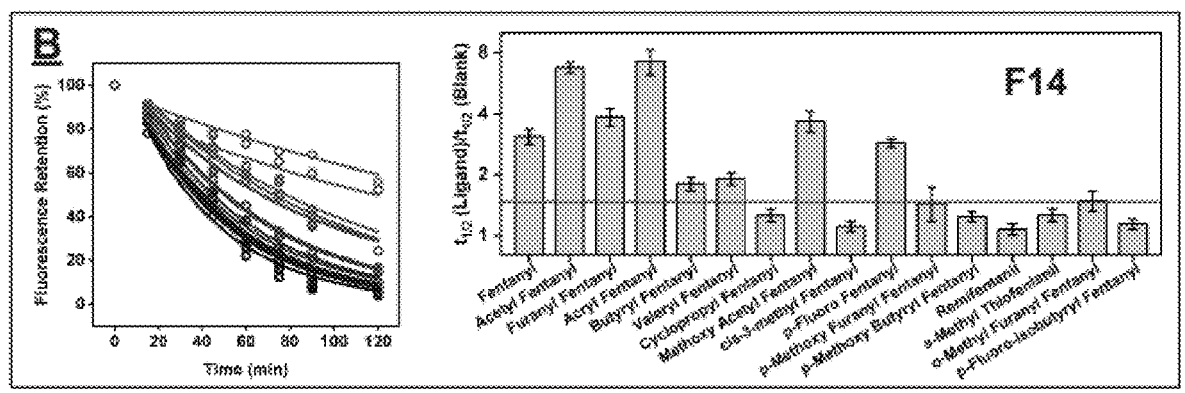
Figure 20C:
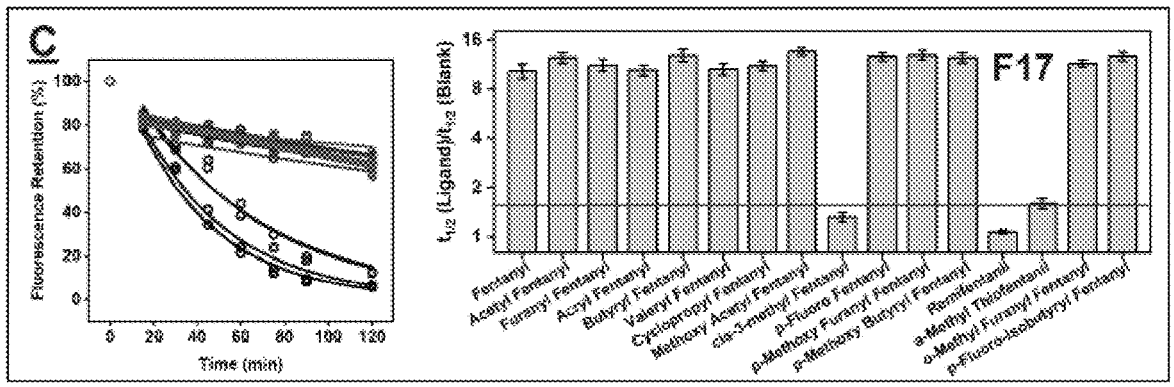
Figure 20D:
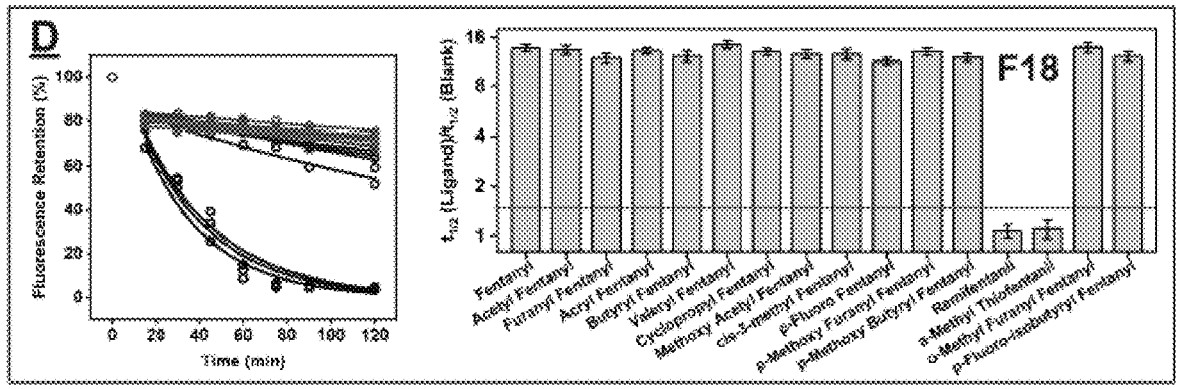
Figure 21A:
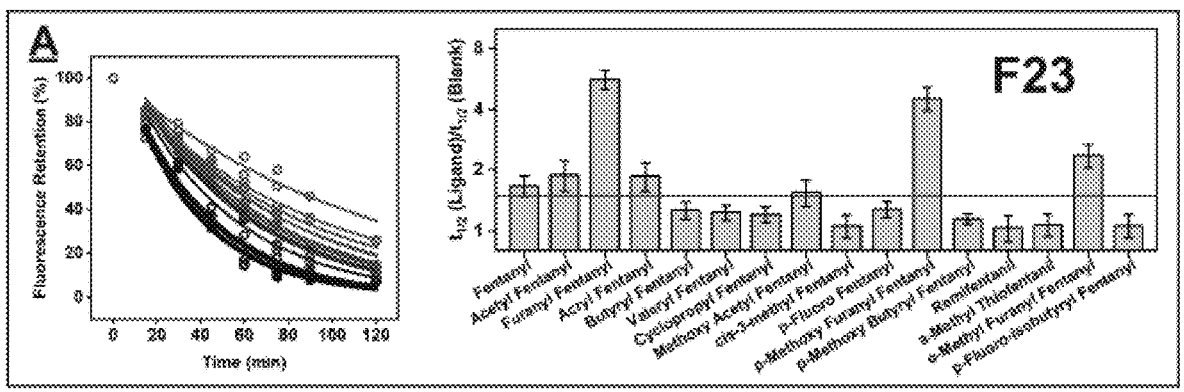
Figure 21B:
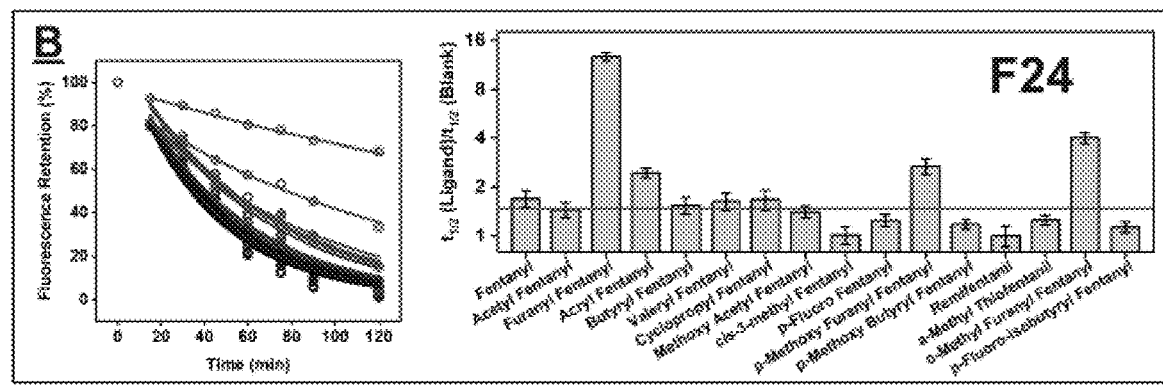

We monitored the digestion progress of each aptamer candidate in the absence and presence of 100 μM fentanyl or its analogs using the enzyme digestion assay described above. To determine the cross reactivity of each aptamer for the tested fentanyl family members, a $t_{1/2}$ ratio of <1.5 indicates weak binding affinity of tested aptamers for the fentanyl family members, whereas a $t_{1/2}$ ratio >1.5 indicates ligand binding. Experimental results indicated that several aptamers were cross reactive, having a $t_{1/2}$ ratio >1.5 for a variety of tested fentanyl family members. For example, 7 fentanyl family members for F23, whereas 8 family members for F14 and F24, 13 family members for F4 and F17, 14 family members for F12, F18, F25, and F27, 15 family members for F5 and F6, and 16 family members for F13 (FIG. 19-21). Some aptamers were found to have exclusivity for a specific functional group. Particularly, F23 and F24 show strong enzyme inhibition ($t_{1/2}$ ratio >2.5) for Furanyl fentanyl, p-methoxy Furanyl fentanyl, and o-methyl Furanyl fentanyl, which all share the furanyl functional group (FIGS. 21A & B). For the tested 12 aptamer candidates, only one aptamer demonstrated binding affinity for remifentanil, α-methyl thiofentanyl, and 3-cis-methyl fentanyl, albeit with weak inhibition ($t_{1/2}$ ratio <2) (FIG. 20A). The remaining 11 aptamer candidates either had no binding for these three family members or only bound to one of these members.

Example 10—Strand-Displacement Fluorescence Assay for Detection of Fentanyl and its Analogs Previous studies have shown that the dynamic range of an aptamer-based sensor can be manipulated by using a combination of aptamers with different binding affinities. To achieve optimal performance, the binding affinity between these aptamers typically differ between 10-100 folds. Based on ITC results, three aptamer candidates (F4, F13 and F27) that would be ideal for the construction of an aptamer-based sensor with an extended dynamic range were selected. ITC results shown that F4, F13, and F27 possess binding affinities of 917±44, 251±15, and 14±1 nM for their selection target and particularly, demonstrate nearly 100% cross-reactivity to fentanyl.

As a demonstration, these three aptamers were used to construct a fluorescence assay for detection of fentanyl based on strand displacement. Aptamer-based strand-displacement is a generalizable sensing method that can be readily incorporated into optical, and electrochemical sensors. This strategy relies on a short cDNA strand that is hybridized to a part of the aptamer but can be readily displaced upon aptamer-target binding. Given the strong interaction between the cDNA and aptamer, it is critical to employ aptamers with high target affinity that are capable of undergoing a large conformational change to efficiently displace the cDNA. The strand-displacement fluorescence assay employs fluorophore-modified aptamers and a quencher-modified complementary DNA strand (FIG. 22). Specifically, each aptamer was modified with fluorescein at its 5'-end and a 15-base pair cDNA was modified with a dabcyl quencher at its 3'-end (15-cDNA-Dab). In the absence of target, these two strands are hybridized and the quencher is located near the fluorophore, efficiently quenching its fluorescence (FIG. 22A). In the presence of target, the aptamer binds to fentanyl, dissociating the 15-cDNA-Dab and recovering its fluorescence (FIG. 22B).

Figure 23A:
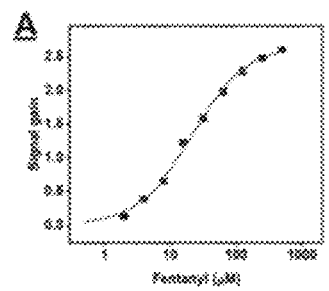
FIGS. 23A-23F show the strand-displacement fluorescence assay performance using a single aptamer. (A) Fentanyl calibration curve and (B) specificity of F4-FAM sensor. (C) Fentanyl calibration curve and (D) specificity of F13-FAM sensor. (E) Fentanyl calibration curve and (F) specificity of F27-FAM sensor. Fentanyl calibration curves were constructed using 0, 2, 4, 8, 15, 31, 62, 125, 250, and 500 μM for F4-FAM, 0, 0.2, 0.4, 0.8, 1.5, 3.1, 6.2, 12.5, 25, and 50 μM for F13-FAM, and 0, 0.02, 0.04, 0.08, 0.15, 0.31, 0.62, 1.25, 2.5, and 5 μM for F27-FAM. Specificity tests were performed against 100 μM cocaine, mannitol, lactose, quinine, lidocaine, heroin, benzocaine, (+)-methamphetamine, diphenhydramine, (+)-pseudoephedrine, acetaminophen, codeine, chlorpromazine, papaverine, noscapine, morphine, caffeine, procaine, and lorazepam, and their cross-reactivities were calculated relative to the signal produced by 100, 10, or 1 μM fentanyl for sensors fabricated using F4-FAM, F13-FAM, and F27-FAM, respectively.
Figure 23B:
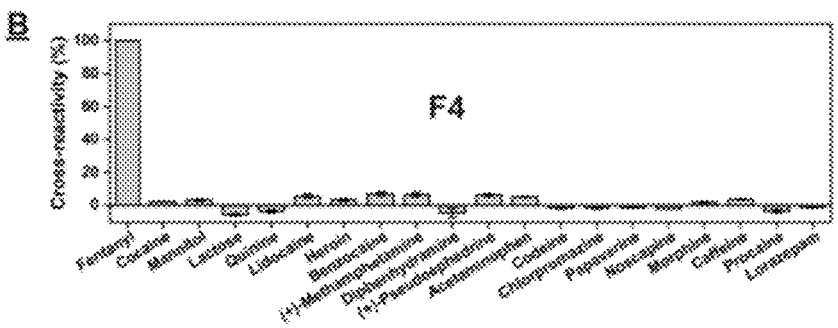
Figure 23C:
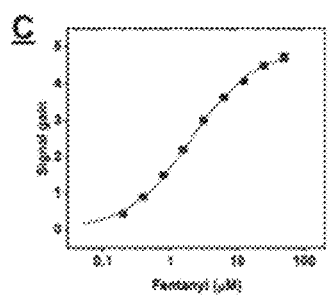
Figure 23D:
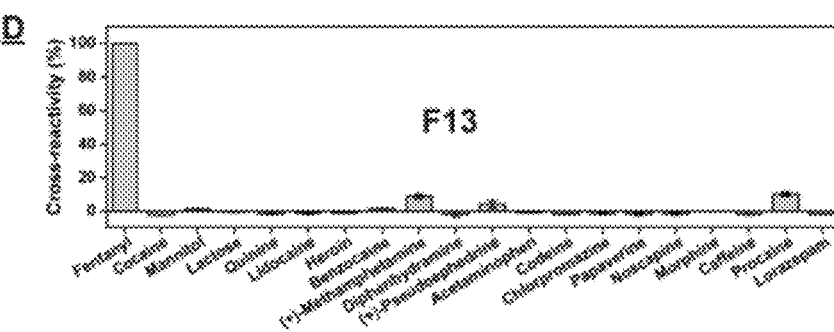
Figure 23E:
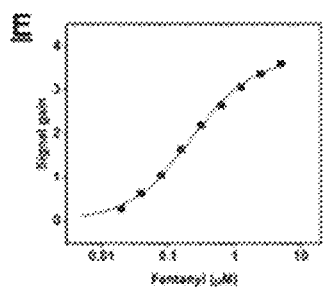
Figure 23F:
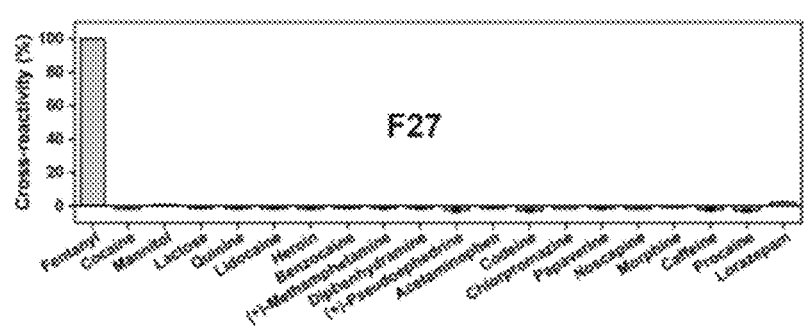

We synthesized each of the fluorescein-modified aptamers and 15-cDNA-Dab and characterized their sensor performance. We first optimized the concentration 15-cDNA-Dab in the strand-displacement fluorescence assay to obtain high signal-to-noise ratio. We observed that 50 nM F4-FAM, 50 nM F13-FAM, and 50 nM F27-FAM required 100, 500, and 500 nM 15-cDNA-Dab, respectively, to reach >85% quenching efficiency (FIG. 22C). We then performed a calibration curve for fentanyl using each individual aptamer-15-cDNA-Dab complex and found that the sensors constructed using F4-FAM, F13-FAM, or F27-FAM provided dynamic ranges of 1.74-141.3, 0.21-17.7, and 0.024-1.98 µM, respectively (FIGS. 23A, C, & E). We also tested the specificity of F4-FAM, F13-FAM, or F27-FAM against 100 µM interferent molecules used in counter-SELEX. As expected, we observed negligible cross-reactivity (<15%) for all the interferent molecules relative to the signal produced by fentanyl (FIGS. 23 B, D, & F).

To extend the dynamic range of the strand-displacement fluorescence assay, we then constructed a triple-aptamer sensor by combining equimolar concentrations of F4, F13, and F27 to reach a final aptamer concentration of 50 nM and hybridized this mixture with 360 nM of 15-cDNA-Dab. The triple-aptamer sensor demonstrated a measurable dynamic range of 0.3-300 µM, providing quantification of fentanyl over three orders of magnitude (FIG. 24A). We also tested the specificity of the triple-aptamer sensor against 500 µM of the interferent molecules and observed negligible cross-reactivity for all tested interferents (<15%, FIG. 24B).

We further probed the performance of the triple-aptamer sensor for detection of fentanyl's analogs by testing three concentrations which allow us to observe the synergistic effect of these aptamers. We challenged the sensor against 0.5, 5, and 50 µM of either Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl (FIG. 25). We observed that the triple-aptamer sensor was capable of responding to 8 fentanyls including Fentanyl, Acetyl fentanyl, Furanyl fentanyl, Acrylfentanyl, Cyclopropyl fentanyl, p-methoxy Furanyl fentanyl, p-Fluoro fentanyl, and o-methyl Furanyl fentanyl with >40% cross-reactivity over all three tested concentrations (FIG. 25). At a high target concentration (50 µM), the cross-reactivity was >40% for all analogs except Remifentanil (FIG. 25A). The cross-reactivity of triple-aptamer sensor for various fentanyl analogues varied at different target concentrations. For example, we observed a cross-reactivity >40% for Butyryl fentanyl, Valeryl fentanyl, Methoxyacetyl fentanyl, and p-methoxy Butyryl fentanyl at concentrations of 50 and 5 µM (FIG. 25A-B). However, the cross-reactivity dropped to 14-33% at a concentration of 0.5 µM (FIG. 25C). Other two analogues such as a-methyl Thiofentanyl and p-Fluoroisobutyryl fentanyl displayed a cross-reactivity >40% at a concentration of 50 µM, with weaker cross-reactivity at 5 µM (22-24%), and no cross-reactivity at 0.5 µM (FIG. 25A-C).

F27-FAM and 15-cDNA-Dab sensing performance was first tested in selection buffer. First, aptamer-cDNA complexes were generated by combining 50 nM F27-FAM with 150 nM 15-cDNA-Dab in selection buffer at 95° C. for 10 mins, followed by cooling to room temperature at a rate of 0.1° C./s. Salt and methanol were then added into the mixture. In the absence of fentanyl, a quenching efficiency of 75%, was observed indicating that most F27-FAM strands were hybridized with 15-cDNA-Dab (FIG. 26A). Upon addition of fentanyl, an increase in fluorescence intensity proportional to the fentanyl concentration was observed, achieving a recovery of 79% of the initial fluorescence intensity at fentanyl concentrations ≥6.4 µM (FIG. 26A). Importantly, even low nanomolar concentrations of fentanyl were able to displace F27-FAM from 15-cDNA-Dab, with 16% fluorescence recovery at 50 nM fentanyl (FIG. 26B).

Example 11—Evaluation of Various F27-FAM and Quencher-Modified cDNA Pairs for Fentanyl Detection in 1×PBS After demonstrating the successful displacement of 15-cDNA-Dab by the binding of fentanyl to F27-FAM in selection buffer, the assay in 1×PBS (10 mM phosphate buffer, pH 7.4, 137 mM NaCl, 2.7 mM KCl, 1 mM $MgCl_2$) was tested, which mimics the high ionic strength of physiological conditions. The same experimental procedure was performed in 1×PBS except no additional methanol was added. 95% quenching efficiency was obtained in the absence of fentanyl (FIG. 26C), indicating that 15-cDNA-Dab binds to F27-FAM with higher affinity under these high ionic strength conditions. However, only ~30% fluorescence recovery was observed in the presence of 25.6 µM fentanyl (FIG. 26C).

15-cDNA-Dab is fully complementary to F27-FAM, and its hybridization directly competes with the formation of an 8-base-pair (bp) stem in target-bound F27-FAM (FIG. 27A). Given that F27-FAM hybridizes to 15-cDNA-Dab with higher binding affinity under high ionic strength conditions, five new quencher-modified cDNAs were engineered (FIG. 27) that vary in thermal stability. To achieve a strong signal from target binding-induced displacement, the affinity of F27-FAM to 15-cDNA-Dab was weakened by removing one nucleotide that paired with the 5'- or 3'-end of the aptamer, yielding 14-5' cDNA and 14-3' cDNA, respectively (FIG. 27B). 15-cDNA-Dab was also mutated to create three additional 15-nt cDNAs (FIG. 27B) that incorporate a single G-T wobble pair at the 5' end (5'-GT cDNA), middle (m-GT cDNA), or 3'-end (3'-GT cDNA) of the cDNA. The resulting aptamer-cDNA structures can be predicted using NUPACK software and found that they have a reduced hybridization free energy relative to 15-cDNA-Dab, with 2.06, 1.51, 3.69, 3.18, and 4.18 kcal/mol, for 14-5', 14-3', 5'-GT, m-GT, and 3'-GT, respectively. These mutated cDNA should be more readily displaced by fentanyl binding, producing a robust signal.

These five alternative quencher-modified cDNAs were synthesized and hybridized with F27-FAM. Their performances were tested for detection of fentanyl at low concentrations (FIG. 28). Sensing performance differed for the various F27-FAM-cDNA pairs. 14-5' cDNA offered the highest quenching efficiency (~93%), but the resulting cDNA-aptamer complex did not respond to fentanyl (FIG. 28A). Low quenching efficiency (~30%) was observed with m-GT cDNA due to the instability of the hybridized complex (FIG. 28B). The 14-5', 5'-GT, and 3'-GT cDNAs offered the strongest response to 50 nM fentanyl, producing 2-3% fluorescence recovery (FIGS. 28C-E), and a full fentanyl calibration curve was constructed using these three quencher-modified cDNA/F27-FAM pairs. Each of the tested cDNAs demonstrated greater performance than 15-cDNA-Dab in 1×PBS, achieving peak fluorescence recovery in the presence of 25 µM fentanyl of 83, 61, and 64% for 14-5', 5'-GT, and 3'-GT cDNA, respectively (FIG. 29A-C). However, the performance of all three sensors for 50 nM fentanyl in 1×PBS was still unsatisfactory compared to 15-cDNA-Dab/F27-FAM in selection buffer, and this may be due to reduced target affinity of F27-FAM in 1×PBS.

Example 12—Generation of New High-Affinity Fluorophore-Modified Aptamer for Fentanyl Detection in 1×PBS To test this hypothesis, the binding affinity of F27 in 1×PBS was determined using ITC. A 21-fold reduction was observed in affinity, with a $K_D$ of 14±1 nM in selection buffer (FIG. 30A) and 304±14 nM in 1×PBS (FIG. 30B). To identify an alternative aptamer, ITC was used to determine the affinity of eight other fentanyl-binding aptamers in 1×PBS. One of these, F6, possessed nanomolar affinity in 1×PBS ($K_D$=48±4 nM, FIG. 30C), making it a promising candidate.

Fluorescein-modified F6 (F6-FAM) was synthesized, and tested for the sensor performance using 50 nM F6-FAM and 150 nM 14-5', 5'-GT, m-GT, or 3'-GT cDNA in 1×PBS (FIG. 31A-D). Much higher quenching efficiency (<13%) relative to F27-FAM was observed, indicating that F6-FAM has a higher affinity for these quencher-modified cDNAs. Although F6-FAM has improved target affinity, only a small response was observed to 50 nM fentanyl (FIG. 31A-D). To further enhance binding-induced fluorescence, assays were performed using the same concentration of F6-FAM but a lower concentration of quencher-modified cDNA (50 nM). Sensors constructed using 14-5' cDNA had very little improvement at 50 nM fentanyl (FIG. 31E), however, an improved response was obtained, where 5'-GT, m-GT, and 3'-GT cDNA demonstrated fluorescence recovery of 6, 6, and 11% with 50 nM fentanyl, respectively (FIG. 31F-H). Under these optimized conditions, calibration curves were constructed over a wider fentanyl concentration range for F6-FAM and 5'-GT, m-GT, or 3'-GT cDNA in 1×PBS (FIG. 32). Excellent response was observed at low fentanyl concentrations, particularly with 3'-GT cDNA (FIG. 32C).

Example 13—Determination of F6 Mutants with Impaired Fentanyl-Binding Affinity After demonstrating that the 3'-GT cDNA/F6-FAM pair can detect fentanyl at low nanomolar concentrations in 1×PBS, we confirmed that the observed signal was due to specific fentanyl binding-induced displacement. Based on high-throughput sequencing data obtained from fentanyl SELEX pools, we identified five potential point-mutation sites (Mut 1-5) in F6 that could potentially impair fentanyl binding (FIG. 33A). The sequences of Mut 1-5 are shown below:

| Sequences ID | Sequence (5'-3') |
|---|---|
| Mut 1 (SEQ ID NO: 78) | CTTACGACTAGTGTAGTAGGGTCGGGTAGTGGGCCTCAGTCGTAAG |
| Mut 2 (SEQ ID NO: 79) | CTTACGACTAGTGGAGTAGTGTCGGGTAGTGGGCCTCAGTCGTAAG |
| Mut 2 (SEQ ID NO: 80) | CTTACGACTAGTGGAGTAGGGTAGGGTAGTGGGCCTCAGTCGTAAG |
| Mut 4 (SEQ ID NO: 81) | CTTACGACTAGTGGAGTAGGGTCGTGTAGTGGGCCTCAGTCGTAAG |
| Mut 5 (SEQ ID NO: 82) | CTTACGACTAGTGGAGTAGGGTCGGGTAGTGTGCCTCAGTCGTAAG |

These mutants were tested using the exonuclease digestion assay. If an aptamer mutant retains binding to fentanyl, this binding impedes the exonuclease-mediated digestion of the aptamer (FIG. 33B, top). If no such binding occurs, Exo III and Exo I digest the aptamer down to mononucleotides (FIG. 33B, bottom). The concentration of partially-digested aptamer is quantified using SYBR Gold, a DNA-binding dye that emits high fluorescence when bound to oligonucleotides but does not bind to mononucleotides.

F6 was digested with a mixture of Exo III and Exo I in both selection buffer and 1×PBS. To accurately determine its binding affinity, the kinetics of aptamer digestion was monitored in the absence and presence of fentanyl. The fluorescence intensity exponentially decreased without target, indicating that the aptamer was being digested into mononucleotides (FIG. 34A-B). In contrast, digestion was inhibited in the presence of fentanyl regardless of the ionic strength of the solution (FIG. 34A-B). The five mutants were then digested in 1×PBS to assess their affinity for fentanyl. All five were rapidly digested into mononucleotides regardless of the absence and presence of fentanyl (FIG. 34C-G), indicating very weak or no binding affinity to fentanyl. The binding affinity of each mutant was then confirmed using ITC. No heat was released upon titration of fentanyl into Mut 1, 2, 4, or 5, indicating no binding affinity (FIG. 35A-D). Low levels of heat release were measured from the titration of fentanyl into Mut 3 (FIG. 35E), but its binding affinity was ~10,000-fold weaker than F6 (FIG. 35F). Based on these findings, a fluorescein-modified variant of Mut 2 (Mut2-FAM) was synthesized for use as a negative control in our strand-displacement assay.

Example 14—Detecting Fentanyl in Serum Using a Strand-Displacement Assay

The previous examples show the sensitive detection of low concentrations of fentanyl in physiological conditions (1×PBS) using 3'-GT cDNA/F6-FAM (FIG. 32C). The performance of 3'-GT cDNA/F6-FAM was evaluated by detecting fentanyl in 50% calf serum. F6-FAM and 3'-GT cDNA were hybridized as described above in 1×PBS, and this solution was then mixed at a 1:1 ratio with calf serum spiked with various fentanyl concentrations (FIG. 36A) and immediately subjected to fluorescence measurement. Sensitive detection of low concentrations of fentanyl was observed in serum (FIG. 36B). However, the sensor performance deteriorated over time, with the signal from fentanyl-containing samples becoming indistinguishable from the blank sample after 30 mins (FIG. 36C). This is most likely due to the presence of serum nucleases that degrade nucleic acids.

Figure 38:
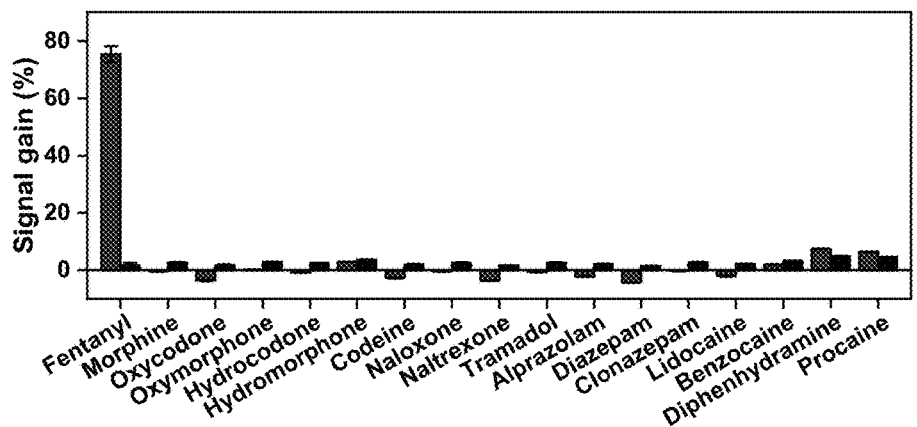
FIG. 38 show the sensor response of F6-FAM and mut2-FAM in 50% deactivated calf serum for 100 nM fentanyl or 10 µM of various other drugs. Signal gain was calculated using the equation ($F_{Target}/F_{Blank}-1$), where F is the fluorescence intensity of the sample. Error bars indicate the standard error from three individual experiments.

To confirm this, the calf serum was deactivated by adding 25 mM EDTA to remove enzyme cofactors necessary for nucleic acid degradation before performing detection of fentanyl. A calibration curve of fentanyl was generated at different concentrations and observed that the signal was stable even after 30 mins, confirming that the signal degradation in untreated calf serum was due to nuclease digestion (FIG. 37A). The 3'-GT cDNA/Mut2-FAM pair produced no response to fentanyl even at a concentration of 10 µM (FIG. 37B), confirming that the signal from 3'-GT cDNA/F6-FAM results from fentanyl binding. Finally, the specificity of 3'-GT cDNA/F6-FAM was tested against 10 µM of various opioids (morphine, oxycodone, oxymorphone, hydrocodone, hydromorphone, codeine, naloxone, naltrexone, or tramadol) or commonly encountered prescription and over-the-counter drugs (alprazolam, diazepam, clonazepam, lidocaine, benzocaine, diphenhydramine, or procaine). As expected, the assay was highly specific for fentanyl, producing a strong signal change with 100 nM fentanyl but no response to other drugs even at a 100-fold higher concentration (FIG. 38). Again, no change was observed in signal for all tested drugs with Mut2-FAM (FIG. 38), confirming the excellent specificity of F6-FAM.

Example 15—Electrochemical Aptamer-Based Sensing of Fentanyl and its Analogs

Electrochemical aptamer-based (E-AB) sensors are a powerful platform which allows for rapid, specific, and sensitive detection of small-molecule analytes in complex samples such as whole blood and serum. This sensor is considered to be "interference-free" due to two reasons. First, the sensors signal is specific to the target-binding-induced conformational change of the employed aptamer. Second, the potential window employed for target detection is outside the range of oxidation/reduction reactions for several endogenous/synthetic compounds. This makes E-AB sensors ideal for the detection of fentanyl and its analogs in seized substances which typically consist of powders containing low doses of fentanyl (<1% w/w) cut with various interferent molecules such as illicit substance (cocaine, heroin, codeine, morphine, (+)-methamphetamine, (+)-pseudoephedrine, and lorazepam), adulterants (procaine, lidocaine, quinine, acetaminophen, benzocaine, diphenhydramine, chlorpromazine, papaverine, and noscapine), and cutting agents (lactose, mannitol, and caffeine).

Figure 39A:
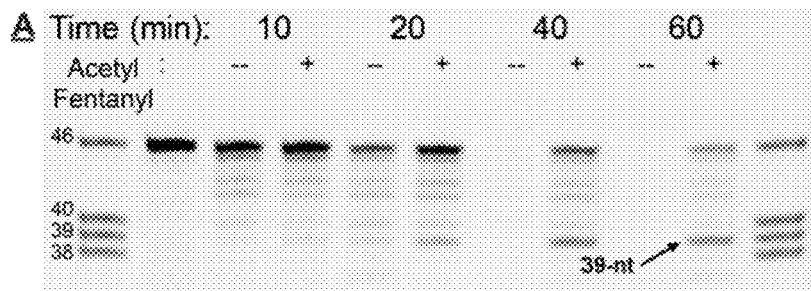
FIGS. 39A-39B show the identification of an F13 structure-switching aptamer. (A) Polyacrylamide gel electrophoresis (PAGE) analysis of a time course digestion of F13 in the absence and presence of 100 µM acetyl fentanyl. A 39-nucleotide inhibition product was observed in the presence of 100 µM acetyl fentanyl. (B) Structure-switching functionality of the 39-nt product (termed F13-39) was confirmed by measuring the circular dichroism spectra in the absence and presence of 10 µM acetyl fentanyl.

The fabrication of an EAB sensor requires the use of structure-switching aptamers. In the absence of target, the structure-switching aptamer is thermally unstable and exists in an unfolded state. In the presence of target, the aptamer undergoes a large conformational change and folds into a stabilized aptamer-target complex. Based on our cross-reactivity and specificity tests, F13 is an ideal candidate for the construction of an E-AB sensor, as it has broad cross-reactivity to fentanyl and its analogs and is highly specific against all tested interferents. However, F13 is a stable stem-loop structured aptamer and likely does not undergo any measurable conformational changes upon binding to the target. To introduce structure-switching functionality to F13, we employed an exonuclease-directed truncation strategy. We previously demonstrated that the digestion of an aptamer by a mixture of Exo III and Exo I in the presence of its target resulted in a truncated aptamer which possesses structure-switching functionality. Specifically, we performed digestion of F13 in the absence and presence of 250 µM acetyl fentanyl. We found that the aptamer was completely digested into mononucleotides in the absence of acetyl fentanyl (FIG. 39A), however, a 39-nt digestion product was obtained in the presence of acetyl fentanyl (FIG. 39A).

Figure 39B:
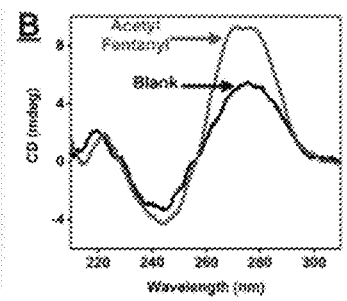

To confirm if this product is a structure-switching aptamer, we chemically synthesized the 39-nt digestion product, termed F13-39, and measured its circular dichroism spectra in the absence and presence of 10 µM acetyl fentanyl (FIG. 39B). We observed two positive peaks at 220 and 280 nm and one negative peak at 240 nm in the absence of acetyl fentanyl (FIG. 39B). In the presence of acetyl fentanyl, the intensity of the positive peak at 280 nm and negative peak at 240 nm increased (FIG. 39B). This behavior is characteristic of the formation of B-form duplex DNA, confirming that F13-39 is a structure-switching aptamer.

To fabricate an E-AB sensor, we chemically synthesized an electroactive tag-modified F13-39 (termed F13-39-MB). Specifically, the 5'-overhang of F13-39 was removed and the 5'- and 3'-ends of the aptamer were covalently modified with a $C_6$-thiol group and methylene blue redox tag, respectively. Prior to electrode modification, F13-39-MB was incubated with 100 mM tris-(2-carboxyethyl)-phosphine for 1 hour to reduce disulfide bonds of aptamers. The reduced aptamer was then diluted with selection buffer (10 mM Tris-HCl, pH 7.4, 20 mM NaCl, 0.5 mM $MgCl_2$, and 1% MeOH) containing 50 μM of acetyl fentanyl, and a gold disk electrode was then incubated in the solution for 13 hours, allowing for the formation of a self-assembled aptamer monolayer via thiol-gold bond. The electrode surface was further backfilled with 6-mercapto-1-hexanol for 2 hours. Finally, the electrode was stored in a 10 mM Tris-HCl (pH 7.4) solution for 1 hour prior to use.

Figure 40A:
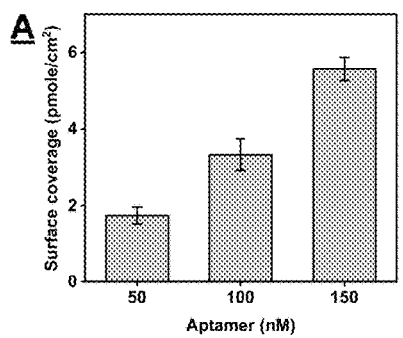
FIGS. 40A-40C show the optimization of F13-39-MB sensor performance. (A) Surface coverage of sensors fabricated using 50, 100, or 150 nM F13-39-MB. (B) Detection of acetyl fentanyl using E-AB sensors constructed with 50, 100, or 150 nM F13-39-MB. (C) Linear range of sensor constructed with 100 nM F13-39-MB. Values represent the average and standard deviations from three independent electrodes.
Figure 40B:
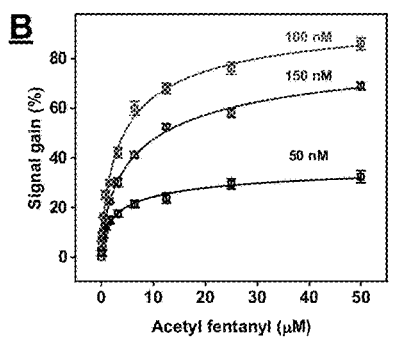
Figure 40C:
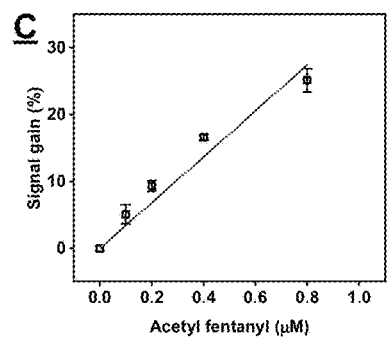

We first tested the effect of the surface coverage of F13-39-MB on the sensor performance. We fabricated E-AB sensors using either 50, 100, or 150 nM of F13-39-MB and challenged them against various concentrations of acetyl fentanyl. We found that a surface coverage of 3.33±0.41 pmole/$cm^2$ provided the best signal gain (FIGS. 40A & B) and achieved a detection limit of 100 nM with a linear range from 100-800 nM (FIG. 40C).

Figure 41A:
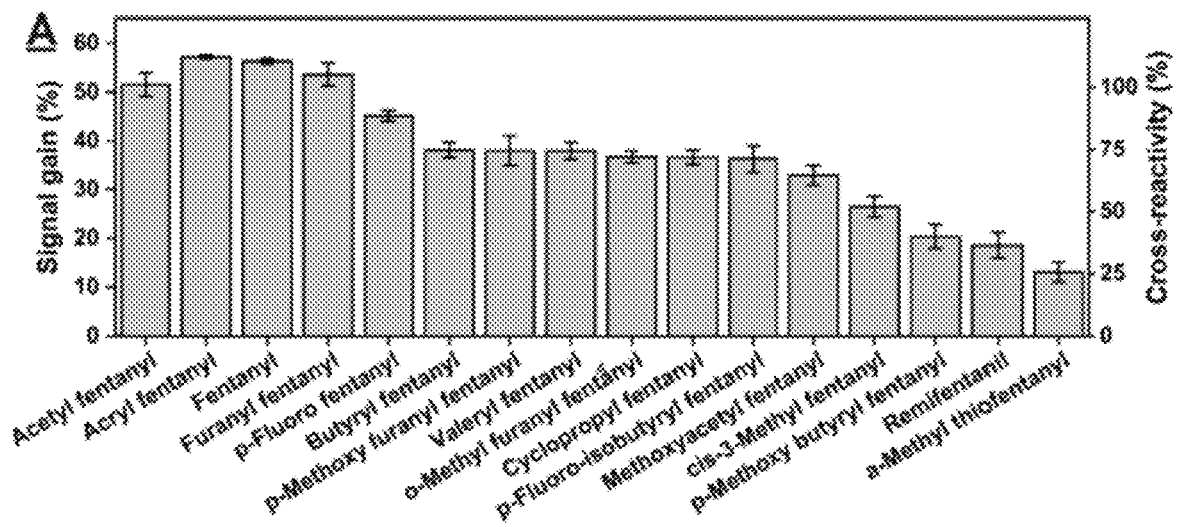
FIGS. 41A-41B show the E-AB sensor performance against fentanyl, 15 of its analogs, and 19 interferent molecules. (A) Cross-reactivity against 5 µM Fentanyl, Acetyl fentanyl, Furanyl fentanyl, Acrylfentanyl, Butyryl fentanyl, Valeryl fentanyl, Cyclopropyl fentanyl, Methoxyacetyl fentanyl, cis-3-methyl Fentanyl, p-methoxy Furanyl fentanyl, p-fluoro Fentanyl, p-methoxy Butyryl fentanyl, Remifentanil, alpha-methyl Thiofentanyl, o-methyl Furanyl fentanyl, and p-Fluoroisobutyryl fentanyl. (B) Specificity against 500 µM (+)-methamphetamine, procaine, papaverine, (+)-pseudoephedrine, benzocaine, quinine, caffeine, acetaminophen, lorazepam, morphine, chlorpromazine, cocaine, diphenhydramine, noscapine, lactose, mannitol, codeine, heroin, or lidocaine. Cross reactivity was calculated relative to the signal produced by 5 µM acetyl fentanyl.
Figure 41B:
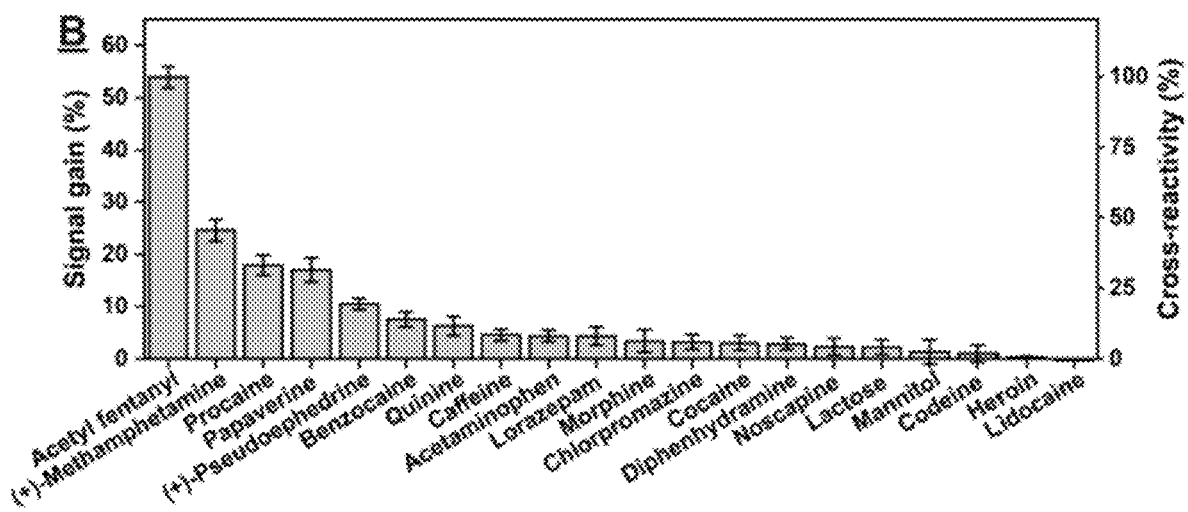

We then used the E-AB sensor with optimized surface coverage to determine the sensor's cross-reactivity against fentanyl and 15 of its analogs at a concentration of 5 μM as well as its specificity against 19 interferent molecules at a concentration of 500 μM. The cross-reactivity of the sensor was calculated relative to the signal produced by 5 μM acetyl fentanyl. We found that the described E-AB sensor demonstrated a high-cross reactivity (>50%) for fentanyl and 12 of its analogs and moderate cross-reactivity (25-49%) for p-methoxy Butyryl fentanyl, Remifentanil, and α-methyl Thiofentanyl (FIG. 41A). In addition, the sensor also demonstrated high specificity against 16 of the tested interferents (cross-reactivity <20%) (FIG. 41B). However, moderate cross-reactivity (32-46%) was observed when testing (+)-methamphetamine, procaine, and papaverine at a 100-fold higher concentration relative to acetyl fentanyl (FIG. 41B).

Figure 42:
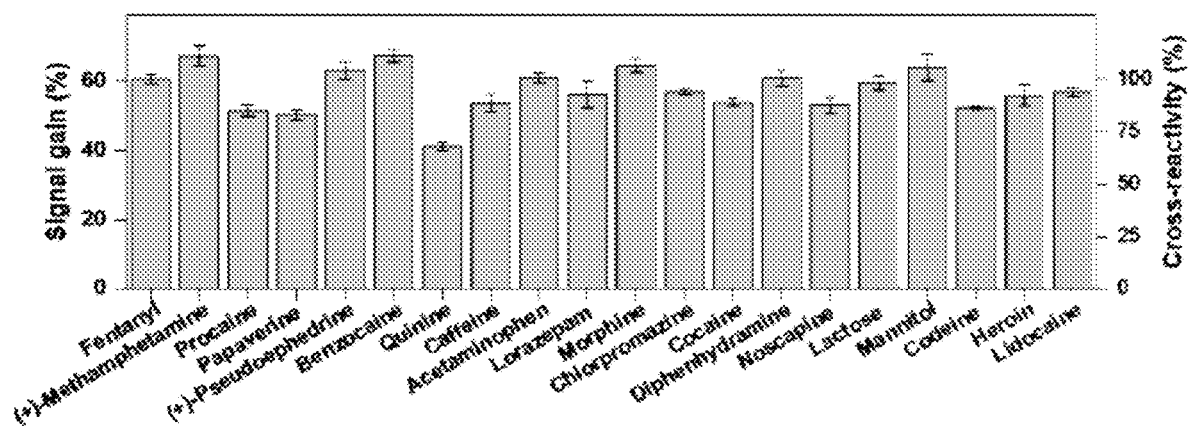
FIG. 42 show the E-AB sensor performance against binary mixtures of 5 µM pure fentanyl or cut with 500 µM (+)-methamphetamine, procaine, papaverine, (+)-pseudoephedrine, benzocaine, quinine, caffeine, acetaminophen, lorazepam, morphine, chlorpromazine, cocaine, diphenhydramine, noscapine, lactose, mannitol, codeine, heroin, or lidocaine.

Finally, to interrogate the sensors performance for real samples, we prepared binary mixtures of 5 μM fentanyl with 500 μM of each one of 19 interferent molecules and evaluated the sensors performance in the comparison of pure fentanyl. We observed almost interference-free signal (86-111% of cross-reactivity relative to pure fentanyl) when testing 16 binary mixtures (FIG. 42). Only when challenged with the samples prepared with papaverine, procaine, and quinine, we observed a slight decrease in the sensors response (67-84% of cross-reactivity relative to pure fentanyl signal) (FIG. 42).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application

We claim:

1. An electrochemical aptamer-based (E-AB) sensor comprising a structure-switching aptamer and an electrode, the structure-switching aptamer being conjugated to the surface of the electrode, the structure-switching aptamer comprising the nucleic acid sequence selected from the group consisting of SEQ ID NOs: 38, 39, 54 and sequences sharing at least 95% identity with SEQ ID NO: 38, 39 or 54.

2. The E-AB sensor according to claim 1, wherein the electrode is a gold or paper-based electrode.

3. The E-AB sensor according to claim 1, wherein the structure-switching aptamer comprises the sequence of SEQ ID NO: 54.

4. The E-AB sensor according to claim 1, wherein the structure-switching aptamer is labeled with a functional group at the 5' or 3' end, and a redox tag at the 3' or 5' end.

5. The E-AB sensor according to claim 4, wherein the functional group is a thiol, sulfide, disulfide, amide, ester, alkenyl, alkynyl, carbonyl, aldehyde, carboxylate, carboxyl, or carbonate ester group.

6. The E-AB sensor according to claim 1, wherein the structure-switching aptamer is labeled with a thiol group at the 5' end, and methylene blue redox tag at the 3'end.

7. The E-AB sensor according to claim 4, wherein the functional group is linked to the 5' or 3' end of the structure-switching aptamer via a first linker.

8. The E-AB sensor according to claim 7, wherein the first linker comprises 1-10 carbons.

9. The E-AB sensor according to claim 4, wherein the redox tag is linked to the 3' or 5' end of the structure-switching aptamer via a second linker.

10. The E-AB sensor according to claim 9, wherein the second linker comprises 1-10 carbons.

11. The E-AB sensor according to claim 1, further comprising a backfiller immobilized on the surface of the electrode.

12. The E-AB sensor according to claim 11, wherein the backfiller is selected from 6-mercapto-1-hexanol (MCH), 1-hexanethiol, thiol-PEG, dithiothreitol (DTT), and combination thereof.

13. The E-AB sensor according to claim 1, wherein the structure-switching aptamer comprises the sequence of SEQ ID NO: 38, or 39.

14. A method for detecting fentanyl and/or an analog thereof in a sample comprising contacting the sample with the E-AB sensor according to claim 1, and detecting fentanyl and/or the analog thereof in the sample by measuring a change in current generated upon binding of fentanyl and/or the analog thereof to the structure-switching aptamer of the E-AB sensor.

15. The method according to claim 14, wherein the sample is a biological sample or an environmental sample.

16. The method according to claim 15, wherein the biological sample is selected from blood, serum, plasma, urine, tears, and saliva.

17. The method according to claim 15, wherein the environmental sample is selected from a water, soil, air, and plant sample.

18. The method according to claim 14, wherein the analog is selected from acetyl fentanyl, furanyl fentanyl, acrylfentanyl, butyryl fentanyl, valeryl fentanyl, cyclopropyl fentanyl, methoxyacetyl fentanyl, cis-3-methyl fentanyl, p-methoxy furanyl fentanyl, p-fluoro fentanyl, p-methoxy butyryl fentanyl, remifentanil, alpha-methyl thiofentanyl, o-methyl furanyl fentanyl, and p-fluoroisobutyryl fentanyl.

* * * * *

SEQUENCE LISTING

```
<160> NUMBER OF SEQ ID NOS: 84

<210> SEQ ID NO 1
<211> LENGTH: 73
<212> TYPE: DNA
<213> ORGANISM: Artificial sequence
<220> FEATURE:
<223> OTHER INFORMATION: a DNA library contemplated for use according to
      the subject invention
<220> FEATURE:
<221> NAME/KEY: misc_feature
<222> LOCATION: (24)..(53)
<223> OTHER INFORMATION: n is a, c, g, or t

<400> SEQUENCE: 1
cgagcatagg cagaacttac gacnnnnnnn nnnnnnnnnn nnnnnnnnnn nnngtcgtaa      60
gagcgagtca ttc                                                        73

<210> SEQ ID NO 2
<211> LENGTH: 25
<212> TYPE: DNA
<213> ORGANISM: Artificial sequence
<220> FEATURE:
<223> OTHER INFORMATION: biotinylated-cDNA sequence
<220> FEATURE:
<221> NAME/KEY: misc_feature
<222> LOCATION: (25)..(25)
<223> OTHER INFORMATION: biotin tag

<400> SEQUENCE: 2
tttttgtcgt aagttctgcc atttt                                           25

<210> SEQ ID NO 3
<211> LENGTH: 20
<212> TYPE: DNA
<213> ORGANISM: Artificial sequence
<220> FEATURE:
<223> OTHER INFORMATION: forward primer
```

<400> SEQUENCE: 3
cgagcatagg cagaacttac          20

<210> SEQ ID NO 4
<211> LENGTH: 20
<212> TYPE: DNA
<213> ORGANISM: Artificial sequence
<220> FEATURE:
<223> OTHER INFORMATION: biotinylated-reverse primer
<220> FEATURE:
<221> NAME/KEY: misc_feature
<222> LOCATION: (1)..(1)
<223> OTHER INFORMATION: biotin tag

<400> SEQUENCE: 4
gaatgactcg ctcttacgac          20

<210> SEQ ID NO 5
<211> LENGTH: 20
<212> TYPE: DNA
<213> ORGANISM: Artificial sequence
<220> FEATURE:
<223> OTHER INFORMATION: reverse primer

<400> SEQUENCE: 5
gaatgactcg ctcttacgac          20

<210> SEQ ID NO 6
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 6
cttacgacac gaggtgtttg gactaagttc ggtttcgggt cgtaag          46

<210> SEQ ID NO 7
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 7
cttacgacga ctgcgtgtgg ccggtgtgag ggagggttgt cgtaag          46

<210> SEQ ID NO 8
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 8
cttacgacag cgggtgtatg tactaagtcc ggttcggtgt cgtaag          46

<210> SEQ ID NO 9
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 9
cttacgacac tggcaggagg gtcgggtgtg ggaacgtggt cgtaag          46

<210> SEQ ID NO 10
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 10
cttacgacca ggcctacgga agcagcgtca gcggggggt cgtaag          46

<210> SEQ ID NO 11
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 11
cttacgacta gtggagtagg gtcgggtagt gggcctcagt cgtaag          46

<210> SEQ ID NO 12
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 12
cttacgacca ccatgggaat cgggtggctt ggaggtgcgt cgtaag          46

<210> SEQ ID NO 13
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 13
cttacgacga gcatcggttt tttcggtgat gtctgggagt cgtaag          46

<210> SEQ ID NO 14
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 14
cttacgacgg aggttgggaa ggaggggag gccggagagt cgtaag          46

<210> SEQ ID NO 15
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 15
cttacgacgg caggtgtttg cactaagtcc ggtatgtcgt cgtaag          46

<210> SEQ ID NO 16

```
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 16
cttacgaccg gtgtgctcgg ggaagggggg ccctaggtgt cgtaag                46

<210> SEQ ID NO 17
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 17
cttacgacat ctgcgtgtgg ccggtgtgag ggagggatgt cgtaag                46

<210> SEQ ID NO 18
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 18
cttacgacca tgggtgtttg cactaagtcc ggttcttggt cgtaag                46

<210> SEQ ID NO 19
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 19
cttacgaccg gtgtgctcgg ggaaggggggc cctaggtggt cgtaag               46

<210> SEQ ID NO 20
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 20
cttacgacac cgggatccag atgggtagtt tgatgtgtgt cgtaag                46

<210> SEQ ID NO 21
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 21
cttacgaccg gcggaaggct ggaggggttg ggggaggtgt cgtaag                46

<210> SEQ ID NO 22
<211> LENGTH: 46
<212> TYPE: DNA
<213> ORGANISM: Artificial sequence
<220> FEATURE:
<223> OTHER INFORMATION: isolated DNA aptamer
```

<400> SEQUENCE: 22
cttacgaccg gtggggaggc cggagttggg aacgggggt cgtaag        46

<210> SEQ ID NO 23
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 23
cttacgaccg ggatcctttg ggcaacctg gtgggcatgt cgtaag        46

<210> SEQ ID NO 24
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 24
cttacgacgg ggtacccgga cagtgatgtt tggtgttcgt cgtaag        46

<210> SEQ ID NO 25
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 25
cttacgacga agcaacgggg tttcggaggg caggtgtcgt cgtaag        46

<210> SEQ ID NO 26
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 26
cttacgaccg gacatgtgat cgggcagctg ggagtcgggt cgtaag        46

<210> SEQ ID NO 27
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 27
cttacgacgt cgaggggtac cctttggcgt tcgtcgaggt cgtaag        46

<210> SEQ ID NO 28
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 28
cttacgacca ggctacgtgg gggagggtgg gaagacgggt cgtaag        46

<210> SEQ ID NO 29

```
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 29
cttacgacac agggtgtgtt gtgctcagtg gtgtatgtgt cgtaag         46

<210> SEQ ID NO 30
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 30
cttacgacag gggtacccgc gtataacgtg gcgttcgtgt cgtaag         46

<210> SEQ ID NO 31
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 31
cttacgacgg ggtgggggcg gcttcccatg ggaggggtgt cgtaag         46

<210> SEQ ID NO 32
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 32
cttacgacga gcgcgtgtgg ccggcgtgag ggaggtgagt cgtaag         46

<210> SEQ ID NO 33
<211> LENGTH: 46
<212> TYPE: DNA
<213> ORGANISM: Artificial sequence
<220> FEATURE:
<223> OTHER INFORMATION: isolated DNA aptamer

<400> SEQUENCE: 33
cttacgacgg gtggggaggc cctctagttg ggaacggtgt cgtaag         46

<210> SEQ ID NO 34
<211> LENGTH: 54
<212> TYPE: DNA
<213> ORGANISM: Artificial sequence
<220> FEATURE:
<223> OTHER INFORMATION: isolated DNA aptamer with a fluorescent label
<220> FEATURE:
<221> NAME/KEY: misc_feature
<222> LOCATION: (1)..(1)
<223> OTHER INFORMATION: fluorescein tag

<400> SEQUENCE: 34
tggcagaact tacgacactg gcaggagggt cgggtgtggg aacgtggtcg taag     54

<210> SEQ ID NO 35
<211> LENGTH: 54
<212> TYPE: DNA
<213> ORGANISM: Artificial sequence
```

```
<220> FEATURE:
<223> OTHER INFORMATION: isolated DNA aptamer with a fluorescent label
<220> FEATURE:
<221> NAME/KEY: misc_feature
<222> LOCATION: (1)..(1)
<223> OTHER INFORMATION: fluorescein tag

<400> SEQUENCE: 35
tggcagaact tacgaccatg ggtgtttgca ctaagtccgg ttcttggtcg taag              54

<210> SEQ ID NO 36
<211> LENGTH: 54
<212> TYPE: DNA
<213> ORGANISM: Artificial sequence
<220> FEATURE:
<223> OTHER INFORMATION: isolated DNA aptamer with a fluorescent label
<220> FEATURE:
<221> NAME/KEY: misc_feature
<222> LOCATION: (1)..(1)
<223> OTHER INFORMATION: fluorescein tag

<400> SEQUENCE: 36
tggcagaact tacgacgagc gcgtgtggcc ggcgtgaggg aggtgagtcg taag              54

<210> SEQ ID NO 37
<211> LENGTH: 15
<212> TYPE: DNA
<213> ORGANISM: Artificial sequence
<220> FEATURE:
<223> OTHER INFORMATION: quencher-modified cDNA strand
<220> FEATURE:
<221> NAME/KEY: misc_feature
<222> LOCATION: (15)..(15)
<223> OTHER INFORMATION: dabcyl quencher tag

<400> SEQUENCE: 37
gtcgtaagtt ctgcc                                                        15

<210> SEQ ID NO 38
<211> LENGTH: 39
<212> TYPE: DNA
<213> ORGANISM: Artificial sequence
<220> FEATURE:
<223> OTHER INFORMATION: truncated DNA aptamer

<400> SEQUENCE: 38
cttacgacca tgggtgtttg cactaagtcc ggttcttgg                              39

<210> SEQ ID NO 39
<211> LENGTH: 32
<212> TYPE: DNA
<213> ORGANISM: Artificial sequence
<220> FEATURE:
<223> OTHER INFORMATION: 5'-thiol and 3'-methelyne blue modified DNA
      aptamer
<220> FEATURE:
<221> NAME/KEY: misc_feature
<222> LOCATION: (1)..(1)
<223> OTHER INFORMATION: thiol group with six-carbon spacer
<220> FEATURE:
<221> NAME/KEY: misc_feature
<222> LOCATION: (32)..(32)
<223> OTHER INFORMATION: methylene blue redox tag

<400> SEQUENCE: 39
ccatgggtgt tgcactaag tccggttctt gg                                      32

<210> SEQ ID NO 40
<211> LENGTH: 8
```

```
<212> TYPE: DNA
<213> ORGANISM: Artificial sequence
<220> FEATURE:
<223> OTHER INFORMATION: complimentary DNA sequence

<400> SEQUENCE: 40 gtcgtaag                                                                  8

<210> SEQ ID NO 41
<211> LENGTH: 46
<212> TYPE: DNA
<213> ORGANISM: Artificial sequence
<220> FEATURE:
<223> OTHER INFORMATION: sequence of a truncated DNA aptamer library
<220> FEATURE:
<221> NAME/KEY: misc_feature
<222> LOCATION: (9)..(38)
<223> OTHER INFORMATION: n is a, c, g, or t

<400> SEQUENCE: 41
cttacgacnn nnnnnnnnnn nnnnnnnnnn nnnnnnnngt cgtaag                        46

<210> SEQ ID NO 42
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 42
acgaggtgtt tggactaagt tcggtttcgg                                          30

<210> SEQ ID NO 43
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 43
gactgcgtgt ggccggtgtg agggagggtt                                          30

<210> SEQ ID NO 44
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 44
agcgggtgta tgtactaagt ccggttcggt                                          30

<210> SEQ ID NO 45
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 45
actggcagga gggtcgggtg tgggaacgtg                                          30

<210> SEQ ID NO 46
<211> LENGTH: 30
<212> TYPE: DNA
<213> ORGANISM: Artificial sequence
<220> FEATURE:
```

<223> OTHER INFORMATION: sequence of the N30 region of DNA aptamer

<400> SEQUENCE: 46
caggcctacg gaagcagcgt cagcggggggg                                           30

<210> SEQ ID NO 47
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 47
tagtggagta gggtcgggta gtgggcctca                                            30

<210> SEQ ID NO 48
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 48
caccatggga atcgggtggc ttggaggtgc                                            30

<210> SEQ ID NO 49
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 49
gagcatcggt tttttcggtg atgtctggga                                            30

<210> SEQ ID NO 50
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 50
ggaggttggg aaggaggggg aggccggaga                                            30

<210> SEQ ID NO 51
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 51
ggcaggtgtt tgcactaagt ccggtatgtc                                            30

<210> SEQ ID NO 52
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 52
cggtgtgctc ggggaagggg ggccctaggt                                            30

```
<210> SEQ ID NO 53
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 53
atctgcgtgt ggccggtgtg agggagggat                                        30

<210> SEQ ID NO 54
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 54
catgggtgtt tgcactaagt ccggttcttg                                        30

<210> SEQ ID NO 55
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 55
cggtgtgctc ggggaaggggg gccctaggtg                                       30

<210> SEQ ID NO 56
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 56
accgggatcc agatgggtag tttgatgtgt                                        30

<210> SEQ ID NO 57
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 57
cggcggaagg ctggaggggt tgggggaggt                                        30

<210> SEQ ID NO 58
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 58
cggtggggag gccggagttg ggaacggggg                                        30

<210> SEQ ID NO 59
<211> LENGTH: 30
<212> TYPE: DNA
<213> ORGANISM: Artificial sequence
<220> FEATURE:
<223> OTHER INFORMATION: sequence of the N30 region of DNA aptamer
```

<400> SEQUENCE: 59
cgggatcctt tgggacaacc tggtgggcat         30

<210> SEQ ID NO 60
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 60
ggggtacccg gacagtgatg tttggtgttc         30

<210> SEQ ID NO 61
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 61
gaagcaacgg ggtttcggag ggcaggtgtc         30

<210> SEQ ID NO 62
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 62
cggacatgtg atcgggcagc tgggagtcgg         30

<210> SEQ ID NO 63
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 63 gtcgagggt accctttggc gttcgtcgag         30

<210> SEQ ID NO 64
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 64
caggctacgt gggggagggt gggaagacgg         30

<210> SEQ ID NO 65
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 65
acagggtgtg ttgtgctcag tggtgtatgt         30

<210> SEQ ID NO 66
<211> LENGTH: 30

```
<212> TYPE: DNA
<213> ORGANISM: Artificial sequence
<220> FEATURE:
<223> OTHER INFORMATION: sequence of the N30 region of DNA aptamer

<400> SEQUENCE: 66
aggggtaccc gcgtataacg tggcgttcgt                                    30

<210> SEQ ID NO 67
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 67
ggggtggggg cggcttccca tgggaggggt                                    30

<210> SEQ ID NO 68
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 68
gagcgcgtgt ggccggcgtg agggaggtga                                    30

<210> SEQ ID NO 69
<211> LENGTH: 30
<212> TYPE: DNA
<213> ORGANISM: Artificial sequence
<220> FEATURE:
<223> OTHER INFORMATION: sequence of the N30 region of DNA aptamer

<400> SEQUENCE: 69
gggtggggag gccctctagt tgggaacggt                                    30

<210> SEQ ID NO 70
<211> LENGTH: 54
<212> TYPE: DNA
<213> ORGANISM: Artificial sequence
<220> FEATURE:
<223> OTHER INFORMATION: a sequence of a DNA aptamer library with 5'
      overhang
<220> FEATURE:
<221> NAME/KEY: misc_feature
<222> LOCATION: (17)..(46)
<223> OTHER INFORMATION: n is a, c, g, or t

<400> SEQUENCE: 70
tggcagaact tacgacnnnn nnnnnnnnnn nnnnnnnnnn nnnnnngtcg taag          54

<210> SEQ ID NO 71
<211> LENGTH: 8
<212> TYPE: DNA
<213> ORGANISM: Artificial sequence
<220> FEATURE:
<223> OTHER INFORMATION: sequence of non-N30 region of DNA aptamer

<400> SEQUENCE: 71 cttacgac                                                             8

<210> SEQ ID NO 72
<211> LENGTH: 16
<212> TYPE: DNA
<213> ORGANISM: Artificial sequence
```

```
<220> FEATURE:
<223> OTHER INFORMATION: sequence of non-N30 region of DNA aptamer

<400> SEQUENCE: 72
tggcagaact tacgac                                                      16

<210> SEQ ID NO 73
<211> LENGTH: 14
<212> TYPE: DNA
<213> ORGANISM: Artificial sequence
<220> FEATURE:
<223> OTHER INFORMATION: quencher-modified cDNA strand
<220> FEATURE:
<221> NAME/KEY: misc_feature
<222> LOCATION: (14)..(14)
<223> OTHER INFORMATION: dabcyl quencher tag

<400> SEQUENCE: 73
tcgtaagttc tgcc                                                        14

<210> SEQ ID NO 74
<211> LENGTH: 14
<212> TYPE: DNA
<213> ORGANISM: Artificial sequence
<220> FEATURE:
<223> OTHER INFORMATION: quencher-modified cDNA strand
<220> FEATURE:
<221> NAME/KEY: misc_feature
<222> LOCATION: (14)..(14)
<223> OTHER INFORMATION: dabcyl quencher tag

<400> SEQUENCE: 74
gtcgtaagtt ctgc                                                        14

<210> SEQ ID NO 75
<211> LENGTH: 15
<212> TYPE: DNA
<213> ORGANISM: Artificial sequence
<220> FEATURE:
<223> OTHER INFORMATION: quencher-modified cDNA strand
<220> FEATURE:
<221> NAME/KEY: misc_feature
<222> LOCATION: (15)..(15)
<223> OTHER INFORMATION: dabcyl quencher tag

<400> SEQUENCE: 75
gttgtaagtt ctgcc                                                       15

<210> SEQ ID NO 76
<211> LENGTH: 15
<212> TYPE: DNA
<213> ORGANISM: Artificial sequence
<220> FEATURE:
<223> OTHER INFORMATION: quencher-modified cDNA strand
<220> FEATURE:
<221> NAME/KEY: misc_feature
<222> LOCATION: (15)..(15)
<223> OTHER INFORMATION: dabcyl quencher tag

<400> SEQUENCE: 76
gtcgtaggtt ctgcc                                                       15

<210> SEQ ID NO 77
<211> LENGTH: 15
<212> TYPE: DNA
<213> ORGANISM: Artificial sequence
<220> FEATURE:
<223> OTHER INFORMATION: quencher-modified cDNA strand
<220> FEATURE:
```

```
<221> NAME/KEY: misc_feature
<222> LOCATION: (15)..(15)
<223> OTHER INFORMATION: dabcyl quencher tag

<400> SEQUENCE: 77
gtcgtaagtt ttgcc                                                    15

<210> SEQ ID NO 78
<211> LENGTH: 46
<212> TYPE: DNA
<213> ORGANISM: Artificial sequence
<220> FEATURE:
<223> OTHER INFORMATION: mutant DNA aptamer

<400> SEQUENCE: 78
cttacgacta gtgtagtagg gtcgggtagt gggcctcagt cgtaag                  46

<210> SEQ ID NO 79
<211> LENGTH: 46
<212> TYPE: DNA
<213> ORGANISM: Artificial sequence
<220> FEATURE:
<223> OTHER INFORMATION: mutant DNA aptamer

<400> SEQUENCE: 79
cttacgacta gtggagtagt gtcgggtagt gggcctcagt cgtaag                  46

<210> SEQ ID NO 80
<211> LENGTH: 46
<212> TYPE: DNA
<213> ORGANISM: Artificial sequence
<220> FEATURE:
<223> OTHER INFORMATION: mutant DNA aptamer

<400> SEQUENCE: 80
cttacgacta gtggagtagg gtagggtagt gggcctcagt cgtaag                  46

<210> SEQ ID NO 81
<211> LENGTH: 46
<212> TYPE: DNA
<213> ORGANISM: Artificial sequence
<220> FEATURE:
<223> OTHER INFORMATION: mutant DNA aptamer

<400> SEQUENCE: 81
cttacgacta gtggagtagg gtcgtgtagt gggcctcagt cgtaag                  46

<210> SEQ ID NO 82
<211> LENGTH: 46
<212> TYPE: DNA
<213> ORGANISM: Artificial sequence
<220> FEATURE:
<223> OTHER INFORMATION: mutant DNA aptamer

<400> SEQUENCE: 82
cttacgacta gtggagtagg gtcgggtagt gtgcctcagt cgtaag                  46

<210> SEQ ID NO 83
<211> LENGTH: 54
<212> TYPE: DNA
<213> ORGANISM: Artificial sequence
<220> FEATURE:
<223> OTHER INFORMATION: isolated DNA aptamer with a fluorescent label
<220> FEATURE:
<221> NAME/KEY: misc_feature
<222> LOCATION: (1)..(1)
<223> OTHER INFORMATION: fluorescein tag
```

```
<400> SEQUENCE: 83
tggcagaact tacgactagt ggagtagggt cgggtagtgg gcctcagtcg taag            54

<210> SEQ ID NO 84
<211> LENGTH: 15
<212> TYPE: DNA
<213> ORGANISM: Artificial sequence
<220> FEATURE:
<223> OTHER INFORMATION: cDNA

<400> SEQUENCE: 84
gtcgtaagtt ctgcc                                                      15
```